(12) United States Patent
Peng et al.

(10) Patent No.: US 10,393,684 B2
(45) Date of Patent: Aug. 27, 2019

(54) MICRO MAGNETIC RESONANCE RELAXOMETRY

(71) Applicant: Massachusetts Institute of Technology, Cambridge, MA (US)

(72) Inventors: Weng Kung Peng, Singapore (SG); Jongyoon Han, Cambridge, MA (US); Tze Ping Loh, Singapore (SG)

(73) Assignees: Massachusetts Institute of Technology, Cambridge, MA (US); National University Hospital (S) Pte, Singapore (SG)

( * ) Notice: Subject to any disclaimer, the term of this patent is extended or adjusted under 35 U.S.C. 154(b) by 483 days.

(21) Appl. No.: 15/136,887

(22) Filed: Apr. 23, 2016

(65) Prior Publication Data
US 2016/0313425 A1    Oct. 27, 2016

Related U.S. Application Data

(60) Provisional application No. 62/152,718, filed on Apr. 24, 2015.

(51) Int. Cl.
*G01N 24/08* (2006.01)
*G01R 33/44* (2006.01)
*G16H 50/30* (2018.01)

(52) U.S. Cl.
CPC ........... *G01N 24/08* (2013.01); *G01R 33/448* (2013.01); *G16H 50/30* (2018.01); *Y02A 90/26* (2018.01)

(58) Field of Classification Search
None
See application file for complete search history.

(56) References Cited

U.S. PATENT DOCUMENTS

| | | | |
|---|---|---|---|
| 4,651,097 A * | 3/1987 | Iwaoka | G01R 33/482 324/307 |
| 5,674,692 A | 10/1997 | Baekkeskov et al. | |
| 8,465,988 B2 | 6/2013 | Jensen | |
| 2006/0006865 A1 | 1/2006 | Zhang et al. | |
| 2007/0238793 A1 | 10/2007 | Lockwood | |
| 2013/0273523 A1 | 10/2013 | Neely et al. | |

FOREIGN PATENT DOCUMENTS

| | | |
|---|---|---|
| DE | 2013103969 U1 | 9/2013 |
| EP | 1595573 B1 | 1/2008 |
| WO | 2006/095238 A1 | 9/2006 |
| WO | 2012/118442 A1 | 9/2012 |

OTHER PUBLICATIONS

Notification of Transmittal of the International Search Report and the Written Opinion of the International Searching Authority, or the Declaration dated Sep. 14, 2016, issued in International Application No. PCT/US16/29075, One page.

(Continued)

*Primary Examiner* — Paresh H Patel
(74) *Attorney, Agent, or Firm* — Steptoe & Johnson LLP

(57) ABSTRACT

A low-cost and bench-top magnetic resonance relaxometer can be used for ex-vivo biochemical stress tests on plasma/erythrocytes, enabling deep-phenotyping of an individual's oxidative status, susceptibility and capacity.

23 Claims, 68 Drawing Sheets

(56) References Cited

OTHER PUBLICATIONS

International Search Report dated Sep. 14, 2016, issued in International Application No. PCT/US16/29075, Five pages.
Written Opinion of the International Searching Authority dated Sep. 14, 2016, issued in International Application No. PCT/US16/29075, 16 pages.
Edden, R. et al. "Longitudinal and Multi-Echo Transverese Relaxation Times of Normal Breast Tissue at 3 Tesla", Sep. 29, 2010 [retrieved Jun. 27, 2016]; Retrieved from the Internet <URL:http://www.ncbi.nim.nih.gov/pmc/articles/PMC3154635/>, p. 982, col. 2, paragraphs 3 & 4, p. 985, figure b, p. 986, col. 10, paragraph 3.
Farrow, N. et al. "Characterization of the Backbone Dynamics of Folded and Denatured States of an SH3 Domain", Oct. 10, 1996 [retrieved Jun. 27, 2016]; Retrieved from the Internet <URL:http://www.ncbi.nim.nih.gov/pubmed/9054544>, p. 2390, citation 1, p. 2396, Table 1.

* cited by examiner

| Hemoglobin | Oxidation State | Number of unpaired electrons | A-ratio | Magnetic States |
|---|---|---|---|---|
| Oxy-Hb | Fe(II) | nil | 4.13 | Diamagnetic |
| Deoxy-Hb | Fe(II) | 4 | 5.02 | Paramagnetic |
| Nitrosyl-Hb | Fe(II) | ? | 1.69 | Paramagnetic |
| Hemichrome | Fe(III) | 3 | 5.58 | Paramagnetic |
| Met-Hb | Fe(III) | 5 | 1.94 | Paramagnetic |
| Feryl-Hb | Fe(IV) | nil | 3.76 | Diamagnetic |
| Oxoferryl-Hb | Fe(IV) | 1(globin-based) | 2.78 | Paramagnetic |

FIG. 1E

| | ROC-AUC (nitrite concentration) | | | | | | |
|---|---|---|---|---|---|---|---|
| | 0mM | 0.5mM | 2.0mM | 4.0mM | 6.0mM | 8.0mM | 10mM |
| oxy-Hb baseline | - | 0.444 | 0.875 | 1 | 1 | 1 | 1 |
| met-Hb baseline | 1 | 1 | 1 | 1 | 0.95 | 0.736 | - |

FIG. 11D

MICRO MAGNETIC RESONANCE RELAXOMETRY

PRIORITY CLAIM

This application claims priority to U.S. Provisional Application No. 62/152,718, filed Apr. 24, 2015, which is incorporated by reference in its entirety.

TECHNICAL FIELD

This invention relates to magnetic resonance relaxometry.

BACKGROUND

Diabetes mellitus (DM) is one of the fastest growing health burdens that is projected to affect 592 million people worldwide by 2035. DM is defined by a persistent elevation of glucose concentration. Under chronic hyperglycemic conditions, glucose is non-enzymatically attached to proteins (glycation), which has deleterious effects on their structure and function. Glycated hemoglobin A1c ($HbA_{1c}$) is the hemoglobin with glucose attached to the N-terminus valine, which reflects the glycemic burden of an individual over the previous 2-3 months. Therefore, it is the recommended biomarker for monitoring the glucose control of DM patients.

Magnetic resonance relaxometry (MRR) is a technique used in nuclear magnetic resonance (NMR) spectroscopy and magnetic resonance imaging (MRI) to acquire spin-echoes of (predominantly) water content of the cells/tissues. Recent advances in NMR system miniaturization have raised the prospect of applying these techniques in point-of-care diagnostic setting. These include immuno-magnetic labeling based (e.g. tumor cells, tuberculosis and magneto-DNA detection of bacteria) and label-free µMRR detection of various diseases (e.g., oxygenation/oxidation level of the blood and malaria screening).

SUMMARY

A method of monitoring a disease status can include obtaining a sample, such as a blood sample, from a subject, measuring a longitudinal relaxation time and a transverse relaxation time in the sample, and assessing a redox state of the sample from the longitudinal relaxation time and the transverse relaxation time of the sample.

In one aspect, assessing the redox state can include plotting a magnetic state diagram of a longitudinal relaxation time and a transverse relaxation time, and interpreting the state of the sample based on the location of the sample in the diagram. Assessing the redox state can include calculating a ratio of longitudinal relaxation time to transverse relaxation time of the sample, and comparing the ratio with a predetermined ratio of a reference sample. Measuring the longitudinal relaxation time and the transverse relaxation time can include inserting the sample within a detection coil of a magnetic resonance relaxometry device.

In another aspect, a method of identifying a risk for diabetes mellitus in a patient can include measuring a longitudinal relaxation time and a transverse relaxation time using a magnetic resonance relaxometry device in a sample, such as a blood sample, of the patient, and assigning a risk level to a subject based on a ratio of the longitudinal relaxation time and the transverse relaxation time.

In another aspect, a method of assessing a redox state of a sample can include plotting a magnetic state diagram of a longitudinal relaxation time and a transverse relaxation time, wherein the longitudinal relaxation time and the transverse relaxation time are measured using a magnetic resonance relaxometry device, and interpreting the state of the sample based on the location of the sample in the diagram.

In another aspect, a method of assessing a redox state of a sample can include calculating a ratio of longitudinal relaxation time to transverse relaxation time of the sample, wherein the longitudinal relaxation time and the transverse relaxation time are measured using a magnetic resonance relaxometry device, and comparing the ratio with a predetermined ratio of a reference sample.

The magnetic resonance relaxometry device can include a radio-frequency spectrometer comprising at least one field-programmable gate array chip, a power amplifier electrically connected with the radio-frequency spectrometer and amplifying an electrical output of the radio-frequency spectrometer, thereby producing an amplified electrical signal comprising between about 0.1 Watts and about 10 Watts power, a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter, and at least one magnet supplying an external magnetic field to a detection region of the radio-frequency detection probe, the external magnetic field being less than about 3 Tesla.

Alternatively, the magnetic resonance relaxometry device can include conventional NMR spectroscopy using higher external magnetic field higher than about 3 Tesla.

The sample can be body fluid, tissue or cell samples. In certain embodiments, the body fluid can be blood, sweat, urine or other tissues/cells. In certain embodiments, the blood sample can be plasma or red blood cells. These methods can be used to monitor acute or chronic oxidative stress. The chronic oxidative stress can include diabetes mellitus. The redox state can be a level of oxidative stress; for example, a level of oxidative stress of hemoglobin. Alternatively, the redox state can be a level of nitrosative stress; for example, a level of nitrosative stress of hemoglobin.

A method of monitoring a hemoglobin state using a magnetic state diagram can be represented by a two-dimensional plot of a longitudinal relaxation time and a transverse relaxation time.

A magnetic state diagram for assessing redox state of a sample can include a two-dimensional plot of a longitudinal relaxation time and a transverse relaxation time of the sample.

Other aspects, embodiments, and features will be apparent from the following description, the drawings, and the claims.

BRIEF DESCRIPTION OF THE DRAWINGS

FIG. 1E shows the corresponding magnetic states, number of unpaired electron, A-ratio, and iron oxidation state.

FIG. 2G shows the amplitudes of the oscillation depending on the nitrite concentrations. FIG. 2H shows $T_1$-$T_2$ trajectories with various nitrite concentrations.

FIG. 4C shows the corresponding statistical distribution based on A-ratio index for both FIGS. 4A and 4B. FIG. 4D shows characteristic (ROC) analysis that the initial matching baseline between the subjects from poor and good glycaemic group had increased upon nitrite stress. FIG. 4E shows variability of nitrosative susceptibility for good glycaemic control group.

FIG. 5B shows the breakdown details in A-ratio for poor and good glycaemic control subgroups as opposed to non-DM. FIG. 5C shows frequency plot of two binomials overlapped for non-DM subjects and good glycaemic control subjects (right bars) and poor glycaemic control subjects (left bars). FIG. 5D shows ROC-AUC curve.

FIG. 6D shows the $A_{peroxidative}$ index and FIG. 6E shows normalized $A_{baseline}$-$A_{peroxidative}$ for the three glycaemic groups, respectively.

FIG. 7A shows time dependent kinetic profile for nitrite-induced oxidation of oxy-Hb as measured by MRR and photospectrometry. FIG. 7B shows correlation between MRR and photospectrometry measurements.

FIGS. 8A and 8C show photospectrometry spectras for diluted oxy-Hb:met-Hb for (control, 0.5%, 5%, 10%, 20%, 100%). FIGS. 8B and 8D show plot of concentration against the dilution prepared using one tailed student's t-test of paired test to calculate the P-value.

FIG. 9D shows $T_1$-$T_2$ diagram (left panel) and $T_2$ relaxation times (mid panel) and $T_1$ relaxation times (right panel) against the met-Hb concentration for sample D using one tailed student's t-test of paired test to calculate the P-value.

FIG. 10A shows $T_1$-$T_2$ diagram of RBCs exposed to salicylic (round) and control (square) in in vitro environment at different time points. FIG. 10B shows the corresponding A-ratio in time evolution. FIG. 10C shows $T_1$-$T_2$ diagram for RBCs of non DM (square) and DM subjects (round) exposed to sodium salicylic. FIG. 10D shows the corresponding A-ratio.

FIGS. 11A-11D show nitrite concentration selection criteria for nitrite-induced oxidation of RBC assays a short time period. FIG. 11A shows the actual micrograph of the subjects' blood with various nitrite concentrations. FIG. 11B shows A-ratio of randomly assigned subjects taken from a range of $HbA_{1c}$ their responses over various nitrite stress concentrations on RBCs. FIG. 10C shows concentration of nitrite used against the A-ratio correspond to FIG. 11B. FIG. 11D shows ROC-AUC calculated for each nitrite concentration against the oxy-Hb and met-Hb baseline.

FIG. 12A shows A-ratio of randomly assigned subjects taken from a range of $HbA_{1c}$ and their responses over various nitrite stress concentrations on RBCs. FIG. 12B shows the log-log plot of FIG. 12A.

FIG. 14A shows A-ratio of randomly assigned subjects and their responses over various peroxide stress concentrations human serum albumin. FIG. 14B shows concentration of hydrogen peroxide against A-ratio corresponding to FIG. 14A. FIG. 14C shows ROC-AUC calculated for each peroxide concentration against the non-oxidized and non-oxidized serum baseline. FIGS. 14D and 14E show HSA for 2 subjects at various peroxide concentrations at taken by photospectrometry.

FIG. 15A shows $T_1$-$T_2$ diagram of in vitro glycated glucose addition to plasma serum before (blank round) and after (filled round) peroxidative stress. The respective controls without glucose addition are shown in black (square). Each point represents readings taken from three different subjects. FIGS. 15B and 15C show the breakdown of each subject in $A_{baseline}$-ratio.

DETAILED DESCRIPTION

Figure 1A:
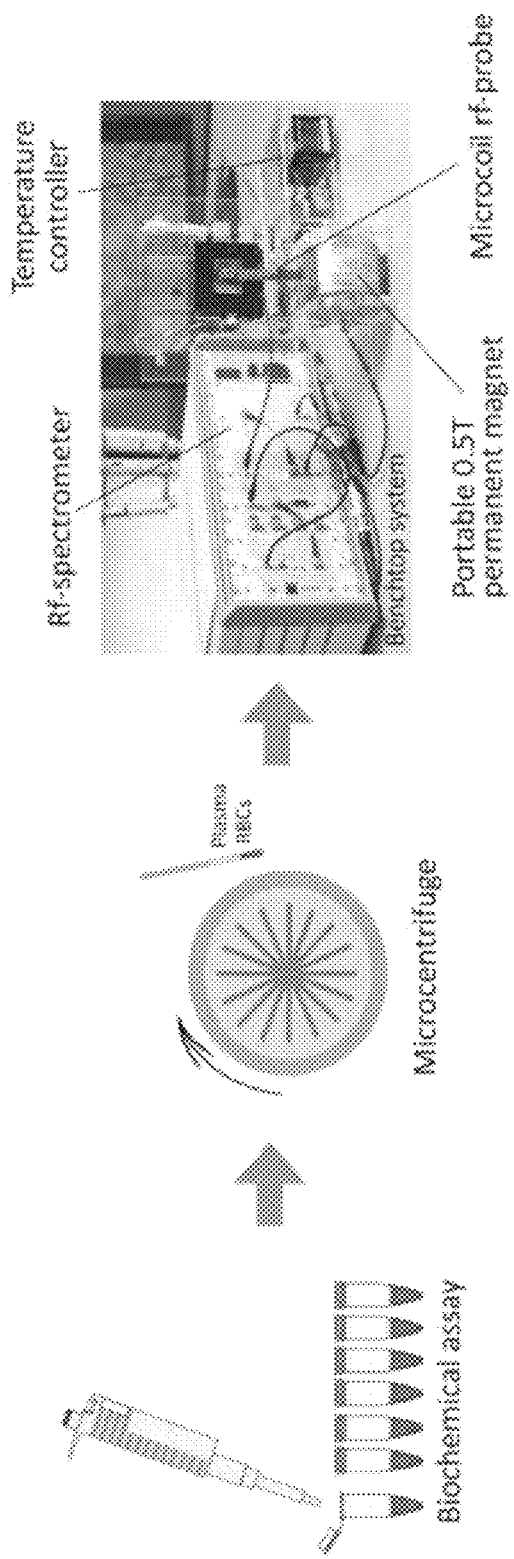
FIG. 1A shows schematic illustration of the MRR assays.

A major pathological effect of diabetes mellitus (DM) is oxidative-nitrosative stress (ONS), which causes many of the secondary complications of diabetes including nephropathy, retinopathy, neuropathy, and cardiovascular diseases. ONS changes the reduction-oxidation state of plasma/erythrocytes, thereby changing their magnetic properties.

$HbA_{1c}$, while widely used, does not adequately predict complications associated with oxidative stress, which is one of the major pathological processes that promote the complications commonly seen in patients with diabetes, such as nephropathy, retinopathy, neuropathy, and cardiovascular diseases. Oxidative-nitrosative stress can damage nuclei acids, lipids and proteins, which severely compromise cellular health and induce a range of cellular responses leading to cell death. See, Holley, A. & Cheeseman, K. Measuring free radical reactions in vivo. *British Medical Bulletin* 49, 494-505 (1993), and Maritim, A., Sanders, R. & Watkins, r. J. Diabetes, oxidative stress, and antioxidants: a review. *Journal of biochemical and molecular toxicology* 17, 24-38 (2003), each of which is incorporated by reference in its entirety. Direct measurement of oxidative stress and each patient's susceptibility may improve the prediction of disease risks related to oxidative stress in subgroups of DM patients.

Currently, an individual's oxidative stress cannot be easily characterized in detail using available biomarkers. See, Jackson, M. J. An overview of methods for assessment of free radical activity in biology. in *PROCEEDINGS-NUTRITION SOCIETY OF LONDON*, Vol. 58 1001-1006 (Cambridge Univ Press, 1999), and Kopani, M., Celec, P., Danisovic, L., Michalka, P. & Biro, C. Oxidative stress and electron spin resonance. *Clin. Chim. Acta* 364, 61-66 (2006), each of which is incorporated by reference in its entirety. This has contributed to the lack of understanding of the pathological effects of acute and prolonged exposure to oxidative stress. Over the years, several methods have been developed to detect the redox properties of the blood, which mainly rely on the optical or magnetic properties of the inorganic iron-chelate of hemoglobin (Hb) and plasma albumin. See, Nonoyama, A. University of South Florida (2004), Shah, S. S., et al. A novel cytofluorometric assay for the detection and quantification of glucose-6-phosphate dehydrogenase deficiency. *Sci Rep* 2, 299, Olsson, M. G., et al. Pathological Conditions Involving Extracellular Hemoglobin: Molecular Mechanisms, Clinical Significance, and Novel Therapeutic Opportunities for Î±1-Microglobulin. *Antioxidants & Redox Signaling* 17, 813-846, and Svistunenko, D. A., Patel, R. P., Voloshchenko, S. V. & Wilson, M. T. The globin-based free radical of ferryl hemoglobin is detected in normal human blood. *J. Biol. Chem.* 272, 7114-7121 (1997), each of which is incorporated by reference in its entirety. Oxidative stress biomarkers are often short-lived and reactive. The reactive oxygen species (ROS) and reactive nitrogen species (RNS) can be detected via electron spin resonance (ESR). See, Emanuel, N. M., Saprin, A. N., Shabalkin, V. A., Kozlova, L. E. & Krugljakova, K. E. Detection and investigation of a new type of ESR signal characteristic of some tumour tissues. *Nature* 222, 165-167 (1969), and Takeshita, K. & Ozawa, T. Recent progress in in vivo ESR spectroscopy. *J Radiat Res* 45, 373-384 (2004), each of which is incorporated by reference in its entirety. The ESR approach is hampered by inherent sample instability issues, and hence has low reproducibility and limited sensitivity. Stable molecular products formed from reactions with ROS/RNS, such as the oxidation targets (e.g., lipid, protein, acid nucleic) are measurable using a range of spectrophometric assays and mass spectrometry (MS). See, Nikov, G., Bhat, V., Wishnok, J. S. & Tannenbaum, S. R. Analysis of nitrated proteins by nitrotyrosine-specific affinity probes and mass spectrometry. *Analytical biochemistry* 320, 214-222 (2003), and Jiang, T., Zhou, X., Taghizadeh, K., Dong, M. & Dedon, P. C. N-formylation of lysine in histone proteins as a secondary modification arising from oxidative DNA damage. *Proceedings of the National Academy of Sciences* 104, 60-65 (2007), each of which is incorporated by reference in its entirety. Nevertheless, fluorescent-staining often causes cell-toxicity, and therefore the assays may not provide information that reflects in vivo conditions. See, Spasojević, I., Bajić, A., Jovanović, K., Spasić, M. & Andjus, P. Protective role of fructose in the metabolism of astroglial C6 cells exposed to hydrogen peroxide. *Carbohydrate research* 344, 1676-1681 (2009), and Buckman, J. F., et al. MitoTracker labeling in primary neuronal and astrocytic cultures: influence of mitochondrial membrane potential and oxidants. *Journal of neuroscience methods* 104, 165-176 (2001), each of which is incorporated by reference in its entirety. Ultraviolet-visible light spectroscopy has poor spectral resolution, and sensitivity and globin-associated free radical in Hb is not optically visible (Supplementary FIGS. 7-9). See, Della *Longa*, S., et al. Iron site structure of two irreversible hemichromes from human hemoglobin, untreated and oxidized to sulfoxide at MetD6 (55) beta. *Biochimica et biophysica acta* 1294, 72-76 (1996), and Rifkind, J. M., Abugo, O., Levy, A. & Heim, J. Detection, formation, and relevance of hemichromes and hemochromes. *Methods in enzymology* 231, 449-480 (1993), each of which is incorporated by reference in its entirety. MS-based analysis of ROS/RNS reaction products is a powerful and sensitive technique to reveal detailed chemistry of these species, yet requires substantial sample preparation and therefore difficult to be employed as a rapid screening tool. See, Aebersold, R. & Mann, M. Mass spectrometry-based proteomics. *Nature* 422, 198-207 (2003), which is incorporated by reference in its entirety.

Disclosed herein is a method to rapidly quantify the composite redox state of the hemoglobin/plasma with a bench-top sized micro magnetic resonance relaxometry (µMRR) system using a $T_1$ (longitudinal relaxation time)-$T_2$ (transverse relaxation time) diagram (FIGS. 1A-F).

Also disclosed is a method of monitoring a disease status can include obtaining a sample from a subject, measuring a longitudinal relaxation time and a transverse relaxation time in the sample, and assessing a redox state of the sample from the longitudinal relaxation time and the transverse relaxation time of the sample. The sample can be body fluid, tissue or cell samples. In certain embodiments, the body fluid can be blood, sweat, or urine. In certain embodiments, the blood sample can be plasma/serum or red blood cells. The method can be used to monitor acute or chronic oxidative stress. The chronic oxidative stress can include diabetes mellitus. The redox state can be a level of oxidative stress; for example, a level of oxidative stress of hemoglobin. Alternatively, the redox state can be a level of nitrosative stress; for example, a level of nitrosative stress of hemoglobin.

In one aspect, assessing the redox state can include plotting a magnetic state diagram of a longitudinal relaxation time and a transverse relaxation time, and interpreting the state of the sample based on the location of the sample in the diagram. Assessing the redox state can include calculating a ratio of longitudinal relaxation time to transverse relaxation time of the sample, and comparing the ratio with a predetermined ratio of a reference sample. Measuring the longitudinal relaxation time and the transverse relaxation time can include inserting the blood sample within a detection coil of a magnetic resonance relaxometry device.

In another aspect, a method of identifying a risk for diabetes mellitus in a patient can include measuring a longitudinal relaxation time and a transverse relaxation time using a magnetic resonance relaxometry device in a blood sample of the patient, and assigning a risk level to a subject based on a ratio of the longitudinal relaxation time and the transverse relaxation time.

In another aspect, a method of assessing a redox state of a sample can include plotting a magnetic state diagram of a longitudinal relaxation time and a transverse relaxation time, wherein the longitudinal relaxation time and the transverse relaxation time are measured using a magnetic resonance relaxometry device, and interpreting the state of the sample based on the location of the sample in the diagram.

In another aspect, a method of assessing a redox state of a sample can include calculating a ratio of longitudinal relaxation time to transverse relaxation time of the sample, wherein the longitudinal relaxation time and the transverse relaxation time are measured using a magnetic resonance relaxometry device, and comparing the ratio with a predetermined ratio of a reference sample.

In another aspect, a method of monitoring a hemoglobin state using a magnetic state diagram can be represented by a two-dimensional plot of a longitudinal relaxation time and a transverse relaxation time.

A magnetic state diagram for assessing redox state of a sample can include a two-dimensional plot of a longitudinal relaxation time and a transverse relaxation time of the sample.

A biosensor, palm-sized device and method based on magnetic resonance relaxometry is described in WO 2012/118,442, which is incorporated by reference in its entirety. Vo, N., et al. also described a highly integrated, low cost, palm-top sized magnetic resonance relaxometry system for rapid blood screening in *The 15th International Conference on Biomedical Engineering*, Vol. 43, 558-561 (Springer International Publishing), which is incorporated by reference in its entirety.

The magnetic resonance relaxometry device can include a radio-frequency spectrometer comprising at least one field-programmable gate array chip, a power amplifier electrically connected with the radio-frequency spectrometer and amplifying an electrical output of the radio-frequency spectrometer, thereby producing an amplified electrical signal comprising between about 0.1 Watts and about 10 Watts power, a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter, and at least one magnet supplying an external magnetic field to a detection region of the radio-frequency detection probe, the external magnetic field being less than about 3 Tesla. Alternatively, the magnetic resonance relaxometry device can include conventional NMR spectroscopy using higher external magnetic field higher than about 3 Tesla.

This highly sensitive and targeted approach (as well as composite measurement) accurately detect and quantify the redox (and hence oxidative/nitrosative) state of blood samples. The non-destructive nature of the MRR measurement allows oxidative stress to be artificially introduced in ex vivo environment using different biochemical compounds (e.g. nitrite, peroxide, sodium salicylic) in a controlled manner to the cells (FIG. 1C). This allows functional assessment of the oxidative susceptibility, tolerance and capacity of a subject. This yields significantly richer and clinically useful information about the oxidative health of an individual, which is difficult to achieve with the routine biomarkers. A $T_1$-$T_2$ magnetic state diagram is developed to enumerate the various redox states of the Hb (e.g., $Fe^{2+}$, $Fe^{3+}$, $Fe^{4+}$, and globin-associated radical $Fe^{4+}$) and plasma (FIG. 1D). This state diagram allows visualization and identification of the intermediate redox states and the transient dynamic pathways of the blood.

Figure 1B:
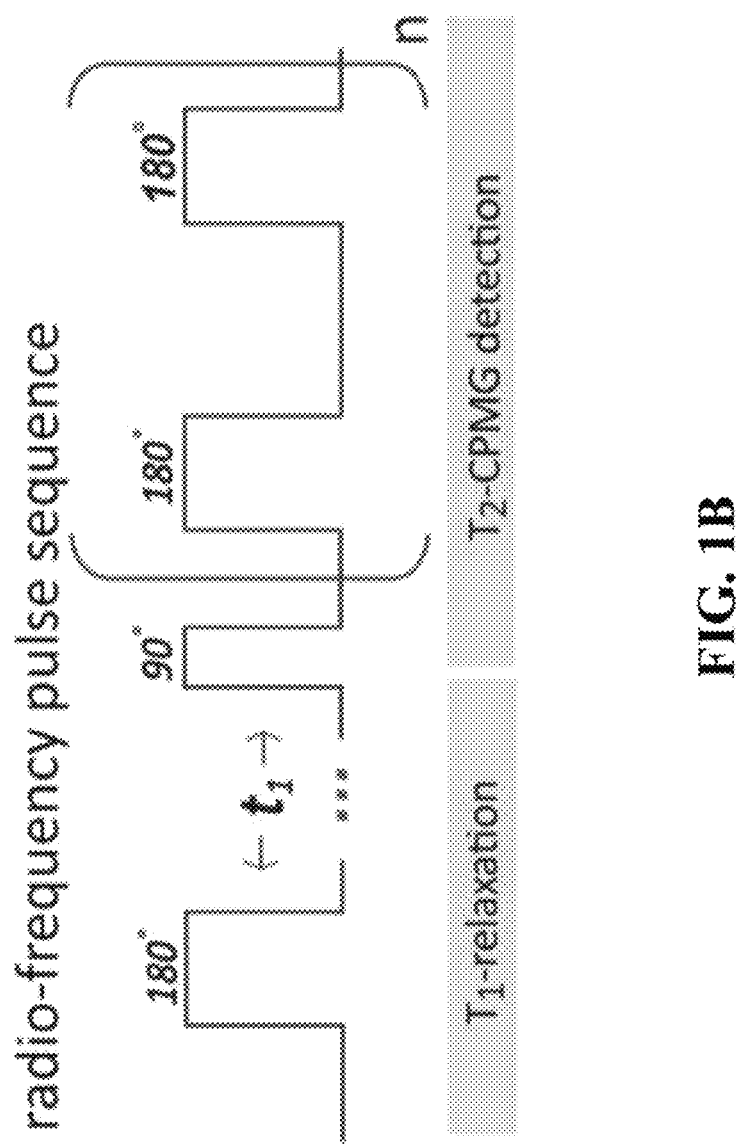
FIG. 1B shows standard inversion recovery experiment with Carr-Purcell-Meiboom-Gill (CPMG) detection is used for measuring $T_1$ relaxations. $T_2$ relaxations were measured by the same CPMG pulse without the initial 180-degree pulse.
Figure 1C:
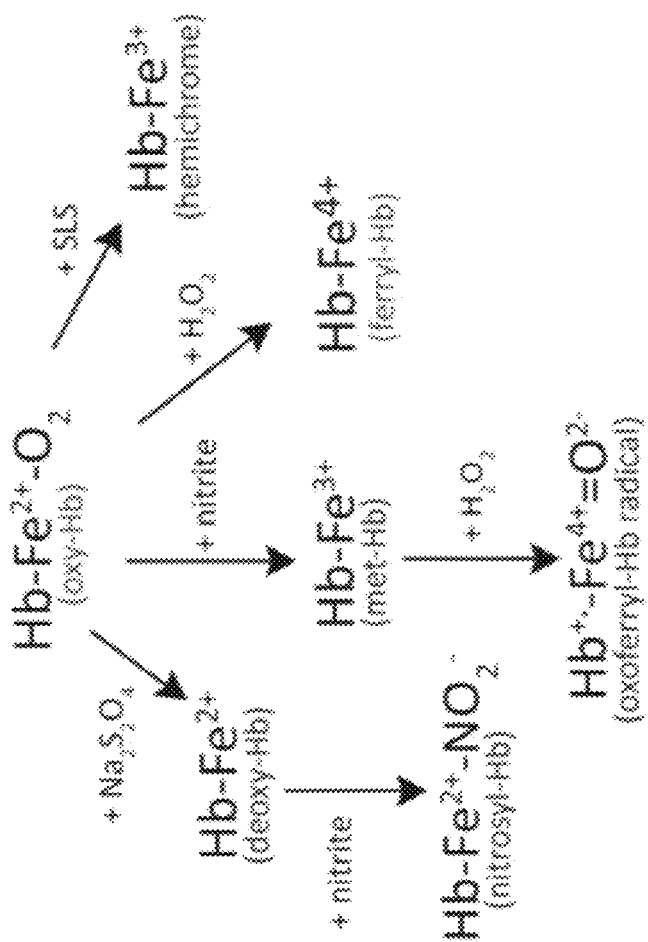
FIG. 1C shows redox reactions of the iron-heme in the in various oxidation states.
Figure 1D:
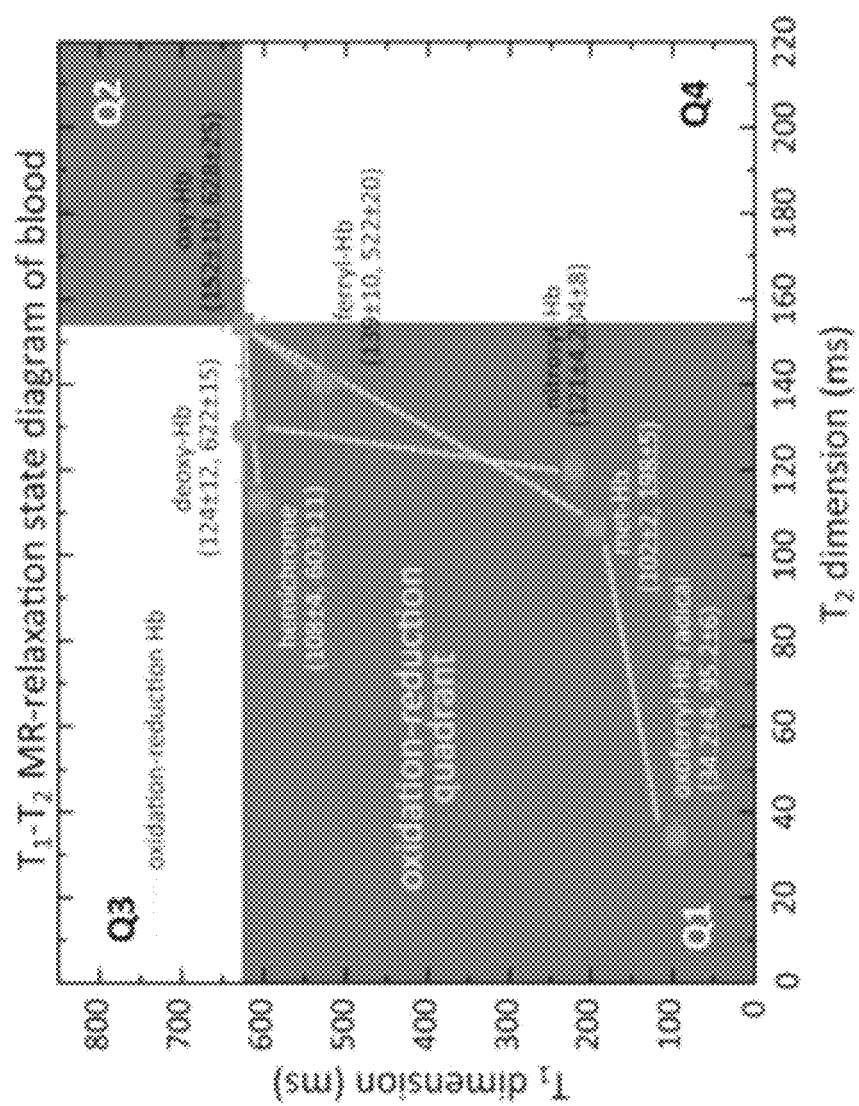
FIG. 1D shows various redox states of hemoglobin and its relative $T_1$-$T_2$ coordinates in a MR relaxation 'state diagram'.
Figure 1F:
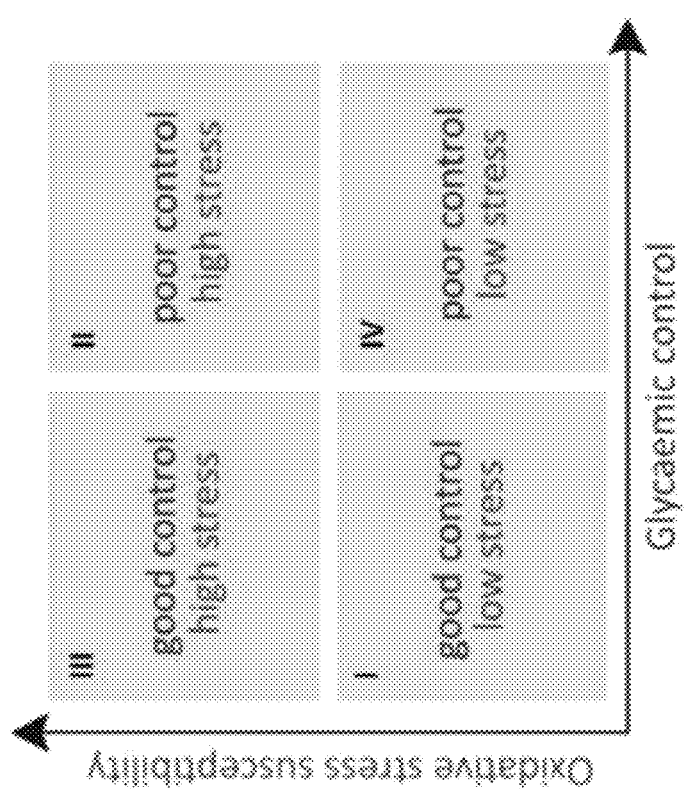
FIG. 1F shows a quadrant chart of diabetic subject stratified into subgroups based on their oxidative status in association with their glycaemic controls.

This technique was applied on archived human blood samples to stratify diabetic subjects into subgroups based on their oxidative status in association with glycaemic control (FIG. 1F). Assessment of oxidative status by measuring the redox state of the blood was shown to be highly time- and patient-specific, potentially unlocking information that is critical for clinical diagnostic, monitoring and prognostic purposes. This technology was demonstrated in a clinical setting to stratify DM (n=245) and non-DM (n=32) subjects into sub-groups based on their ONS in association with glycaemic profile. These parameters may serve as additional risk stratification tools.

This is the first disclosure of the unique magnetic resonance properties of the various hemoglobin states and a magnetic state diagram to monitor them. The measurement of redox properties in plasma/erythrocytes can provide a useful parameter for functional phenotyping of many biological pathways leading to the understanding of diseases onset/progression and hence its application to disease diagnosis, prognosis and monitoring.

The platform presented here has several innovative features and is readily adaptable into clinical use. Firstly, the miniaturized platform used here is portable and the proposed assays requires minimal processing steps, ultra low-cost and can be performed by minimally operator training. See, Vo, N., et al. Highly Integrated, Low Cost, Palm-Top Sized Magnetic Resonance Relaxometry System for Rapid Blood Screening. in *The 15th International Conference on Biomedical Engineering*, Vol. 43 558-561 (Springer International Publishing), Sun, N., et al. Palm N M R and 1-chip NMR. *Solid-State Circuits, IEEE Journal of* 46, 342-352, Peng, W. K., Chen, L. & Han, J. Development of miniaturized, portable Magnetic Resonance Relaxometry System for Point-of-Care Medical Diagnosis. *Rev Sci Instru* 83(2012), and Haun, J. B., et al. Micro-NMR for rapid molecular analysis of human tumor samples. *Science Translational Medicine* 3, 71ra16, each of which is incorporated by reference in its entirety. The high sensitivity can be attributed to the micron-sized detection coil and optimized ultra-short echo time implemented in this work. Only a minute amount of blood sample volume (<10-20 µL) is needed for each test. This allows the collection of sample using minimally invasive technique such as finger prick.

Secondly, the non-destructive nature of magnetic resonance introduced a number of in-vitro new functional assays that yielded parameters about the oxidative status of an individual, which may be clinically useful. It probes the primary redox event as compared to the current gold-standard biomarker, isoprostanes, which is a downstream marker and with other confounding factors. The use of isoprostanes as biomarker of oxidative status for correlation with disease outcome has so far yielded conflicting results in cross-sectional versus longitudinal studies. See, Lee, R., Margaritis, M., Channon, K. & Antoniades, C. Evaluating oxidative stress in human cardiovascular disease: methodological aspects and considerations. *Current medicinal chemistry* 19, 2504 (2012), which is incorporated by reference in its entirety. Furthermore, they are static biomarkers that provide snapshots of the oxidative status of biological samples representing the in vivo condition of the subject at the point of collection. To accurately measure these molecules, laborious technique such as gas- or liquid-chromatography mass spectrometry has to be employed, limiting its utility as diagnostic tools.

This accurate and rapid technique for quantification of oxidative stress can be included in future risk stratification models where subjects with single or multiple complications can be streamlined with a single oxidative index. This method can be applied to assess oxidative stress in a systematic manner for various diseases and a wide range of hematology applications, both the acquired and congenital diseases such as enzymatic deficiency (e.g., G6PD), Hb synthesis defects (e.g., Thalassemia), and Hb molecular defects (e.g., sickle cells anemia, unstable Hb).

EXAMPLES $T_1$-$T_2$ State-Diagram: Redox States of Blood

Redox homeostasis is a fundamental biological process, which maintains the balance between ambient anti-oxidant and pro-oxidant activities. See, Cimen, M. Y. Free radical metabolism in human erythrocytes. *Clin. Chim. Acta* 390, 1-11 (2008), which is incorporated by reference in its entirety. Blood, in particular the iron-containing heme, which has partially filled d-orbital shells (and hence allows the formation of various redox states) that act as an electron reservoir (see, Jomova, K. & Valko, M. Advances in metal-induced oxidative stress and human disease. *Toxicology* 283, 65-87, and Hartwig, A. Recent advances in metal carcinogenicity. *Pure Appl. Chem.* 72, 1007-1014 (2000), each of which is incorporated by reference in its entirety), is an important biological agent in ameliorating oxidative stress. On the other hand, oxidized Hb themselves can act as sources of electrons contributing to oxidant built-up.

FIG. 1A shows schematic illustration of the MRR assays. Once the patient's blood is collected via venipuncture or finger prick, necessary biochemical assay is performed in blood aliquots. Chemical reagent (e.g., nitrite, peroxide, acid salicylic) is mixed with the fresh blood and incubated for intervals 10 minutes (unless mentioned otherwise) in selected concentration. Microcapillary tubes were then used to sample the redox state of the packed RBCs/plasma. Standard centrifugal force (3000 g, 1 minute) was used to separate and concentrate the packed RBCs from the buffer to avoid possible hematocrit variation in patients. The capillary tubes were then slotted into the rf-probe for MRR read-out, which typically requires less than 5 minutes. The portable micro MRR system developed in this work consists of a bench-top console, detection circuit-coil mounted on a micro-stage and a palm-sized 0.5 T permanent magnet, which is maintained in a temperature controller to maintain the magnetic stability.

FIG. 1B shows standard inversion recovery experiment with CPMG detection is used for measuring $T_1$ relaxations. $T_2$ relaxations were measured by the same CPMG pulse without the initial 180-degree pulse. In order to obtain high signal-to-noise ratio under strongly inhomogeneous magnetic environment, an array of echoes (a few thousands) within a very short echo interval (in the order of μs) were used to acquires spin-echoes from in less than 4 μL sample volume of packed RBCs or plasma.

FIG. 1C shows redox reactions of the iron-heme in the in various oxidation states: $Fe^{2+}$, $Fe^{3+}$, $Fe^{4+}$ and globin-radical $Fe^{4+}$, which were chemically-induced in in-vitro environment. The haemoglobins were in two-possible magnetic states: diamagnetic (red) and paramagnetic state (blue).

FIG. 1D shows various redox states of hemoglobin and its relative $T_1$-$T_2$ coordinates in a MR relaxation 'state diagram'. The coordinates were oxy-Hb ($T_2$=152±10, $T_1$=628±25), deoxy-Hb ($T_2$=124±12, $T_1$=622±15), met-Hb ($T_2$=102±2, $T_1$=198±5), ferryl-Hb ($T_2$=139±10, $T_1$=522±20), oxoferryl-Hb ($T_2$=34.2±4, $T_1$=95.2±6), nitrosyl-Hb ($T_2$=121±4, $T_1$=204±8), and hemichrome ($T_2$=108±4, $T_1$=603±11). The corresponding magnetic states, number of unpaired electron, A-ratio, and iron oxidation state in shown in Table in FIG. 1E.

FIG. 1F shows a quadrant chart of diabetic subject stratified into subgroups based on their oxidative status in association with their glycaemic controls Here, various redox states of the blood were chemically induced (FIG. 1C), characterized and represented in a $T_1$-$T_2$ magnetic resonance relaxation state diagram (FIG. 1D). Each hemoglobin species has specific oxidation states (e.g., $Fe^{2+}$, $Fe^{3+}$, $Fe^{4+}$, globin-associated radical of $Fe^{4+}$ or its' corresponding complexes) that are bound to specific neighboring proteins, and dissipate energy via unique relaxations mechanism in both the longitudinal ($T_1$) and transverse ($T_2$) relaxation frames. This creates a unique pair of $T_1$-$T_2$ relaxometry coordinates for each redox species. Oxyhemoglobin (oxy-Hb), which contains the lowest reduced ferrous ($Fe^{2+}$) state, is the predominant Hb species in circulation. It is assigned the origin (center) coordinate, which divide the MR state diagram into four quadrants. Most of the redox reactions of the hemoglobin occur in quadrant-1 (short relaxation times in the order of ms) and is mainly due to the semi-solid structure of RBCs. By contrast, the redox reaction of plasma albumin, which involves unbound water-proton, has a much longer relaxation time and occurs in quadrant-2. The electrons in the d sub-orbitals of iron in hemoglobin can exist in various paired or unpaired states, allowing them to exist in diamagnetic and paramagnetic states, respectively. Hb with at least one unpaired electron, i.e. deoxygenated hemoglobin (deoxy-Hb), methemoglobin (met-Hb), hemichrome (HC), nitrosyl hemoglobin (nitrosyl-Hb), and oxo-ferryl radical exhibit paramagnetism and has much larger bulk magnetic susceptibility than its diamagnetic counterparts (oxy-Hb, and ferryl-Hb) (FIGS. 1D and 1E). The magnetic relaxivity contributed by any paramagnetic ion is highly dependent on its spin state, and is directly proportional to S(S+1), where S is the spin quantum number of the total electron spin. Each of the Hb oxidation states has a specific normalized relaxation constant (A-ratio=$T_1$/$T_2$) identifier (FIG. 1E).

Nitrite-Induced Ferrous Oxidation

Figure 2A:
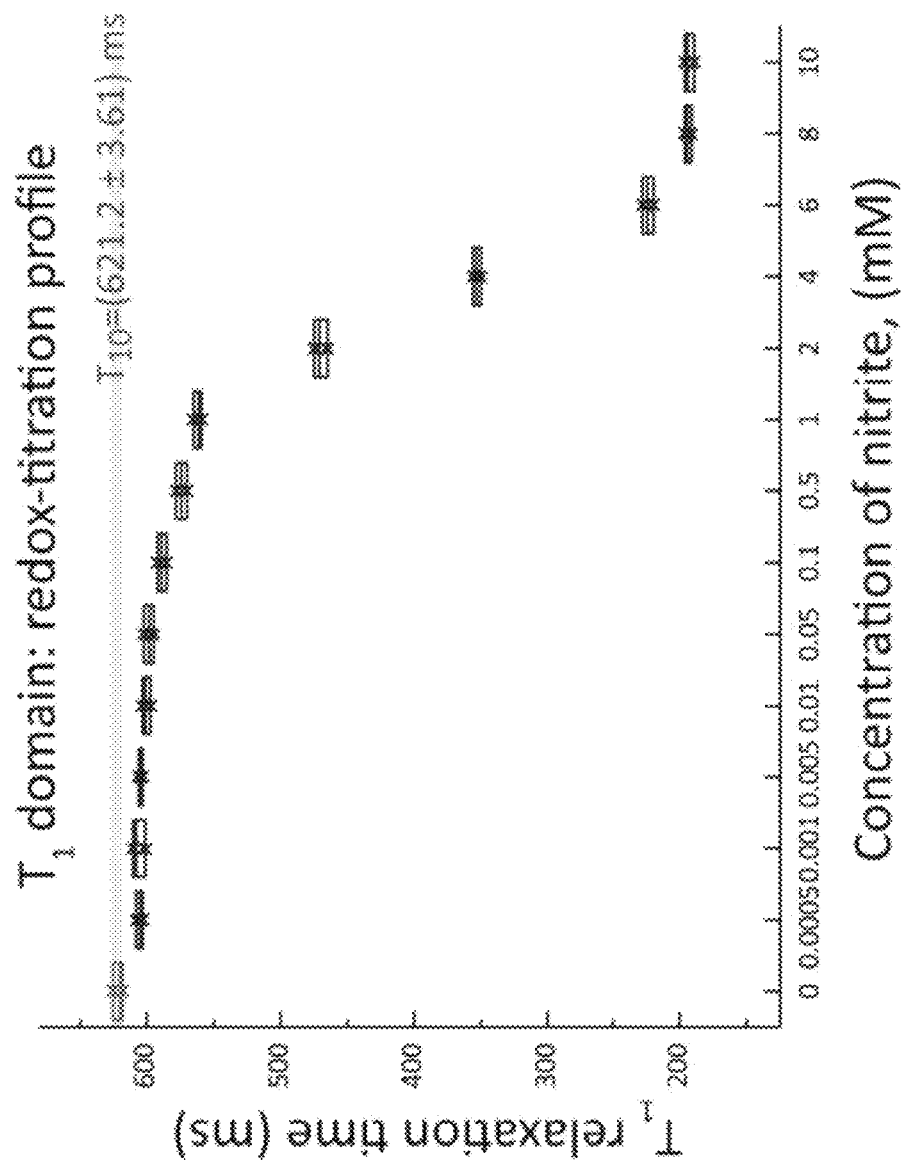
FIGS. 2A-2H show nitrite induced ferrous oxidation: redox-titration profile of red blood cells as function of nitrite concentrations in $T_1$ (FIG. 2A) and $T_2$ (FIG. 2B) domains. The corresponding concentrations dependent A-ratio (FIG. 2C), and $T_1$-$T_2$ trajectories (FIG. 2D) of the gradual inversion of $Fe^{2+}$ sub-populations to complete formation of $Fe^{3+}$ populations. Time-dependent kinetic profile of ferrous oxidation for nitrite concentrations in (e) $T_1$ (FIG. 2E) and $T_2$ (FIG. 2F) domains.
Figure 2B:
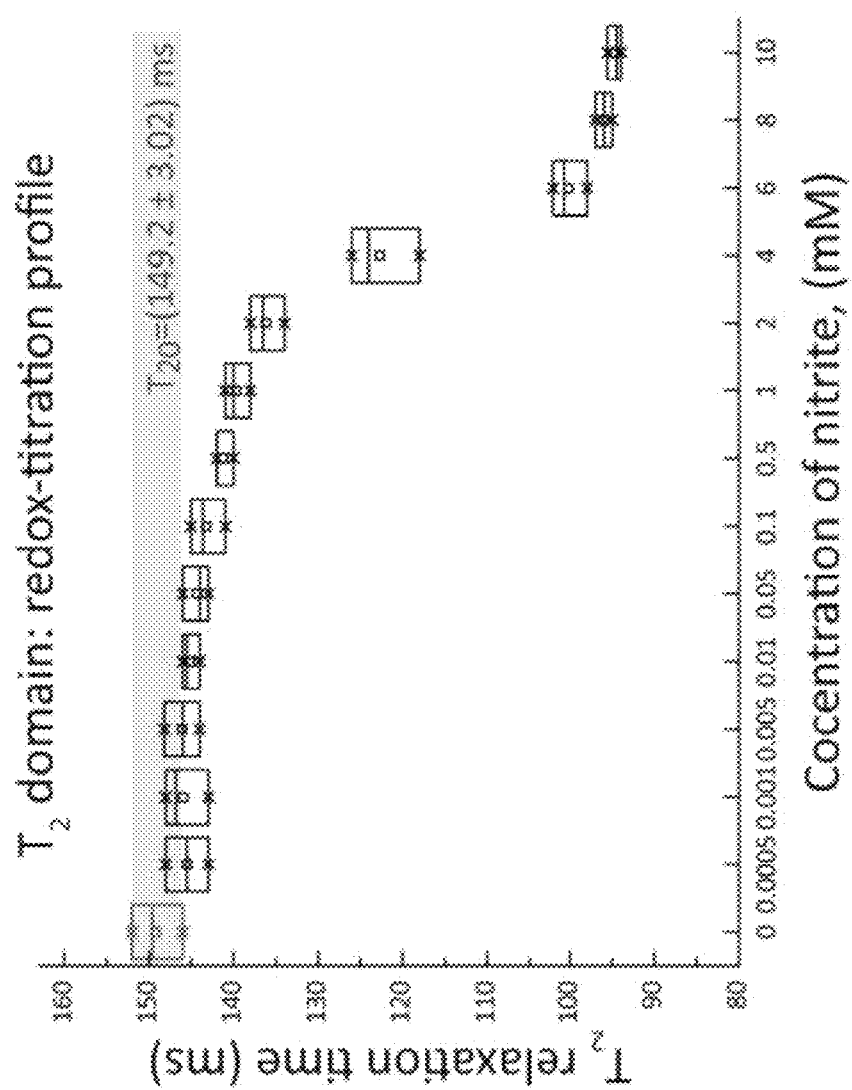
Figure 2C:
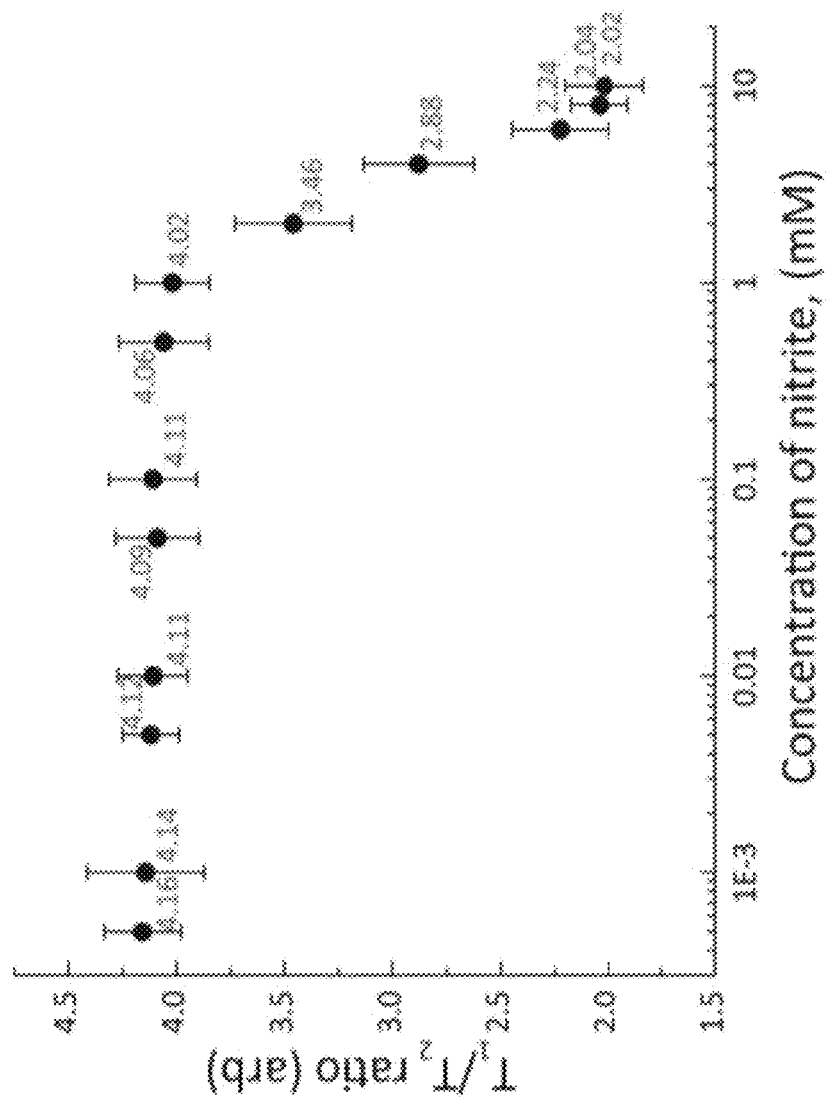
Figure 2D:
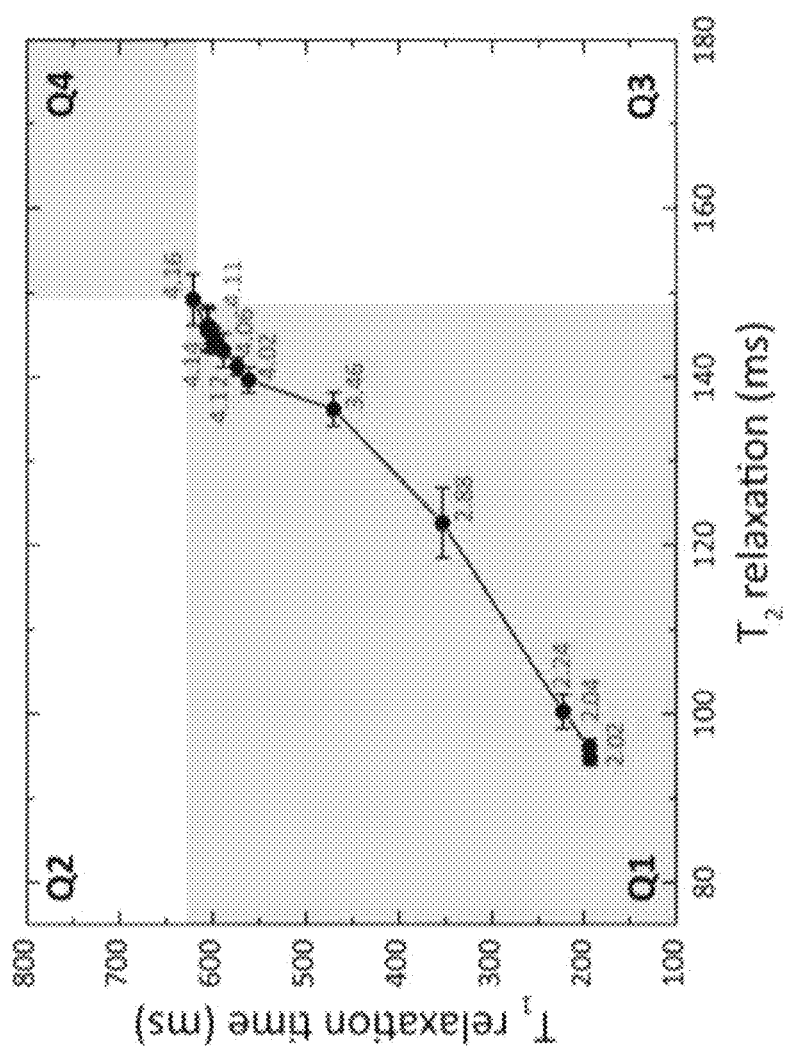
Figure 2E:
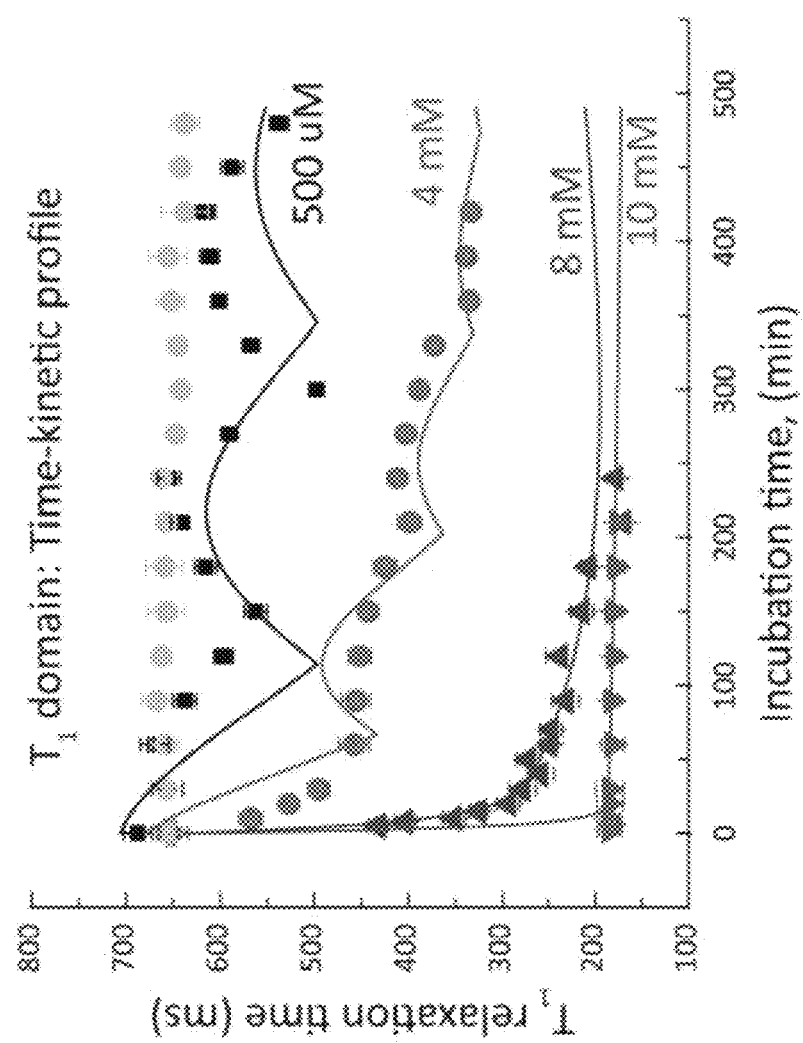
Figure 2F:
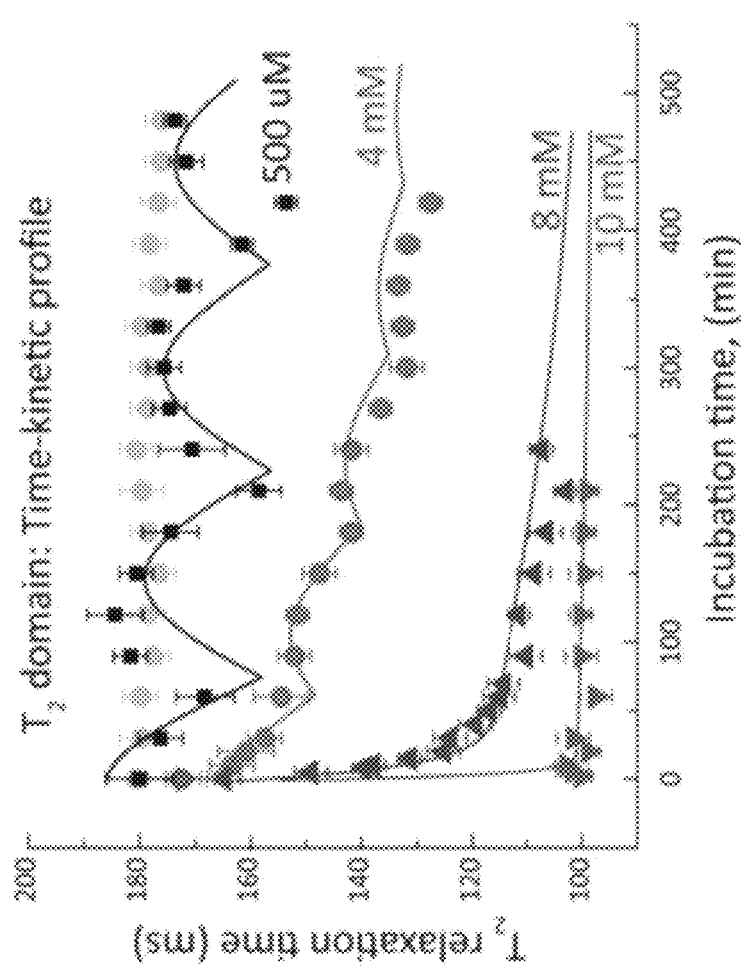

FIGS. 2A-H show nitrite induced ferrous oxidation: Redox-titration profile of red blood cells as function of nitrite concentrations in $T_1$ (FIG. 2A) and $T_2$ (FIG. 2B) domains. The incubation times were 10 minutes. The control baseline reading were ($T_{20}$=149.5, $T_{10}$=621.3) ms, which is the readings for oxy-Hb without any nitrite exposure. The corresponding concentrations dependent A-ratio (FIG. 2C), and $T_1$-$T_2$ trajectories (FIG. 2D) of the gradual inversion of $Fe^{2+}$ sub-populations to complete formation of $Fe^{3+}$ populations. Time-dependent kinetic profile of ferrous oxidation for nitrite concentrations (500 μM, 4 mM, 8 mM and 10 mM) in $T_1$ (FIG. 2E) and $T_2$ domains (FIG. 2F). The corresponding time-dependent A-ratio (FIG. 2C), and $T_1$-$T_2$ trajectories (FIG. 2D) in the state diagram. The readings were indicated in mean and standard mean error (s.e.m) from three samplings.

Freshly collected blood containing predominantly the oxygenated Hb are oxidized in-vitro to met-Hb in the presence of sodium nitrite, and were independently verified by spectrophotometry (FIG. 7). Redox titration profile showed a strong dose-dependent curve where both $T_1$ and $T_2$ relaxation times reduced gradually as progressively higher proportion of RBCs is oxidized and hence increases the volume paramagnetic susceptibility, when the nitrite concentrations were increased from 50 nM to 10 mM (FIGS. 2A and 2B). As the blood sample transformed to a complete paramagnetic state ($T_2$=92.8 ms, $T_1$=190.0 ms) from the initial diamagnetic states ($T_2$=149.0 ms, $T_1$=620.0 ms), the A-ratio dropped from 4.16 to 2.02 (FIG. 2C). This causes the $T_1$-$T_2$ trajectory to move in quadrant-1 as the volume paramagnetic susceptibility increased (FIG. 2D).

The dose-dependent reaction was lost when excess of nitrite (>10 mM) was introduced. This indicated that the oxidant concentration had exceeded the biochemical homeostasis mechanism. At much lower concentration (<100 there was little or no change in the bulk magnetic state of the RBCs, as the majority of the RBCs were able to restore their original reduced state. Interestingly, steep transitional oxidation zone was observed within a very narrow range of nitrite concentration; from 1 mM to 8 mM, which reflected the redox homeostatic responses within the concentration where the cells were viable. This was crucial to the understanding of the functioning of RBCs at cellular and subpopulation level (FIGS. 2A-2C). Similar trends were observed in subjects of different age and gender, which provided an understanding of the degree of inter-individual variability (FIGS. 10A-D).

Further evidence of redox homeostasis were observed in time-dependent kinetic profiles (FIGS. 2E-2F) over a range of nitrite concentrations (500 µM, 4 mM, 8 mM and 10 mM). In general, measured $T_1$ and $T_2$ values changed in an oscillatory manner over time. This may suggests an active mechanism to regulate cell redox homeostasis. The alpha-Hb are known to have much higher oxidative susceptibility than beta-Hb. Furthermore, the RBCs may have reduced antioxidant capacity as they age, thereby forming a subpopulation of cell with disproportionately low antioxidant capacity. See, Bernhardt, I. & Ellory, J. Red cell membrane transport in health and disease. (2003), which is incorporated by reference in its entirety.

Figure 2G:
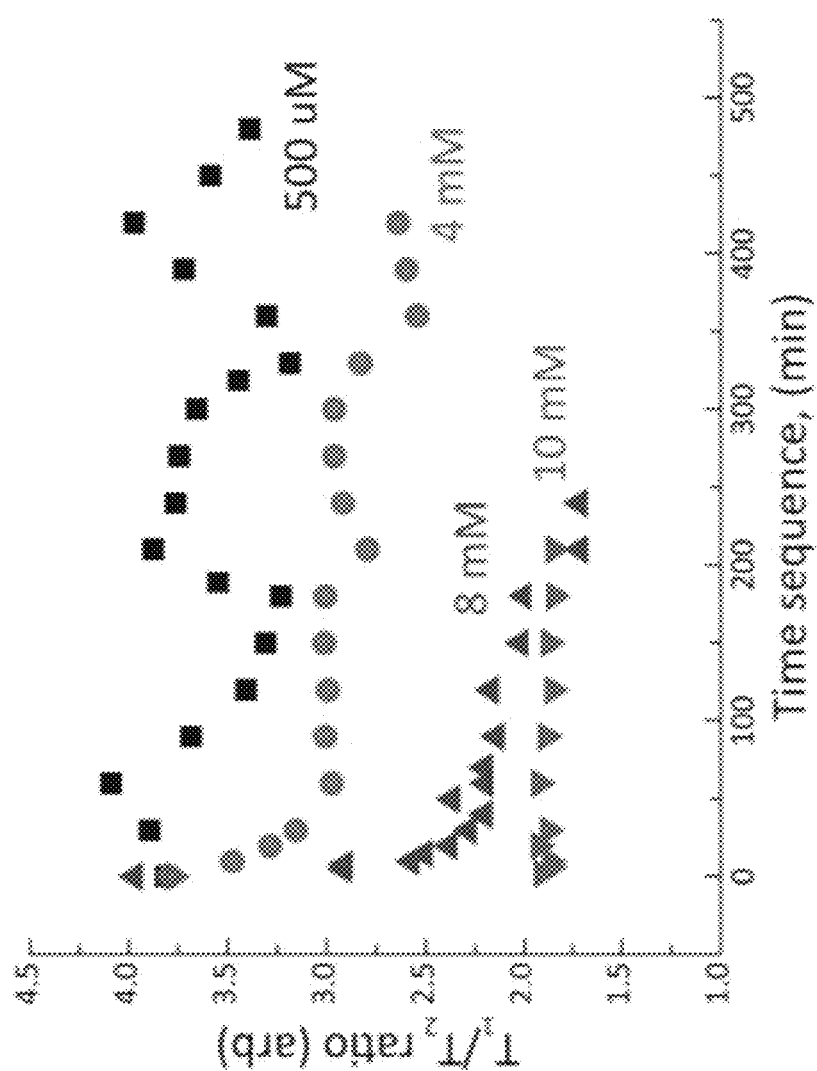
Figure 2H:
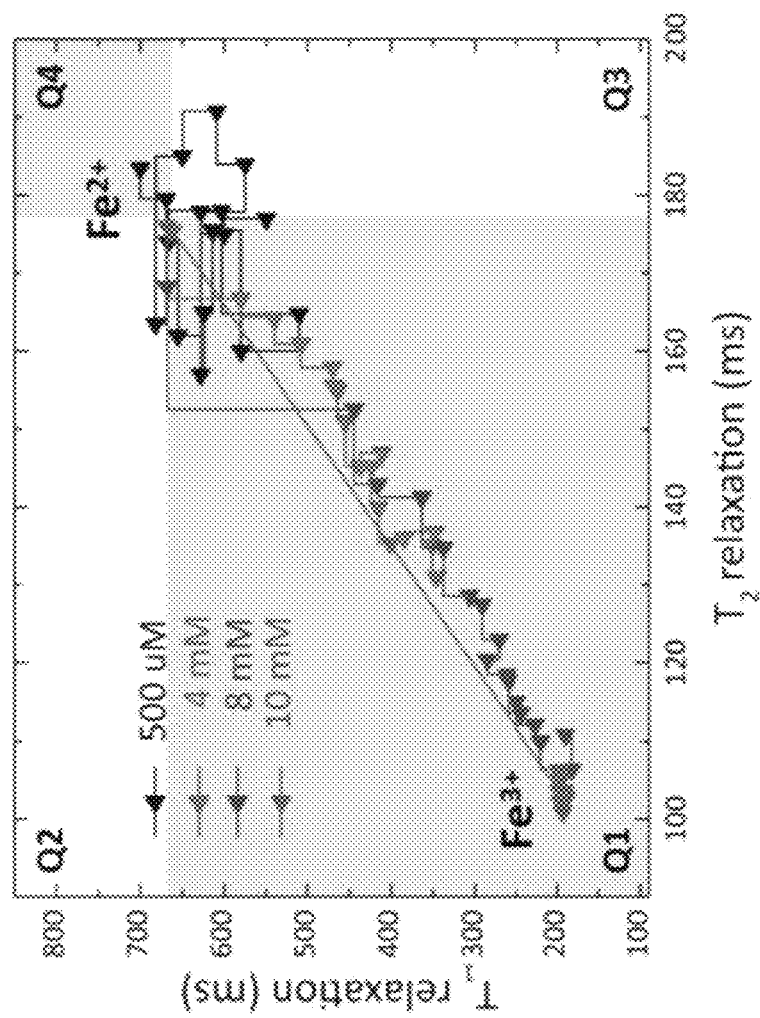

The amplitudes of the oscillation decreased as the nitrite concentration was increased from 500 µM to 4 mM (FIG. 2G). At much higher nitrite concentration (>10 mM), the reaction curve decayed rapidly in exponential manner with an increasingly dampened oscillation. Interestingly, the corresponding kinetic profiles followed an identical path over time in the $T_1$-$T_2$ trajectories as the nitrite concentration was increased (FIG. 2H). The oxidation process drove all the trajectories toward a common coordinate ($T_2$=92.8 ms, $T_1$=190.0 ms), where full met-Hb conversion was achieved eventually. For low nitrite concentration (e.g., 500 µM) however, the $T_1$-$T_2$ trajectory circulated around the origin and did not reach the eventual met-Hb coordinates at the time intervals shown in this work.

Deep Phenotyping of Nitrosative/Oxidative Stress in Diabetes Mellitus Subjects

A cross-sectional study was carried out to further stratify DM subjects based on their oxidative status. DM subjects (n=426) who had $HbA_{1c}$ measured in the outpatient clinic as part of their clinical care were included in this study. These subjects have $HbA_{1c}$ ranged from 4% to 16%, which were classified as good glycaemic control (<7.0% $HbA_{1c}$) and poor glycaemic control (>8.0% $HbA_{1c}$) sub-groups based on the criteria set by WHO. Healthy young male subjects (n=35) between 21 to 40 years subjects with no past history of DM with fasting glucose <7.0 mmol/L, and (5.16±0.32) % of $HbA_{1c}$, with the body mass index below 23.5 kg/m² were recruited as controls. Freshly drawn blood obtained via venipuncture was spun down to separate the RBCs and plasma. MRR measurements on the hemoglobin and plasma (both the baseline and biochemical stress test) were performed blindly on freshly collected blood (or otherwise stored under 4° C. within 1-2 hours). Other hematology tests were carried out in parallel.

Baseline Study: Oxidative Status of Glycated Hb and Hb in RBCs

Figure 3A:
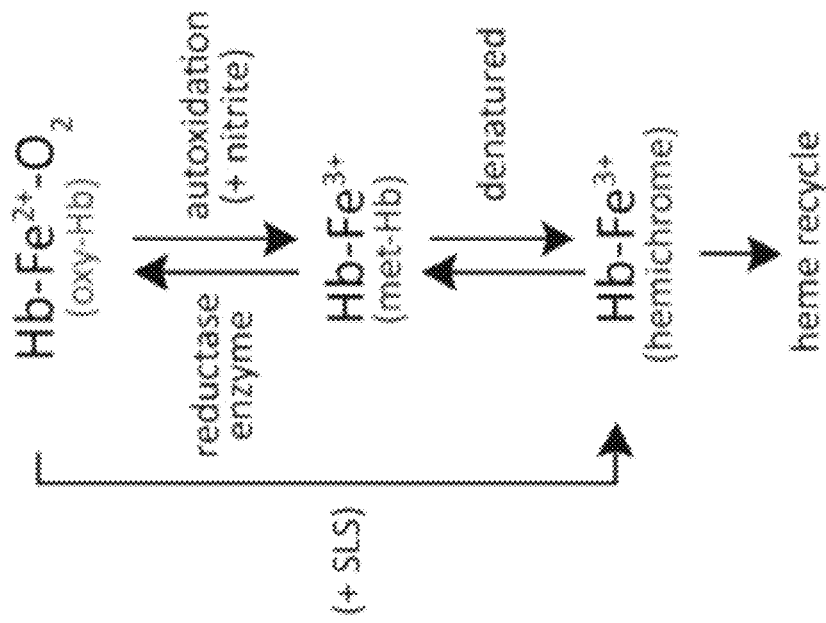
FIG. 3A shows in-vivo redox formation of high-spin met-Hb, low-spin hemichrome and heme metabolism. The equivalent chemically-induced in-vitro environment (in brackets).
Figure 3B:
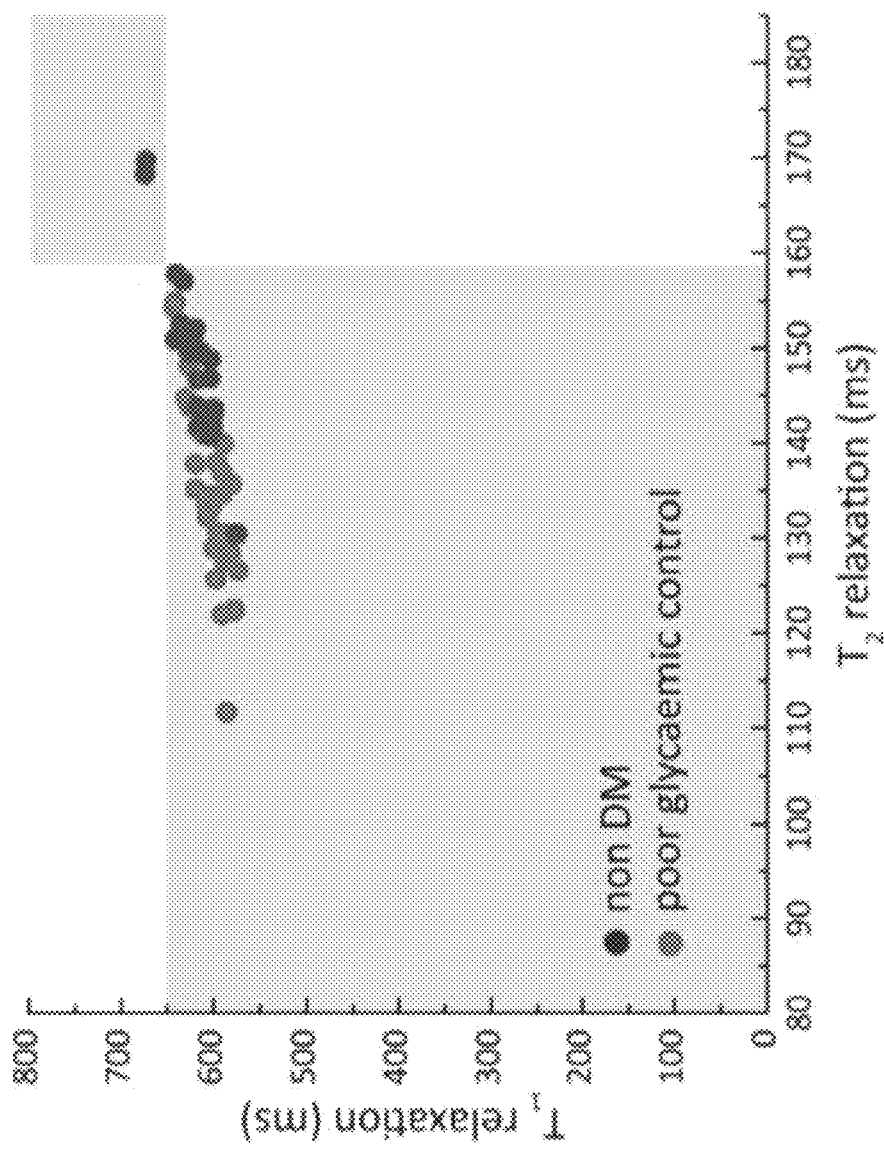
FIG. 3B shows the corresponding $T_1$-$T_2$ trajectories of chemically-induced to form met-Hb and hemichrome, respectively.
Figure 3C:
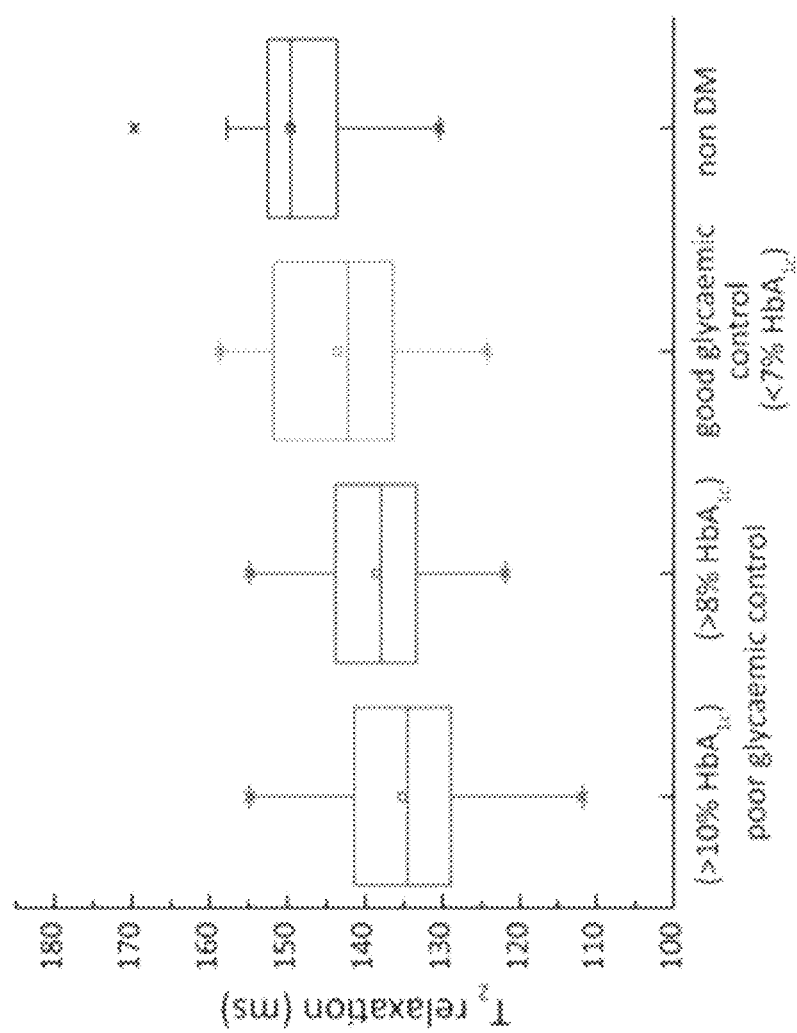
FIG. 3C shows RBCs baseline readings of non-DM subjects and poor glycaemic control subject for $T_2$ domain.
Figure 3D:
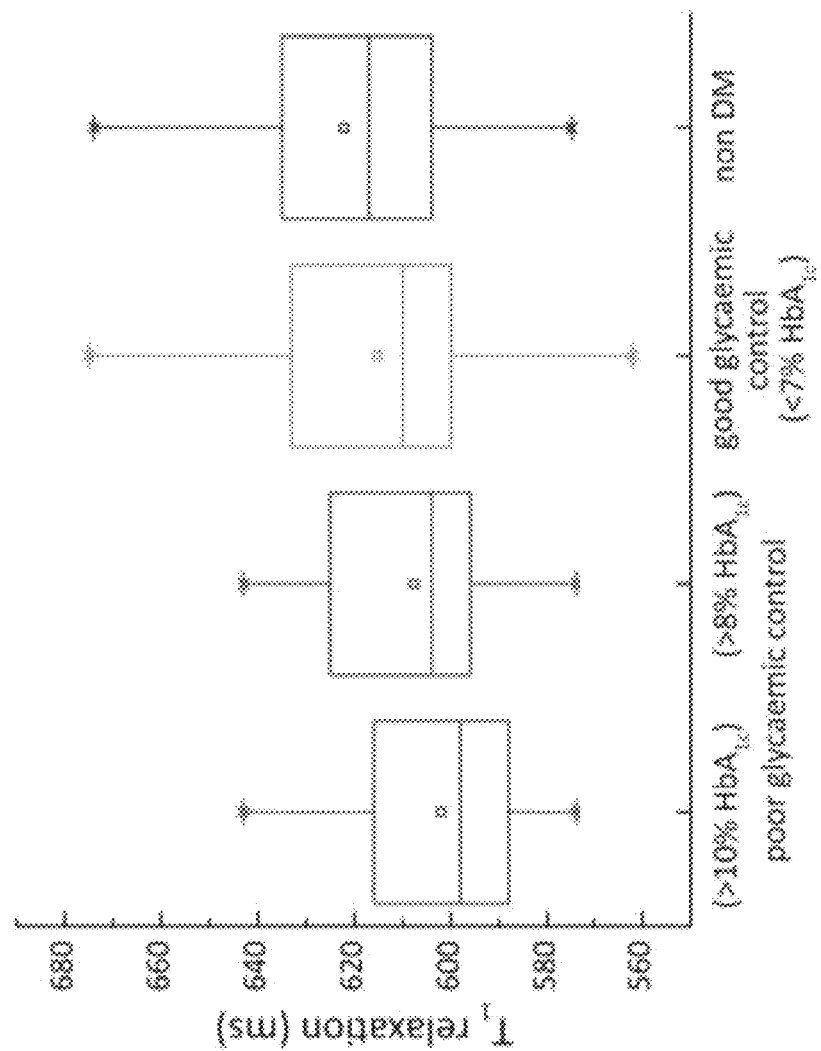
FIG. 3D shows RBCs baseline readings of non-DM subjects and poor glycaemic control subject for $T_1$ domain.

FIG. 3A shows in-vivo redox formation of high-spin met-Hb, low-spin hemichrome and heme metabolism. The equivalent chemically-induced in-vitro environment (in brackets). FIG. 3B shows the corresponding $T_1$-$T_2$ trajectories of chemically-induced with 10 mM nitrite and 0.15M SLS, to form met-Hb and hemichrome, respectively. The parenthesis indicating the relatives coordinates ($T_2$, $T_1$, A-ratio). FIGS. 3C and 3D show RBCs baseline readings of non-DM subjects (blue, n=23) and poor glycaemic control subjects (red, n=68) for $T_2$ and T1 domains, respectively. Each single point represents the MRR reading of one subject. The breakdown details of poor (>8% and >10% $HbA_{1c}$) and good glycaemic control (<7% $hbA_{1c}$) subgroups as opposed to non-DM subjects in $T_2$ (FIG. 3C) and $T_1$ (FIG. 3D) domains.

Mapped baseline of hemoglobin in intact red blood cells in $T_1$-$T_2$ state diagram showed an elevation in met-Hb and HC concentration are more common in subjects with poor glycaemic control compared with non-DM subjects (FIG. 3A). DM subjects with good glycaemic control had slightly elevated $T_2$ values (p-value <0.05), but difference in $T_1$ value was not statistically significant (p>0.05) compared with non-DM subjects (FIG. 3B-3D). Non-DM subjects had met-Hb concentrations that were less than 2% (FIGS. 2D and 9). Ferric-Hb concentration was markedly elevated in DM subjects with poor glycaemic control, particularly in subjects with $HbA_{1c}$ of concentration >10% (FIGS. 3B-3D and 10).

Ex-Vivo Nitrosative Stress Test on Glycated-Hb

Figure 11A:
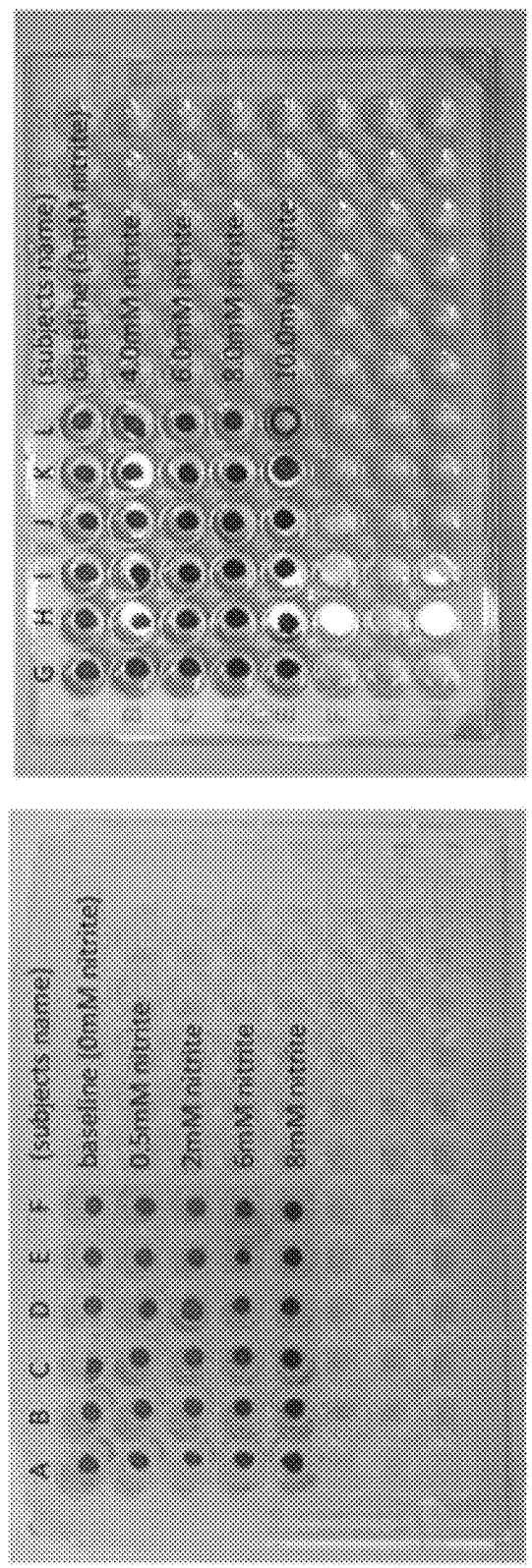
Figure 11B:
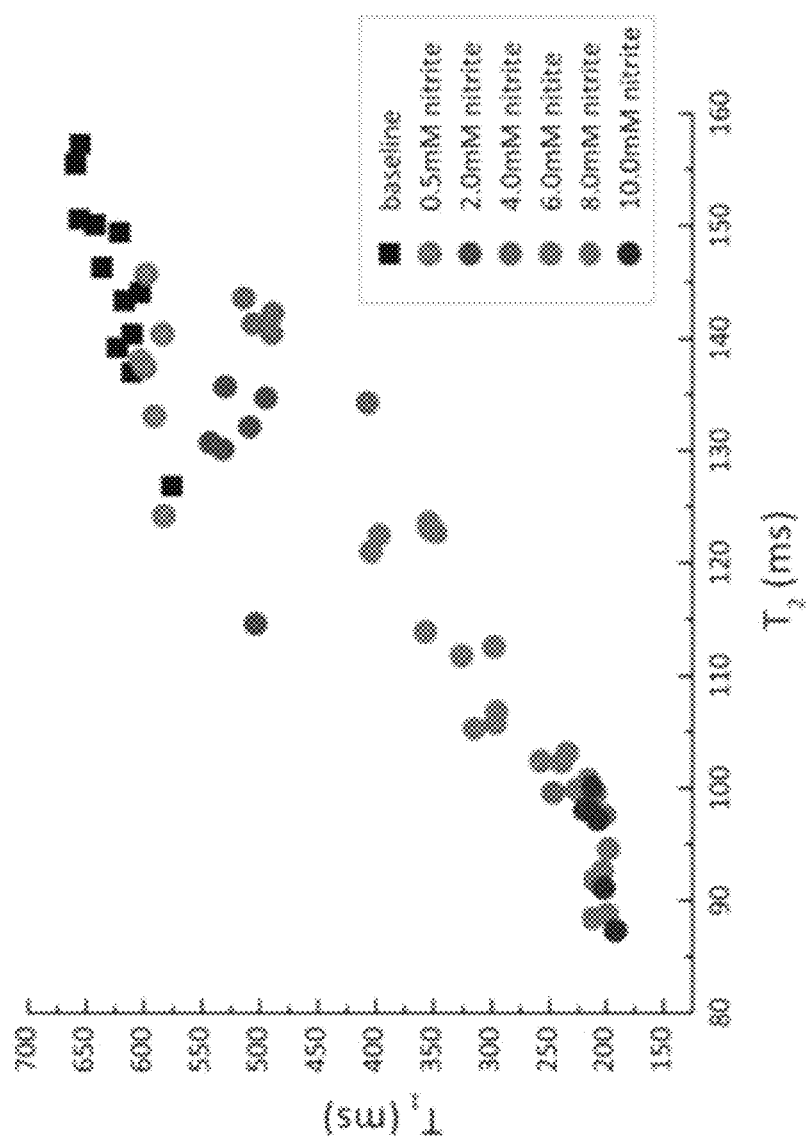

To further evaluate the ability of individual's RBCs to tolerate the nitrosative stress, the RBCs were artificially challenged with nitrite. Fresh RBCs were incubated with 6 mM sodium nitrite for 10 min, washed three times to stop the reaction and finally resuspended in 1×PBS for MRR measurements. The oxidant concentration chosen was the viable homeostatic range unique to each individual depending of his or her (patho)physiological condition (FIGS. 11-13). MRR measurements were assessed before (square) and after (circle) the stress test.

Figure 4A:
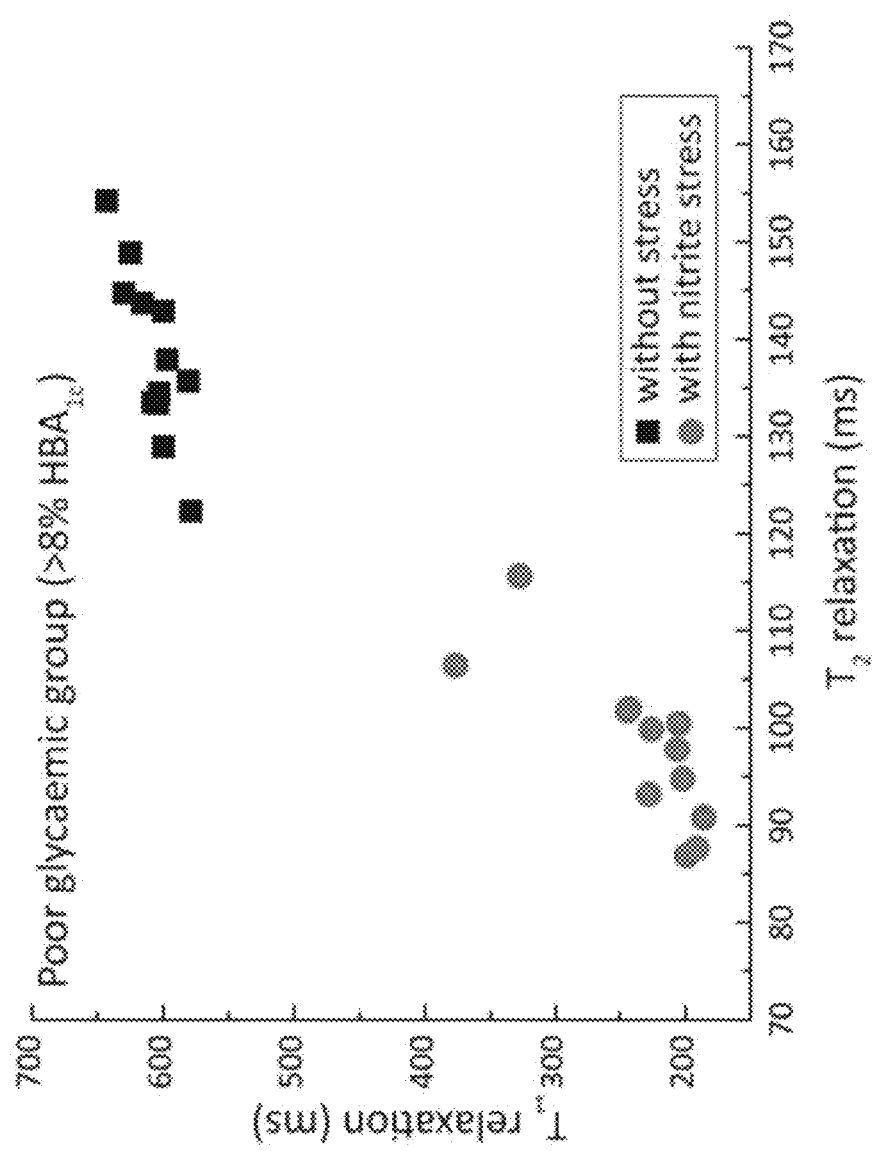
FIGS. 4A-4E show the $T_1$-$T_2$ coordinates of MRR measured of Hb before (square) and after (round) nitrite treatment for both the poor (FIG. 4A), and good glycaemic control (FIG. 4B) subjects. Each single point represents the MRR reading of one subject.
Figure 4B:
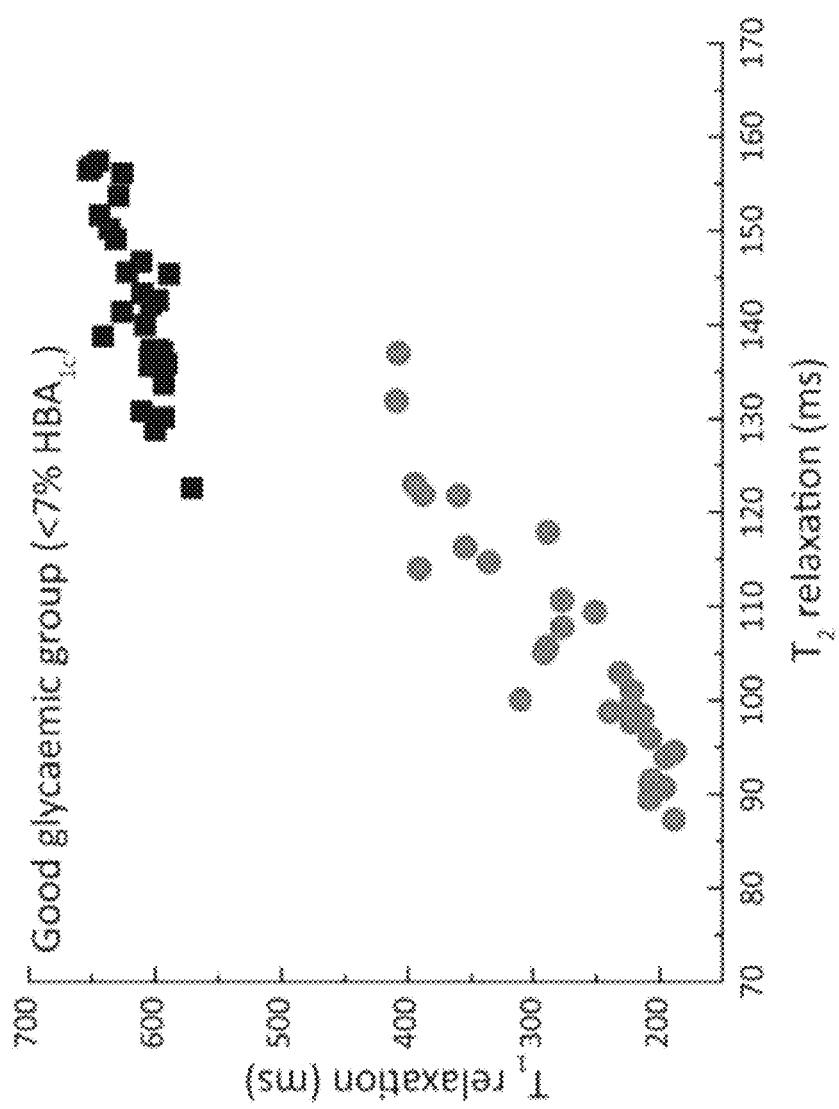
Figure 4C:
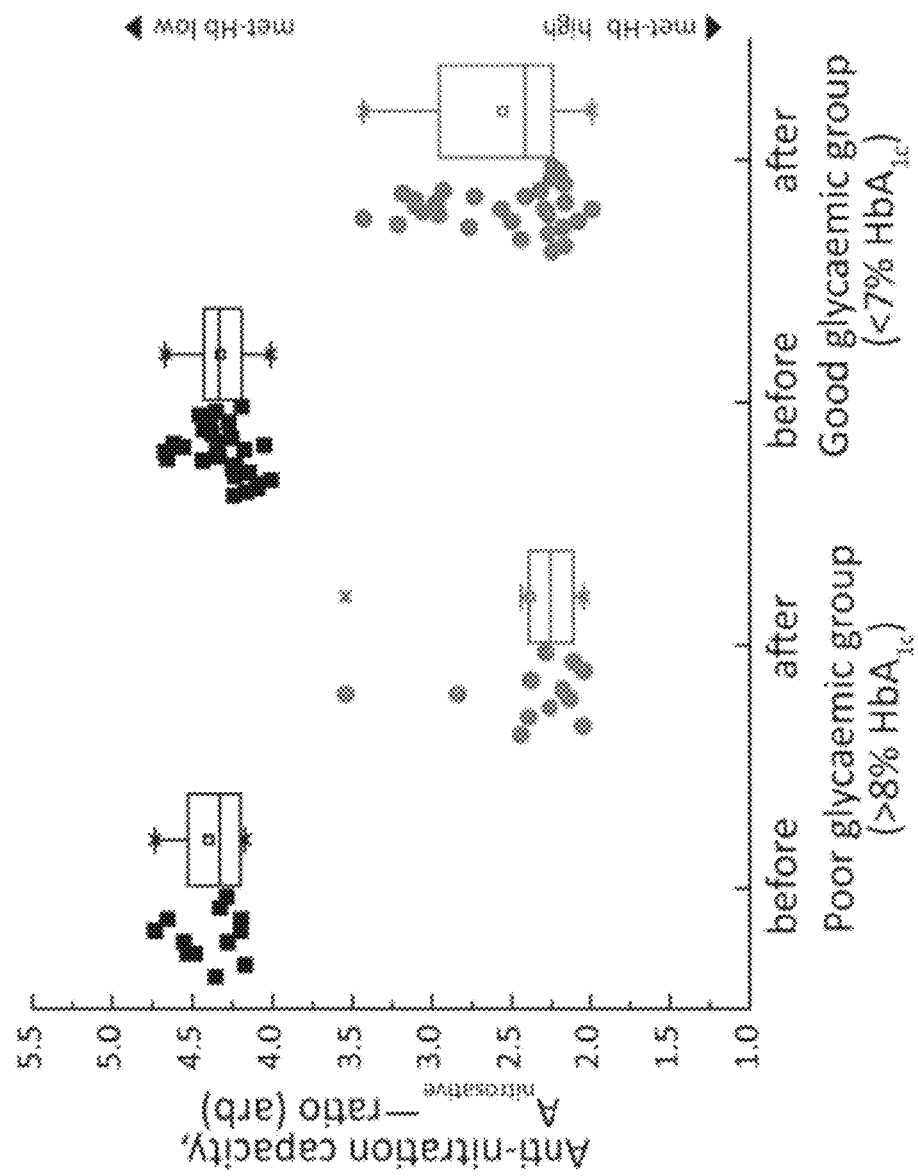

DM subjects with poor (n=12) and good (n=29) glycaemic control group with similar matching RBCs baseline (squares in FIGS. 4A-4B) were chosen for this test. Lower anti-nitration capacity (or increased in nitrosative stress susceptibility) was indicated by an increase in met-Hb formation (circles) and hence the lower the $A_{nitrosative}$-ratio value (FIGS. 2A-H). FIGS. 4A-E show the $T_1$-$T_2$ coordinates of MRR measured of Hb before (square) and after (round) 6 mM nitrite treatment for both the poor (FIG. 4A) and good glycaemic control (FIG. 4B) subjects. Each single point represents the MRR reading of one subject. FIG. 4C shows the corresponding statistical distribution based on A-ratio index for both FIG. 4A and FIG. 4B.

Figure 4D:
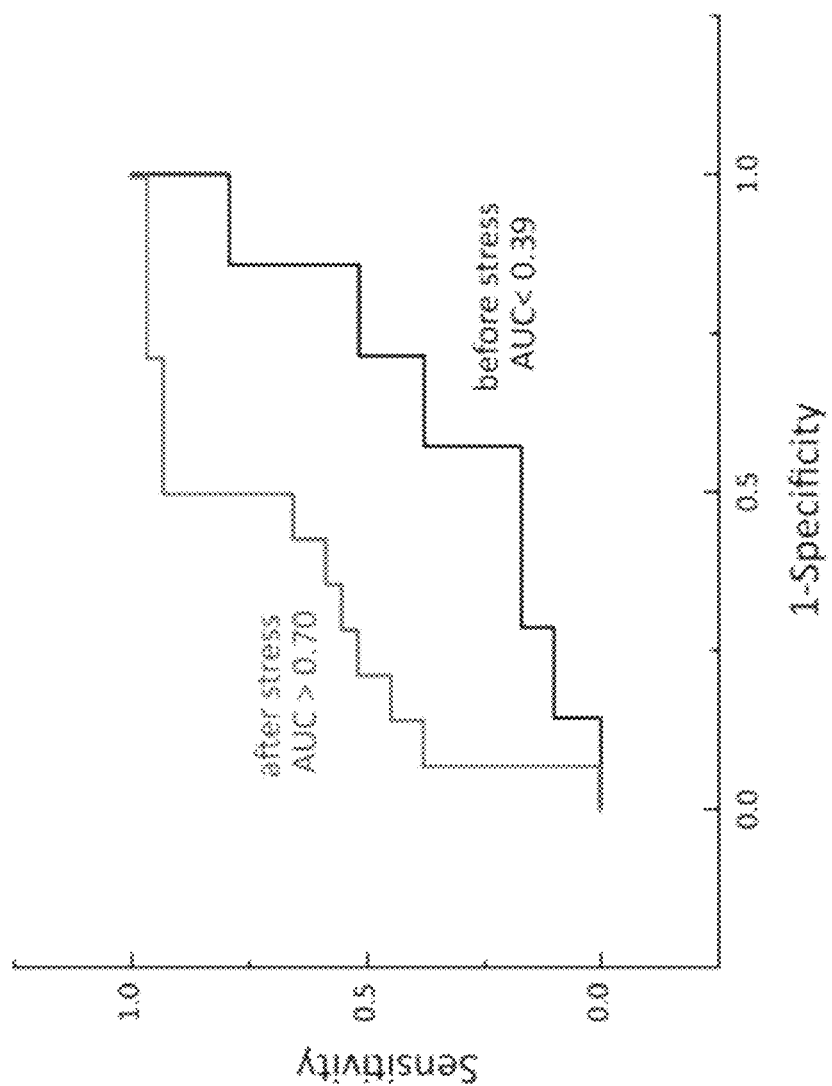

DM subjects vary markedly in their nitrosative susceptibility despite having similar matching baseline; with DM subjects of poor glycaemic control being more susceptible to nitrite-induced oxidation as compared to its counterpart with good glycaemic control (FIG. 4C). Receiver Operating Characteristic (ROC) analysis showed that the initial matching baseline (AUC <0.39) between the subjects from poor and good glycaemic group had increased (AUC>0.70) upon nitrite stress (FIG. 4D). Due to structural modification of hemoglobin as a result of increased glycation, $HbA_{1c}$ is less stable and more prone to oxidation, in agreement with observation reported elsewhere. See, Moussa, S. Oxidative stress in diabetes mellitus. *Romanian J Biophys* 18, 225-236 (2008), and Tarburton, J. Amyl Nitrite Induced Hemoglobin Oxidation Studies in Diabetics and Non-diabetics Blood. *J Diabetes Metab* 4, 2 (2013), each of which is incorporated by reference in its entirety.

Figure 4E:
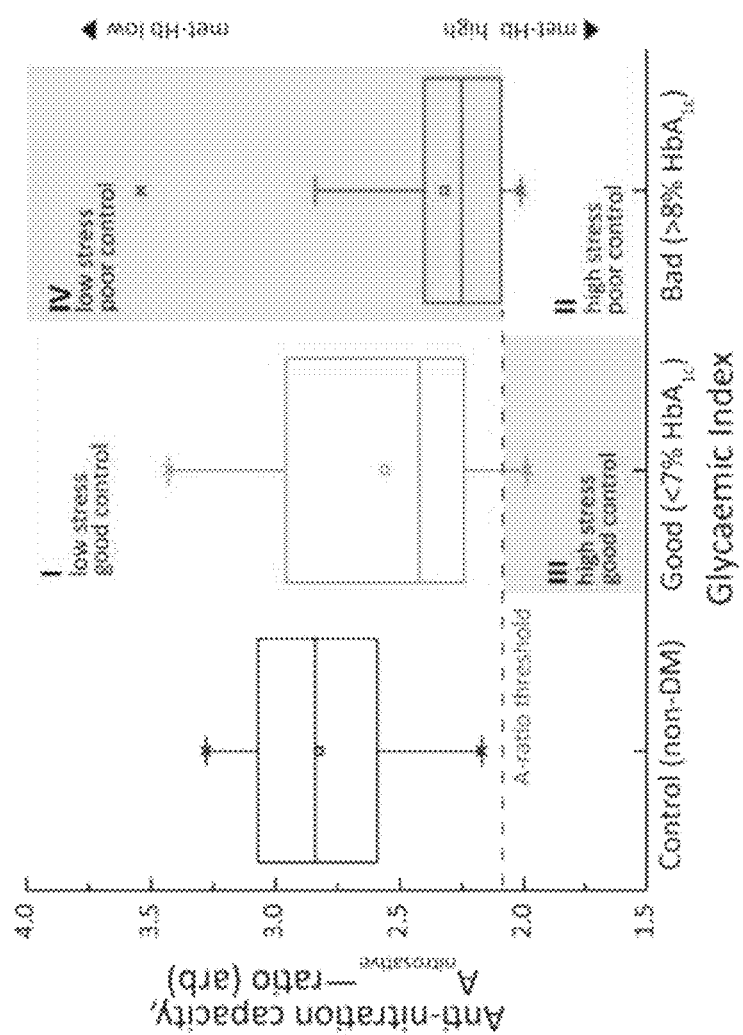

The spread were however large for good glycaemic control group, which suggest a large subject variability of nitrosative susceptibility, despite having similar glycaemic level (FIG. 4E). Using the nitrosative susceptibility ($A_{nitrosative}$-ratio), which could be derived hypothetically from this study and the traditional index of glycaemic control ($HbA_{1c}$), DM subjects could be stratified into four distinct quadrants (Q1-Q4). This approach singled out a minority group in Q3, who had good glycaemic control, and yet nitrosative stress the $A_{nitrosative}$-ratio threshold that was 75-percentile of that typical to DM subjects with poor glycaemic control. Further large-scale prospective study in different population would be needed, to establish predictive power of these new measurements combined with glycemic marker.

Baseline Study: Glycation and Glycoxidation of Plasma Serum

Figure 5A:
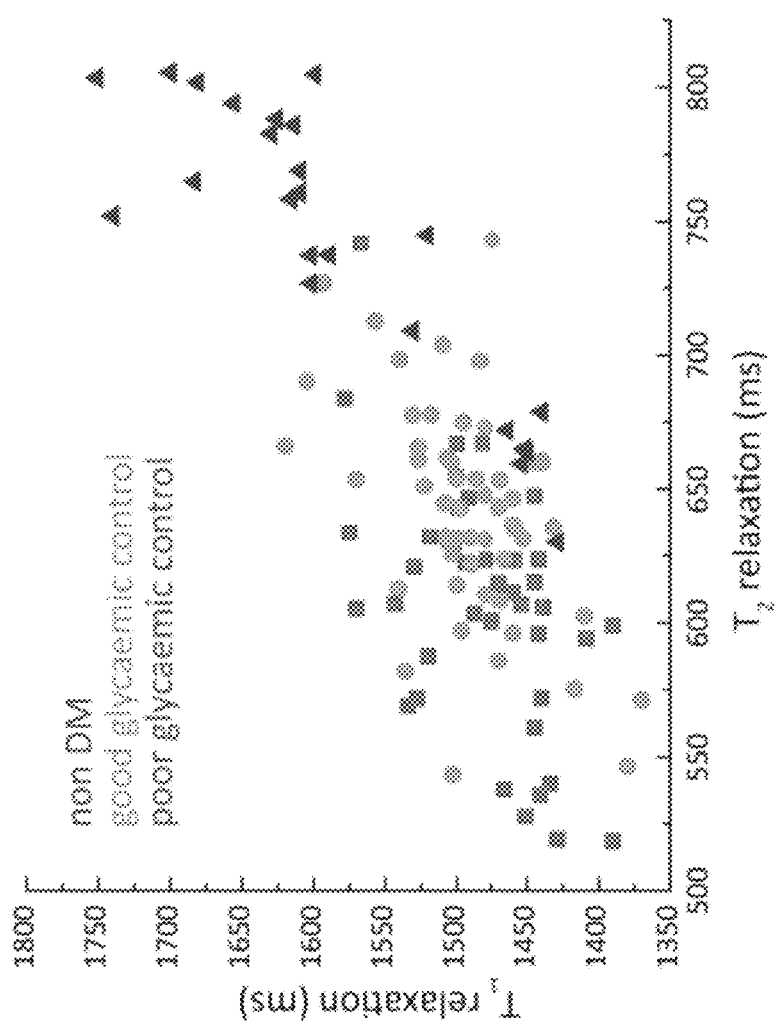
FIGS. 5A-5D show the $T_1$-$T_2$ coordinates of MRR measured plasma baseline readings for each single subject from non-DM subjects (triangle), poor (square) and good (round) glycaemic control subjects.
Figure 5B:
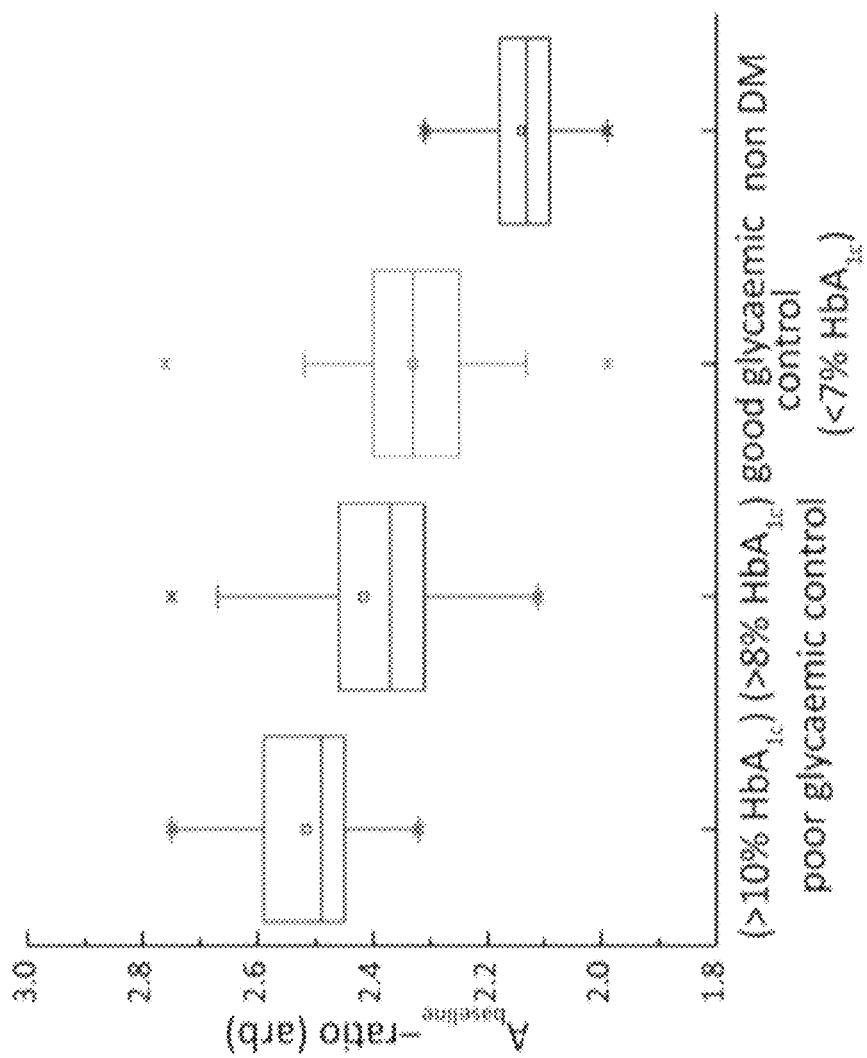
Figure 5C:
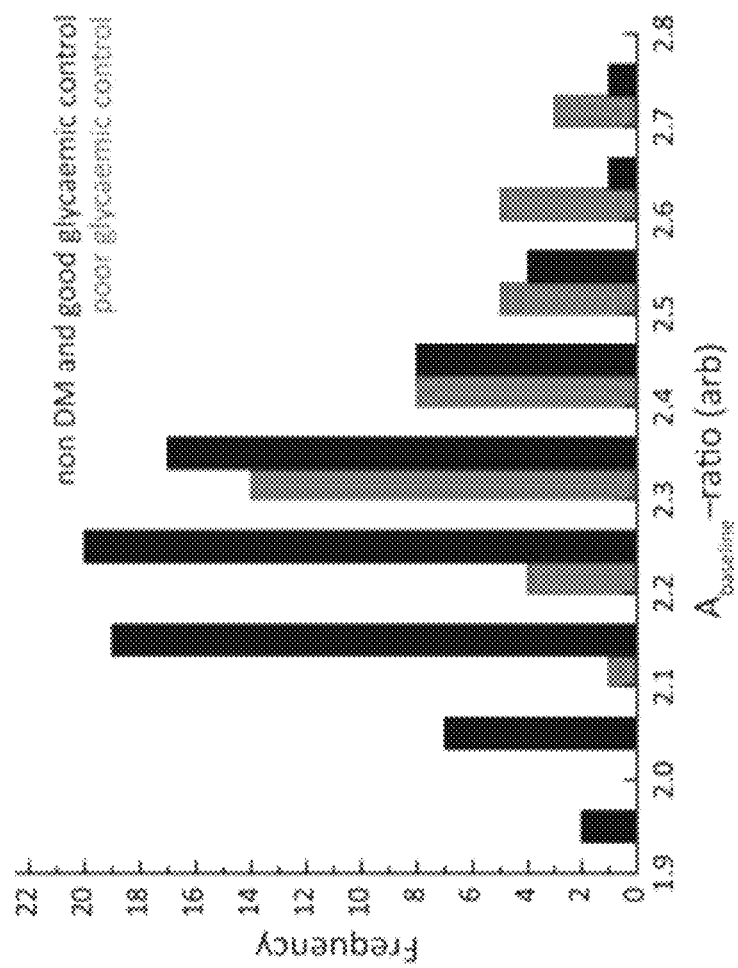

Increased blood glucose promotes non-enzymatic glycation of plasma proteins, which include the albumin, alpha-crystalline, collagen, and low-density lipoprotein. See, Lodovici, M., et al. Oxidative DNA damage and plasma antioxidant capacity in type 2 diabetic patients with good and poor glycaemic control. *Mutation Research/Fundamental and Molecular Mechanisms of Mutagenesis* 638, 98-102 (2008), Lee, R., Margaritis, M., Channon, K. & Antoniades, C. Evaluating oxidative stress in human cardiovascular disease: methodological aspects and considerations. *Current medicinal chemistry* 19, 2504 (2012), and Bourdon, E., Loreau, N. & BLACHE, D. Glucose and free radicals impair the antioxidant properties of serum albumin. *The FASEB journal* 13, 233-244 (1999), each of which is incorporated by reference in its entirety. However, a large proportion of total serum protein is attributable to serum albumin. See, Roche, M., Rondeau, P., Singh, N. R., Tarnus, E. & Bourdon, E. The antioxidant properties of serum albumin. *FEBS letters* 582, 1783-1787 (2008), which is incorporated by reference in its entirety. Glycation and oxidative damage cause protein modifications and hence its functionality. MRR baseline and peroxidative stress measurements were performed on the plasma serum at room temperature. See, Yilmaz, A., Ulak, F. & Batun, M. Proton $T_1$ and $T_2$ relaxivities of serum proteins. *Magnetic resonance imaging* 22, 683-688 (2004), which is incorporated by reference in its entirety. Each $T_1$-$T_2$ coordinate represented the composite redox properties (see, Bernhardt, I. & Ellory, J. Red cell membrane transport in health and disease. (2003), and Moussa, S. Oxidative stress in diabetes mellitus. *Romanian J Biophys* 18, 225-236 (2008), each of which is incorporated by reference in its entirety) of one subject (FIG. 5A). FIG. 5A shows the $T_1$-$T_2$ coordinates of MRR measured plasma baseline readings for each single subject from non-DM subjects (triangle, n=24), poor (square, n=37) and good (round, n=55) glycaemic control subjects. Plasma baseline $T_1$-$T_2$ coordinates of the DM subjects (both the poor and good glycaemic control) concentrating in the lower quadrants were well separated from the non-DM subjects. FIG. 5B shows the breakdown details in A-ratio for poor (>8% and >10% $HbA_{1c}$) and good glycaemic control (<7% $hbA_{1c}$) subgroups as opposed to non-DM. Median A-ratio for plasma baseline in this cohort were 2.49, 2.36, 2.32 and 2.12, for DM subjects with >10% $HbA_{1c}$, >8% $HbA_{1c}$, <7% $HbA_{1c}$, and non-DM, respectively (FIG. 5B). The combined frequency distributions were as shown in FIG. 5C.

Figure 5D:
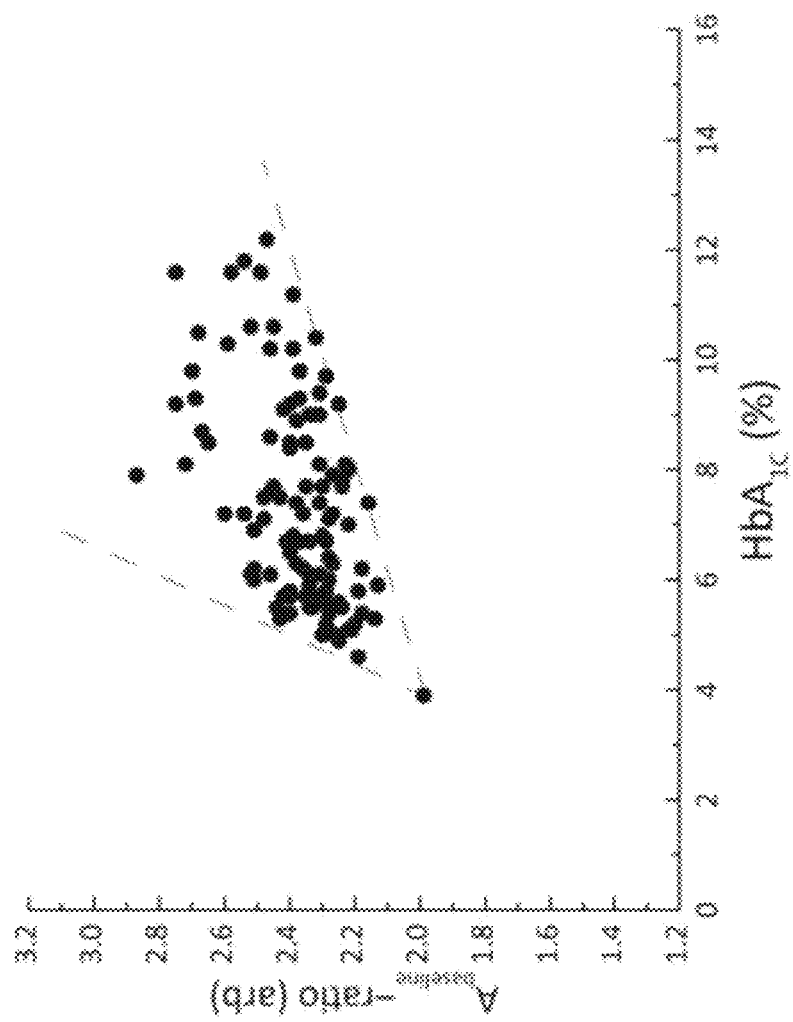

The marked reduction in relaxation states was attributed to an increase in glycation and glycoxidation of the serum albumin. As a result of increased glycation (FIG. 15A) and protein oxidative damage (e.g. protein crosslinking) the bulk water proton of mobility (see, Grosch, L. & Noack, F. NMR relaxation investigation of water mobility in aqueous bovine serum albumin solutions. *Biochimica et Biophysica Acta (BBA)-Protein Structure* 453, 218-232 (1976), which is incorporated by reference in its entirety) was restricted, hence the reduction in $T_1$ and $T_2$ relaxation times. $T_2$ relaxation however reduced much faster than $T_1$ relaxation resulting in an increment in $A_{baseline}$-ratio, which had positive correlation with respect to $HbA_{1c}$ ($R^2$>0.72) (FIG. 5D). Similar trends were observed in vitro, which confirm the effect of glycation (FIGS. 15A and 15B) and glycoxidation effect (FIG. 15C). Interestingly, ROC analysis indicates DM subjects with good-glycaemic control and non-DM subjects were 0.85 (not shown), much higher than the one observed in RBCs (AUC<0.39 in FIG. 4D). This suggests that pathological footprint of hyperglycemia were more prominent in extracellular plasma as opposed to RBCs. See, Lodovici, M., et al. Oxidative DNA damage and plasma antioxidant capacity in type 2 diabetic patients with good and poor glycaemic control. *Mutation Research/Fundamental and Molecular Mechanisms of Mutagenesis* 638, 98-102 (2008), which is incorporated by reference in its entirety.

Figure 6A:
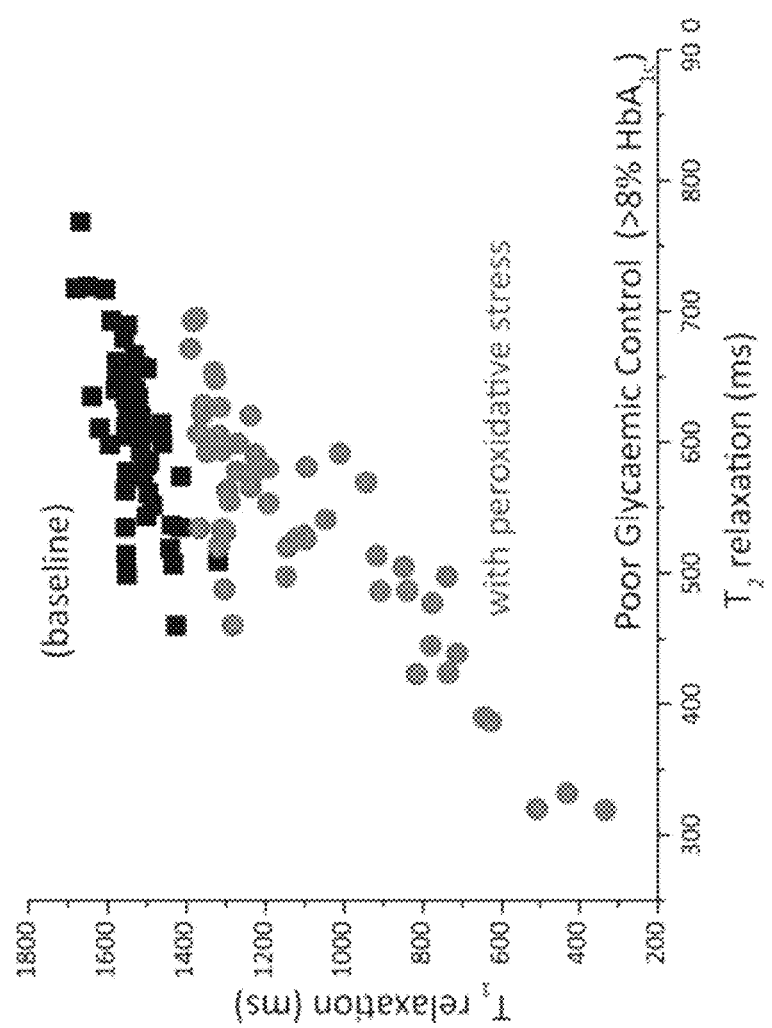
FIGS. 6A-6E show the $T_1$-$T_2$ diagram of MRR measured plasma serum baseline (square) and plasma pretreated with hydrogen peroxide (round) for subjects with poor glycaemic control (FIG. 6A), good glycaemic control (FIG. 6B), and non-DM (FIG. 6C). Each single point represents a MRR reading taken from one subject.
Figure 6B:
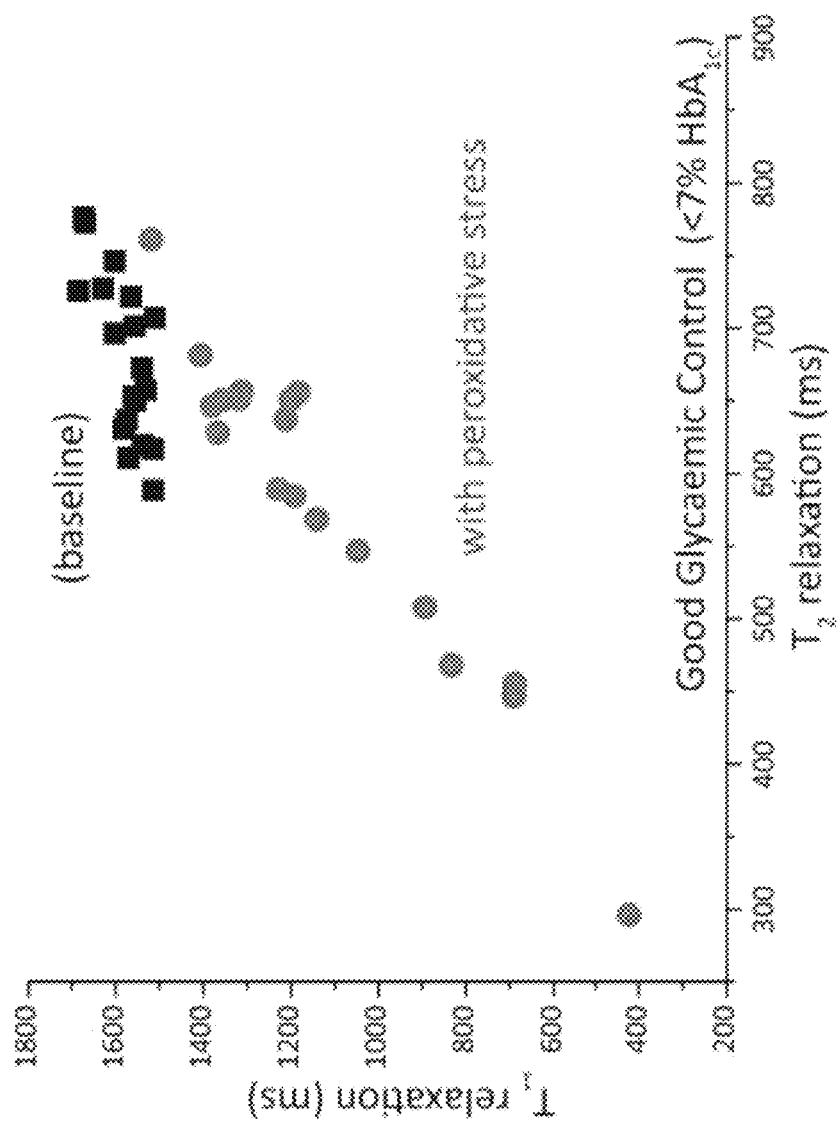
Figure 6C:
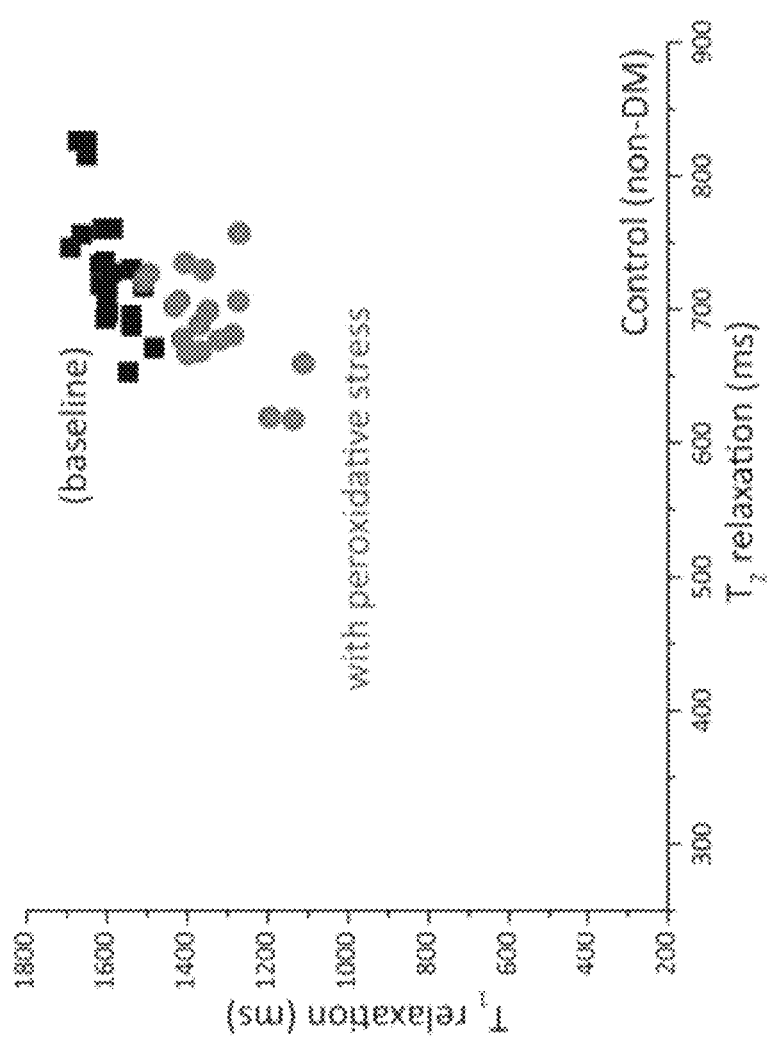

Peroxide-Induced Oxidation Analysis: Total Anti-Oxidant Capacity of Plasma Serum in Diabetes Mellitus Subjects In order to evaluate the total anti-oxidant capacity of plasma serum towards oxidation, the plasma serum was artificially challenged with hydrogen peroxide on subjects with poor glycaemic control (n=52), good glycaemic control (n=18), and non-DM (n=21) as control (FIGS. 6A-E). Hydrogen peroxide solution was added into the freshly drawn plasma (10% v/v) for an incubation time of 10 min (FIGS. 14A-E). MRR measurements were performed before (squares) and after (circles) mixing (FIGS. 6A-6C).

Figure 6D:
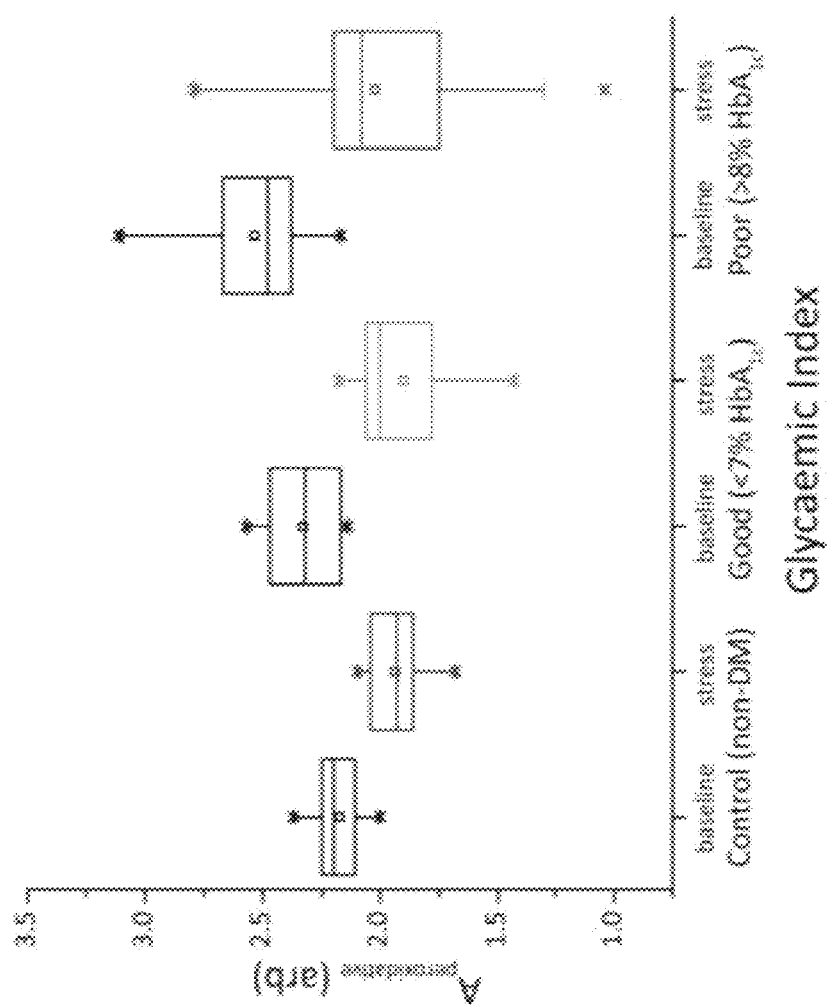

Stress-test results revealed a large spread of $T_1$-$T_2$ coordinates for DM subjects (FIGS. 6A and 6B), who varied markedly in their peroxidative susceptibility as compared to non-DM subjects (FIG. 6C). Lower anti-oxidant capacity (or increase in peroxidative stress susceptibility) of plasma is indicated by reduction in $T_1$ and $T_2$ relaxation coordinates (circles). As more oxidized plasma was formed, the $T_1$ relaxation time reduced much faster than $T_2$ relaxation time, and hence the reduction in $A_{peroxidative}$-ratio (FIG. 6D). This was in agreement with in vitro study (FIG. 15C).

Figure 6E:
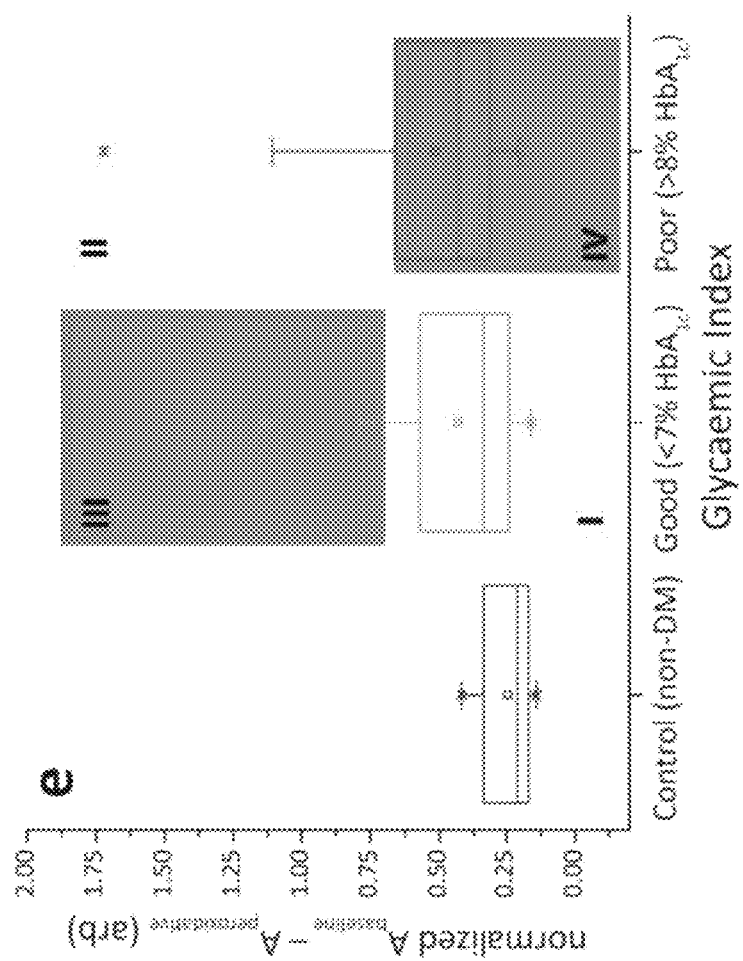
Figure 16A:
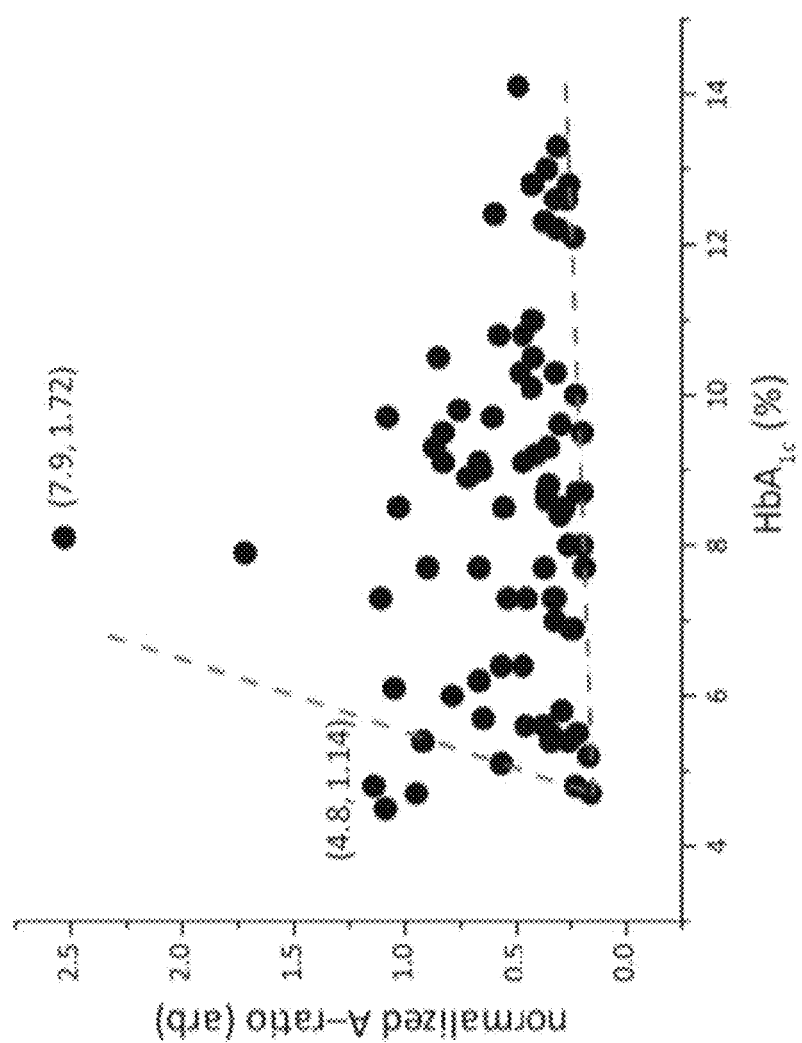
FIGS. 16A-16C show correlation of plasma, glycaemic level (fructosamine and $HbA_{1c}$) and oxidative status.

DM subjects had much higher plasma peroxidative susceptibility as compared to non-DM counterparts (FIG. 6E). The normalized plasma peroxidative stress susceptibility can be loosely defined by $A_{baseline}$-ratio subtracting the $A_{peroxidative}$-ratio (FIG. 6E). The peroxidative susceptibility was also found to be positively correlated to glycaemic levels, both the $HbA_{1c}$ (FIG. 16C) and fructosamine level (FIG. 16D). Note that the plasma baseline (black) measurements of this cohort had similar positive trend with respect to glycaemic levels (FIG. 6D) were in agreement with the previous cohort measured independently (FIGS. 5A-D). Exposure to peroxyl compound led to increased formation of disulfide bonding in albumin and human non-mercaptalbumin were reported in several other pathologic conditions. See, Oettl, K. & Stauber, R. Physiological and pathological changes in the redox state of human serum albumin critically influence its binding properties. *British journal of pharmacology* 151, 580-590 (2007), SOGAMI, M., et al. HPLC-studies on nonmercapt-mercapt conversion of human serum albumin. *International journal of peptide and protein research* 25, 398-402 (1985), and Kadota, K., Yui, Y., Hattori, R., Murohara, Y. & Kawai, C. Decreased sulfhydryl groups of serum albumin in coronary artery disease. *Japanese circulation journal* 55, 937-941 (1991), each of which is incorporated by reference in its entirety. The peroxidative susceptibility measurements (FIG. 6E), independent of HbA1c stratify the DM subjects into sub-groups which provides insight into the oxidative status (susceptibility and damage) of each individual patients.

Calibration of MRR Measurements with Photospectrometry

Figure 7A:
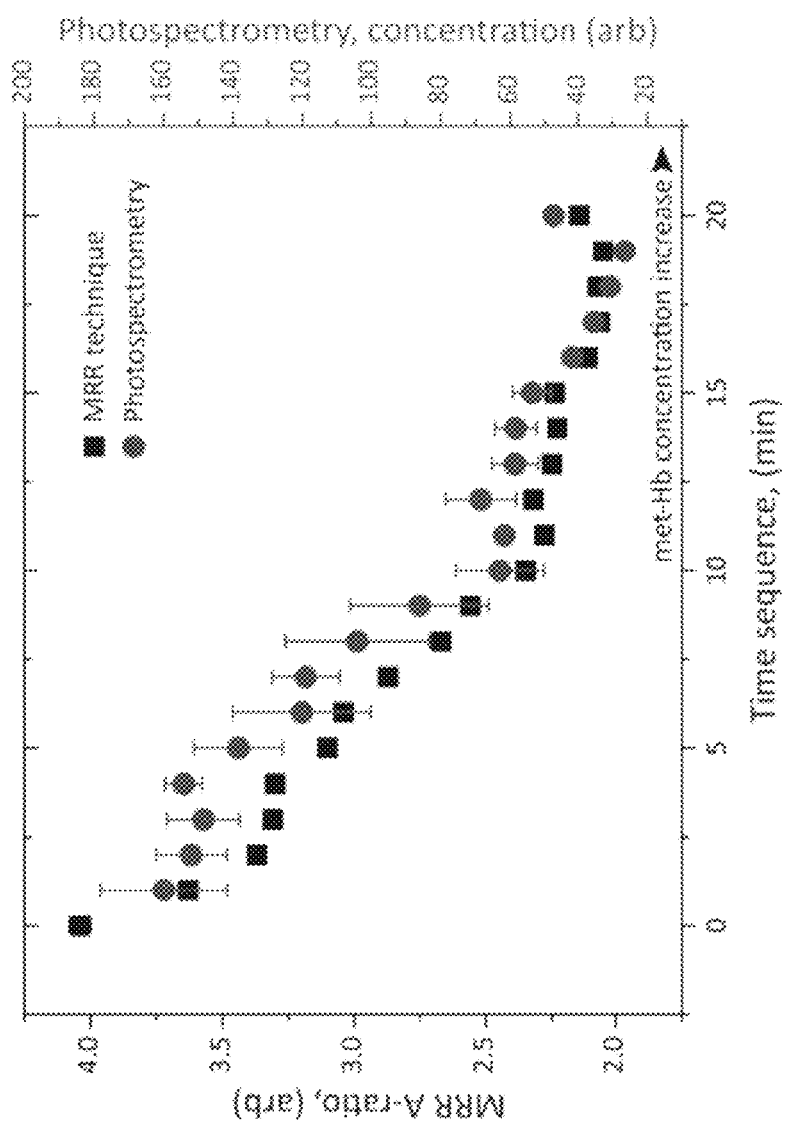
FIGS. 7A-7B show calibration MRR technique with photospectrometry.
Figure 7B:
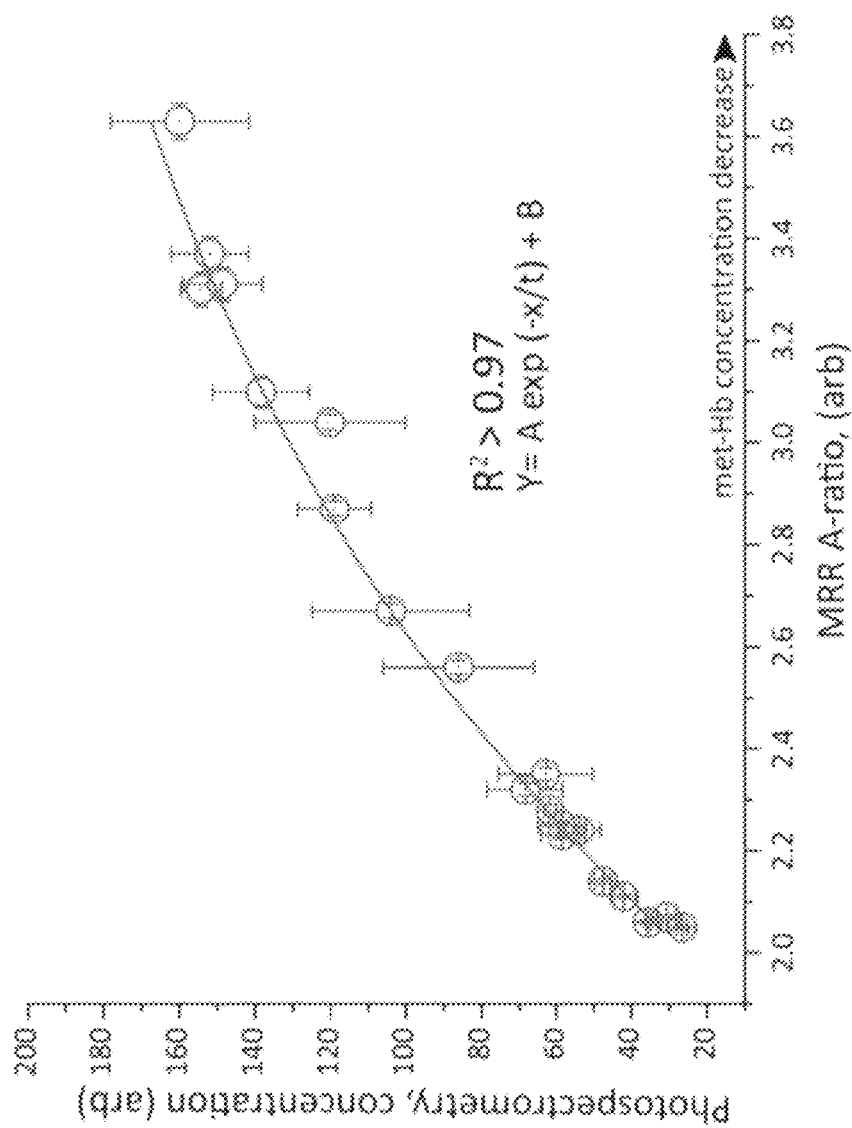
Figure 8A:
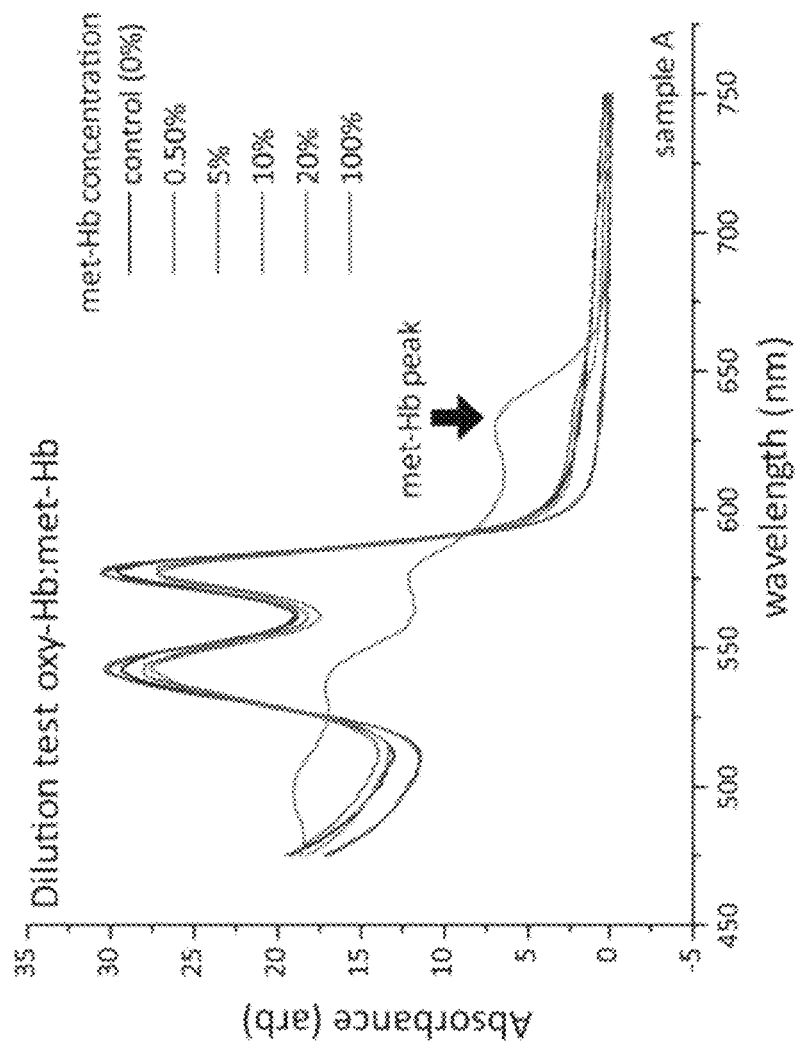
FIGS. 8A-8D show limit of detection for photospectrometry technique in met-Hb detection.
Figure 8B:
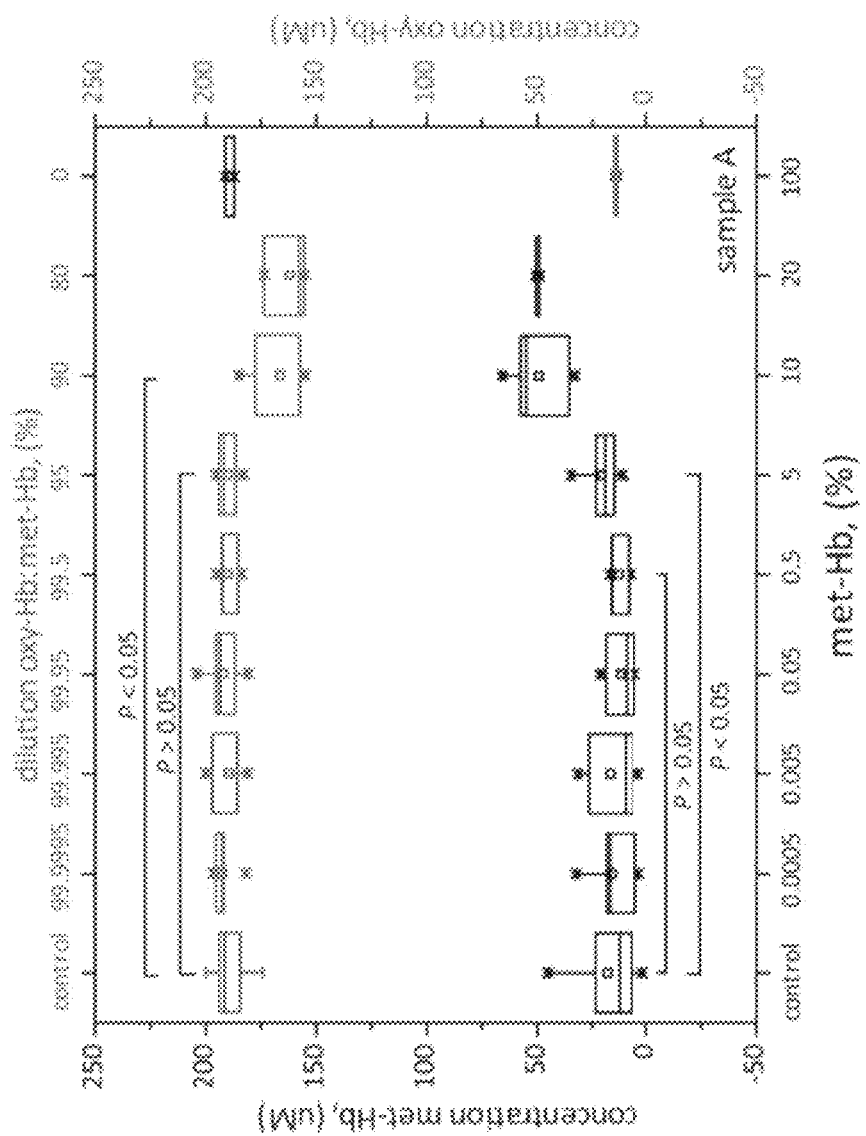
Figure 8C:
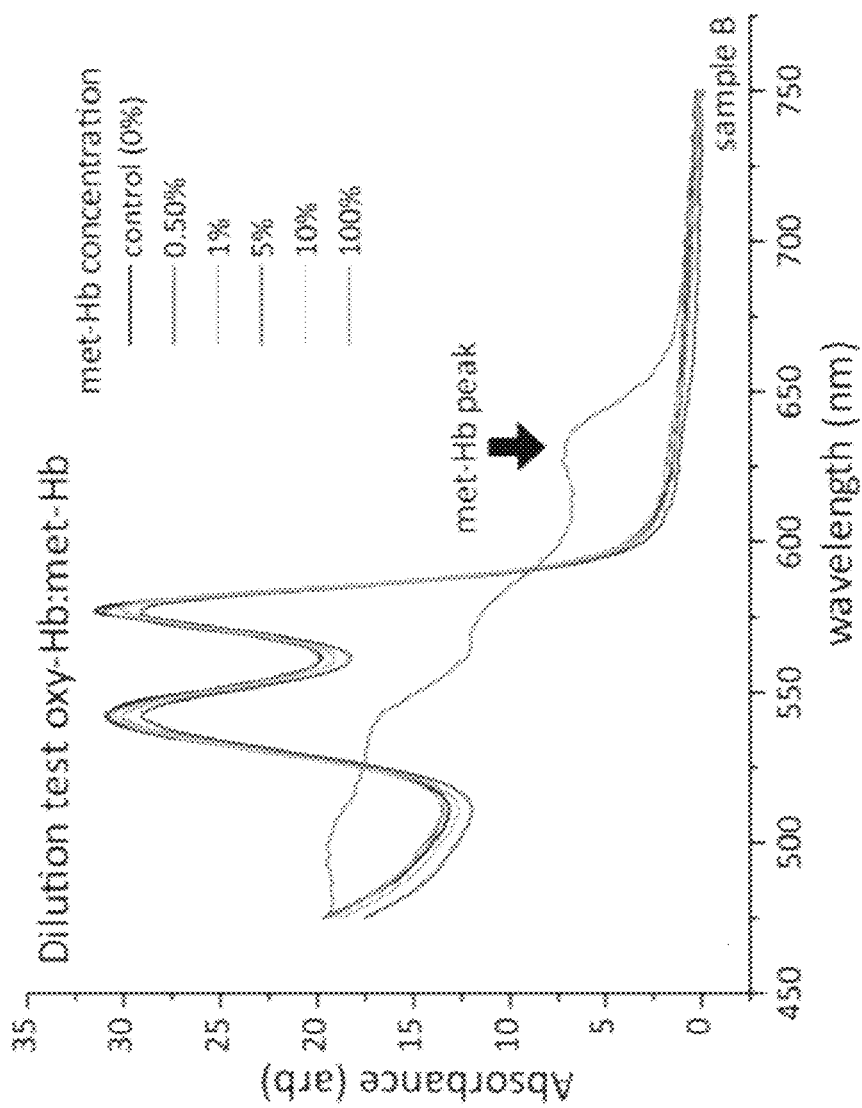
Figure 8D:
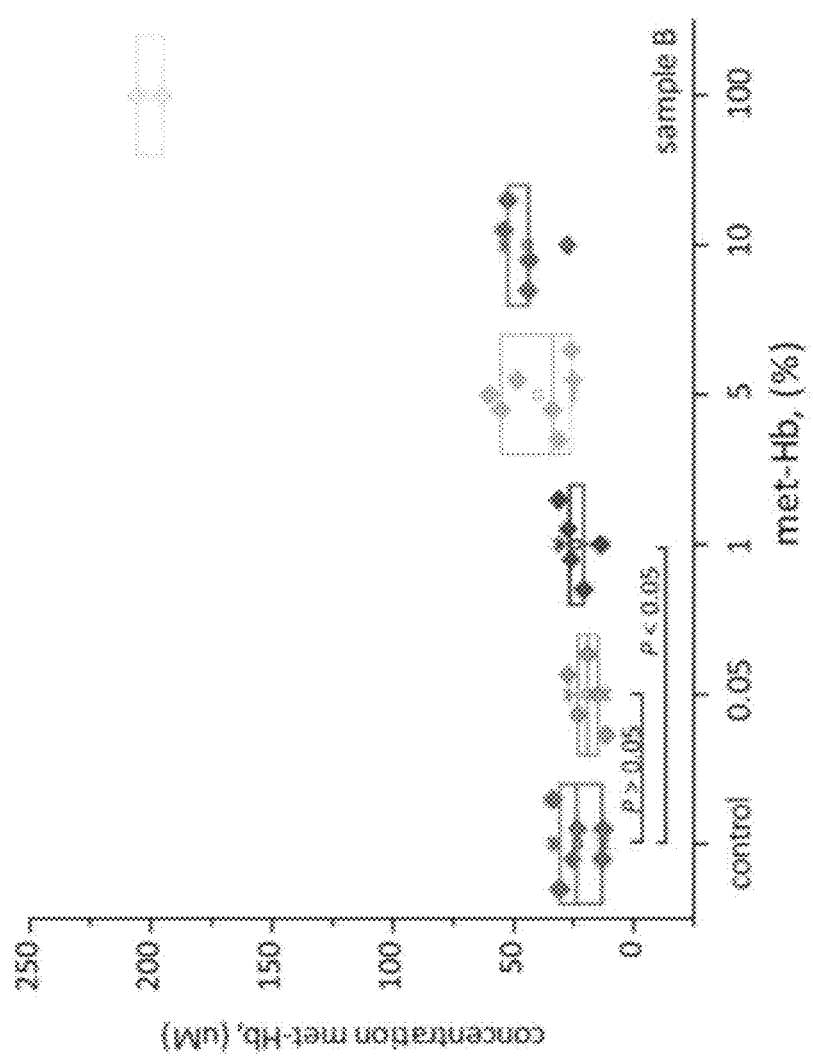

Freshly drawn blood were washed, resuspended into 1×PBS and exposed to 6 mM nitrite. The amount of oxy-Hb to met-Hb conversion was measured independently using MRR and photospectrometry techniques at y one minute intervals. FIG. 7A shows Time dependent kinetic profile for nitrite-induced oxidation of oxy-Hb as measured by MRR (n=3) and photospectrometry (n=5 to 8). 6 mM nitrite concentration was used and the RBCs were sampled and measured at every 1 min intervals. Error bars were standard deviation. Note that the error bars for MRR measurements were too small (<5%). The kinetic profile of met-Hb formation over time (FIG. 7A) as monitored by MRR mapped closely to the photospectormery technique ($R^2 > 0.97$) (FIG. 7B). The time-dependant oscillatory decay profile was also observed here, similarly to the one observed in another donor (FIGS. 2A-H). It is also worth noting that the sensitivity dropped (as indicated by the error bars) for photospectrometry measurement as the met-Hb concentration reduce (FIG. 7B), which suggests low optical absorption properties of met-Hb. We further investigated and compared the limit of detection for both the optical- and magnetic based methods (FIGS. 8A-D).

Limit of Detection: Comparison Between MRR and Photospectrometry Technique

Met-Hb were spiked into oxy-Hb at various concentrations from 0.0005% to 100% and were measured simultaneously using both photospectrometry (FIGS. 8A-D) and MRR system (FIGS. 9A-D). The concentration (μM) were calculated from two absorbance peaks12 at 577 nm and 630 nm and based 1 mm optical path, the [oxy-Hb]=$6.6A_{577}$-$8A_{630}$ and [met-Hb]=$27.9A_{630}$-$0.3A_{577}$. Repeated sampling (n >8) was carried out for each dilution. The limit-of-detection (P-value <0.05) for photospectrometry technique was found to be approximately 5%, and 1% met-Hb for sample A and B, respectively. The optical spectra for low concentration of met-Hb (<1%) were poorly resolved (FIGS. 8A and 8C), which is due to the attributes of low optical absorption of the oxidized hemoglobin at 630 nm wavelength.

Figure 9A:
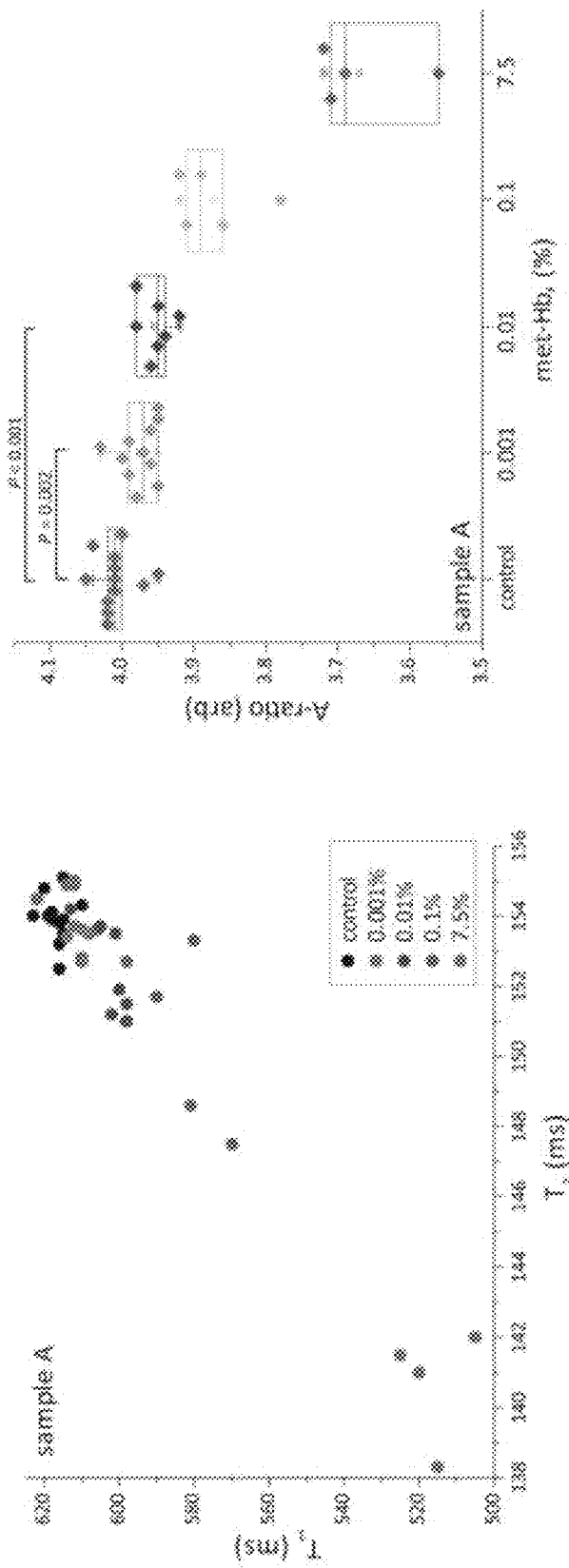
FIGS. 9A-9D show limit of detection for MRR technique in met-Hb detection. $T_1$-$T_2$ diagram (left panel) and A-ratio against the met-Hb concentration (%) (right panel) for sample A (FIG. 9A), sample B (FIG. 9B), and sample C (FIG. 9C).
Figure 9B:
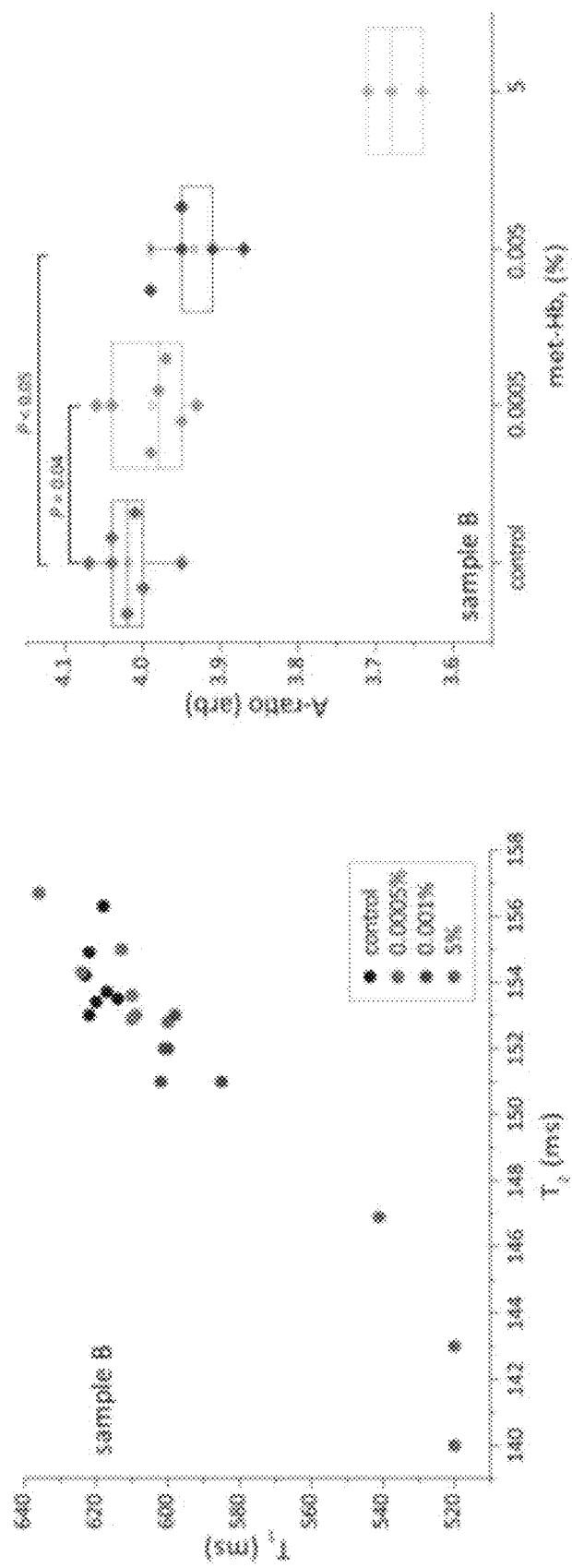
Figure 9C:
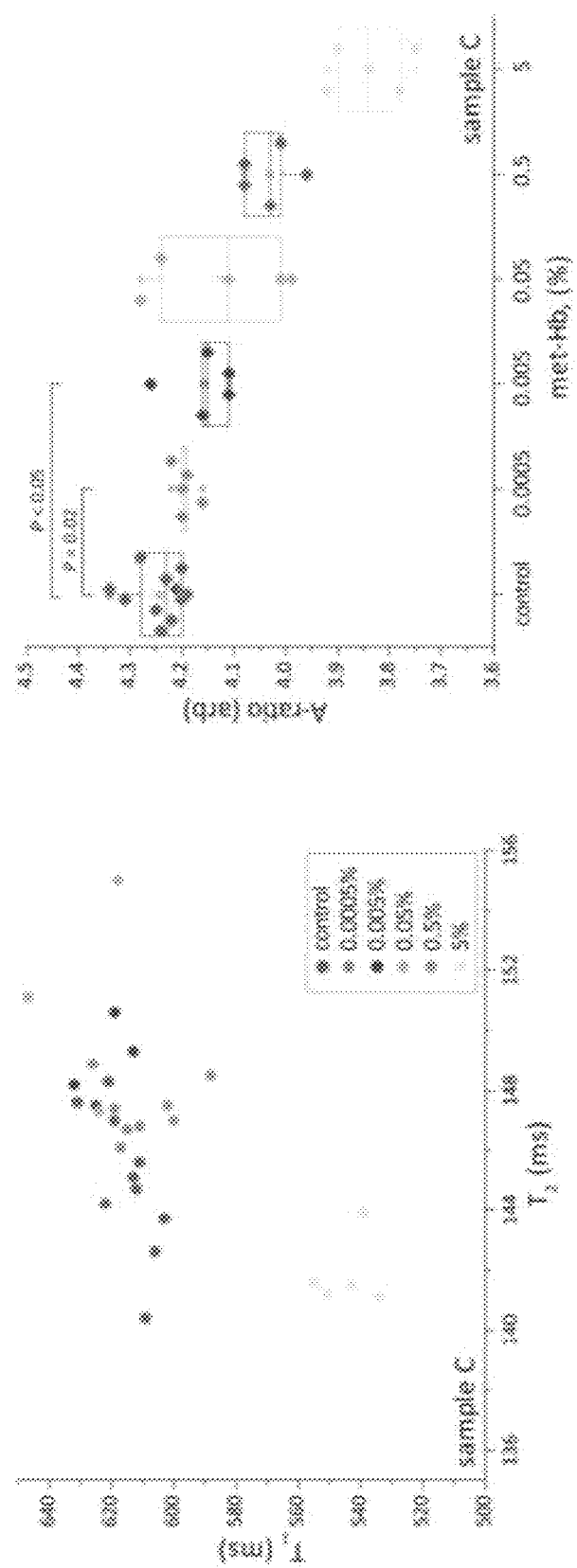
Figure 9D:
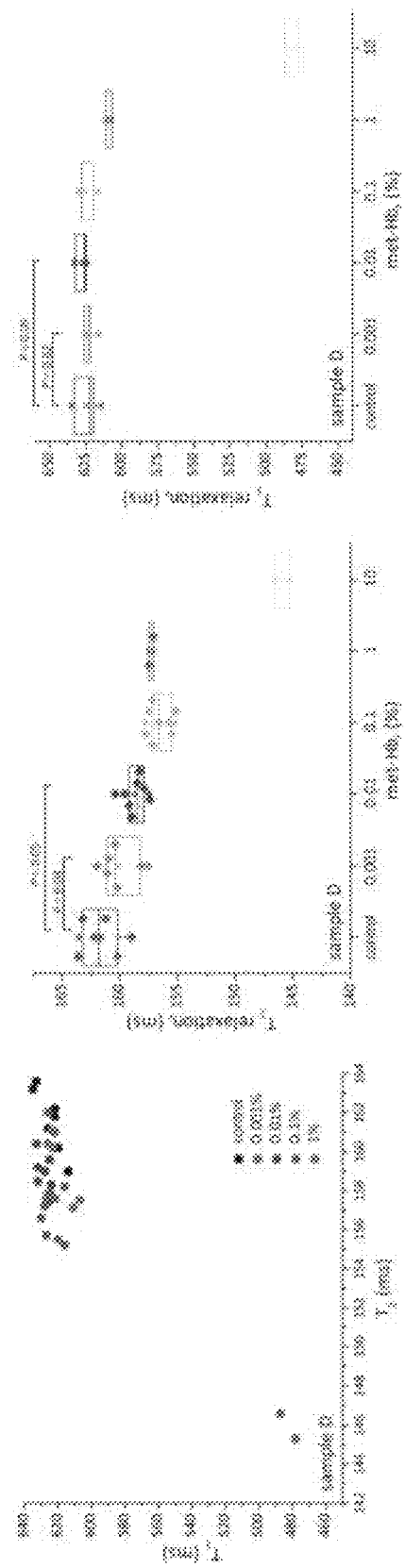

For MRR measurement, the dilution experiment was repeated four times on four different blood samples (sample A, sample B, sample C and sample D). Paramagnetic susceptibility of met-Hb causes reduction in $T_1$, $T_2$ relaxations and A-ratio. The results in FIGS. 9A-D suggest that depending on the condition of the blood and donors variability, a limit-of-detection (P-value<0.05) of approximately 0.0005% can possibly be achieved under well-controlled experiment (FIGS. 9A-9C). One tailed student's t-test of paired test were used to calculate the P-value. Scatter plot of $T_1$-$T_2$ diagram (left panels in FIGS. 9A-D) show clustered points which are separated based on its' respectively dilution factors.

As the concentration of met-Hb reduces to less than 0.1%, a larger number of samplings (n>5) were required to improve the sampling probability. Depending on the blood condition (e.g., donor variability, unfresh blood or other anomaly), a time-dependant effect due to a number of confounding factors such as extra- and intracellular water movement across the membrane altering which shifted the baseline of $T_1$ and $T_2$ index (sample C), but retaining the A-ratio. It is also worth noting that, in some cases as the met-Hb concentration were very low (<0.1%) the $T_2$ parameters were much more stable as compared to $T_1$ and A-ratio (sample D). Nonetheless, these results combined (either A-ratio and/or $T_2$ index), MRR technique is at least 3-4 orders much high sensitivity than the photospectometry system used in this work. Note that, the sensitivity enhancement of MRR technique can achieved by doping met-Hb with natrium fluoride to form fluoromet-Hb, which have much higher relaxivity and is stable towards temperature fluctuation[1]. This is however out of the scope of the current study resented here.

Nitrite Concentration Selection Criteria for Nitrite-Induced Oxidation of RBC Assays (Short-Time 10 Min Incubation)

Two selection criteria in deciding the optimal range of nitrite concentration (at 10 min incubation) reflect the high degree of inter-individual variability. The rate limiting factor of this assay is the sample incubation time, which can be reduced by increasing the nitrite concentration to achieve faster turnaround time. Twelve subjects were randomly selected from both the good and bad glycaemic control groups—a range of $HbA_{1c}$ (4.2% to 9.7%). Freshly drawn blood were washed and resuspend into 1×PBS. The blood were then treated with various concentration of sodium nitrite for 10 minutes (FIG. 11A) and the MRR measurements were performed (FIG. 11B). This result (FIGS. 11C and 11D) is used to guide the selection of suitable nitrite concentration which reflects a large degree of inter-individual variability. Box plot indicate the 25% and 75% quantiles. The p-values were calculated by using student's t-test for two samples-test of unequal variances. AUC of >0.9, >0.8, <0.7, is considered excellent (dark blue), good (blue) and poor (light blue), respectively.

Figure 11C:
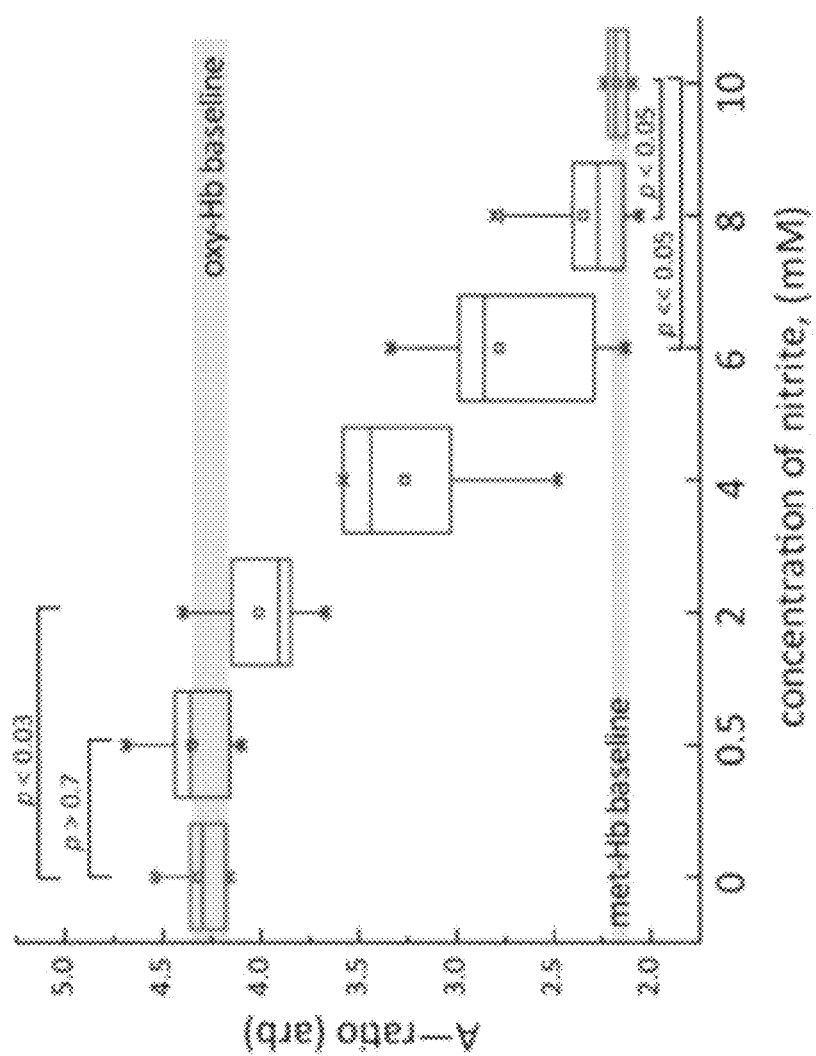

The induced stress measurement must be statistically significant different (P-value <0.05) from both the fully oxy-Hb and met-Hb baselines (FIG. 11C). Secondly, it is desirable to have high degree of inter-individual variability that reflect high resolution as shown by the spread between 25% and 75% quantile box plots. Nitrite concentration in the range of 2 mM to 8 mM, reflects the bio-homeostatis and satisfied the diagnostic criterion (FIG. 11D). Nonetheless, higher level of differentiation (resolution) between subjects can be achieved by induction with much higher nitrite concentration. However, one should caution against overstressing the cells as conversion of all RBCs into met-Hb (e.g., 10 mM) reveals no information of homeostasis feedback. In this work, 6 mM nitrite was chosen for all the nitrite-induced oxidation assay, unless otherwise mentioned.

Nitrite Concentration Selection Criteria for Nitrite-Induced Oxidation of RBC Assays (Long-Time 36 Hrs Incubation)

Figure 12A:
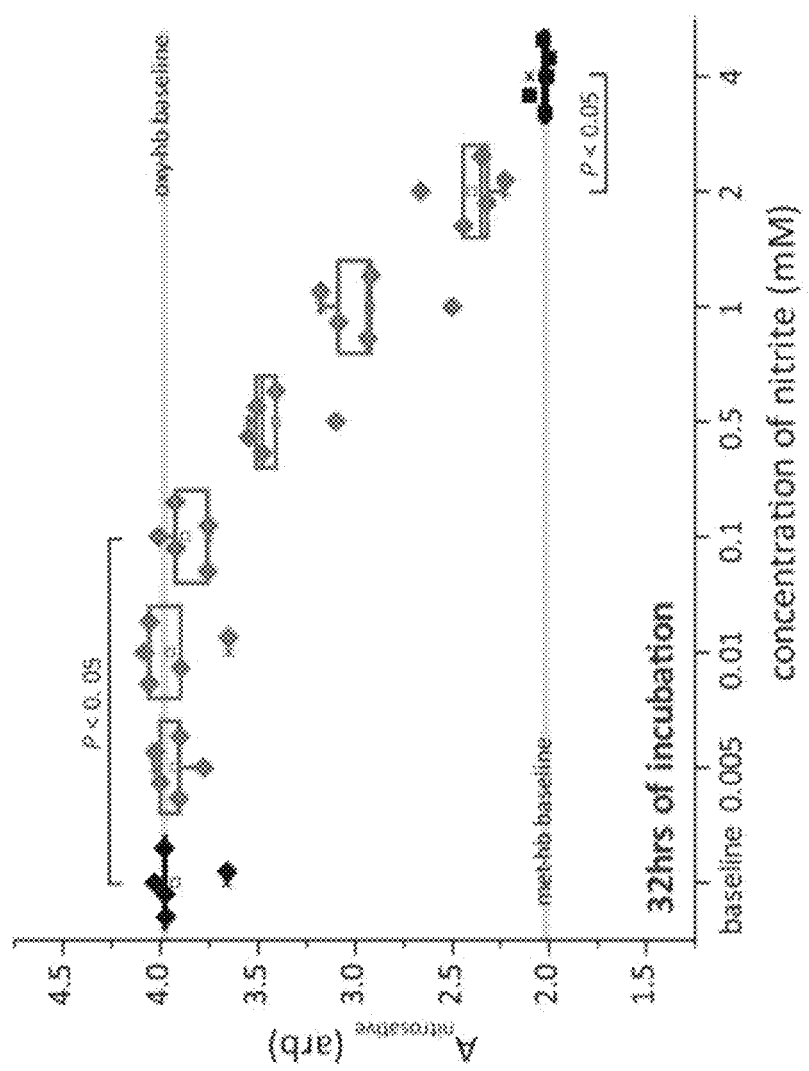
FIGS. 12A-12B show nitrite concentration selection criteria for nitrite-induced oxidation of RBC assays for a very long-time period.
Figure 12B:
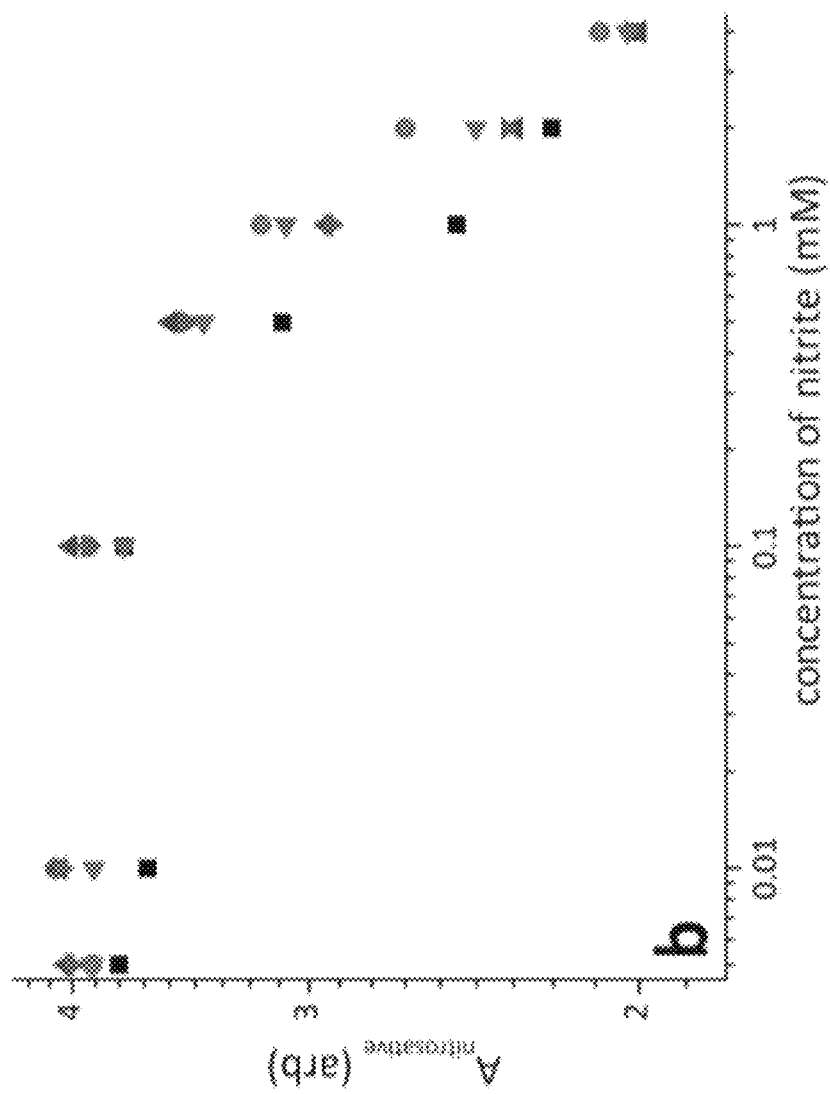
Figure 12C:
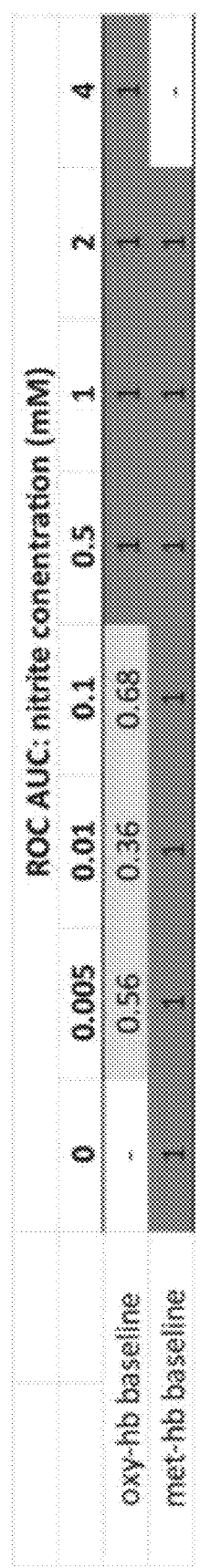
FIG. 12C shows ROC-AUC calculated for each nitrite concentration against the oxy-Hb and met-Hb baseline.

The same experiment was repeated on five randomly assigned subjects taken from a range of $HbA_{1c}$ (5.4%-13%) and their responses to various sodium nitrite concentration (0, 5 μM, 0.01 mM, 0.1 mM, 2.0 mM, 4.0 mM) were recorded (FIGS. 12A-B). In this experiment, the incubation period were increased to 36 hrs instead of 10 min as shown in FIGS. 11A-D. Only 4 mM nitrite is needed to induced a complete transition to met-Hb instead of 10 mM as shown previously (FIG. 12A). With the longer incubation, the homeostatis feedback range has shifted to 0.5 mM-2 mM instead of 2 mM to 6 mM, as shown previously. Therefore, one could use lower nitrite concentration (nM to μM range) can be used if the incubation time is not a limiting factor. Inter-individual variability at low nitrite concentration (μM range) appeared to be much smaller as depicted in log-log plot in FIG. 12B. The p-values were calculated by using student's t-test for two samples-test of unequal variances. AUC of >0.9, >0.8, <0.7, is considered excellent (dark blue), good (blue) and poor (light blue), respectively.

Prolonged Effect of In Vitro Exposure to Peroxidative Stress on RBCs

Perodixe is a byproducts of oxygen metablolism produces intracellular reactive oxygen species. See, Roche, M., Rondeau, P., Singh, N. R., Tarnus, E. & Bourdon, E. The antioxidant properties of serum albumin. *FEBS letters* 582, 1783-1787 (2008), which is incorporated by reference in its entirety. The steady state concentration of $H_2O_2$ in the RBCs is reported to be approximately 0.2 nM[3], and a dramatic increased has also been shown to be possible under autoxidation[4]. See, Giulivi, C., Hochstein, P. & Davies, K. J. Hydrogen peroxide production by red blood cells. *Free Radical Biology and Medicine* 16, 123-129 (1994), and Rifkind, J., Zhang, L., Levy, A. & Manoharan, P. The hypoxic stress on erythrocytes associated with superoxide formation. *Free Radical Research* 13, 645-652 (1991), each of which is incorporated by reference in its entirety. The effect on anti-oxidant capacity of RBCs was due to prolonged (day to weeks) in vitro exposure to mild concentration of 90 nM of hydrogen peroxide ($H_2O_2$) (FIG. 11).

Figure 13A:
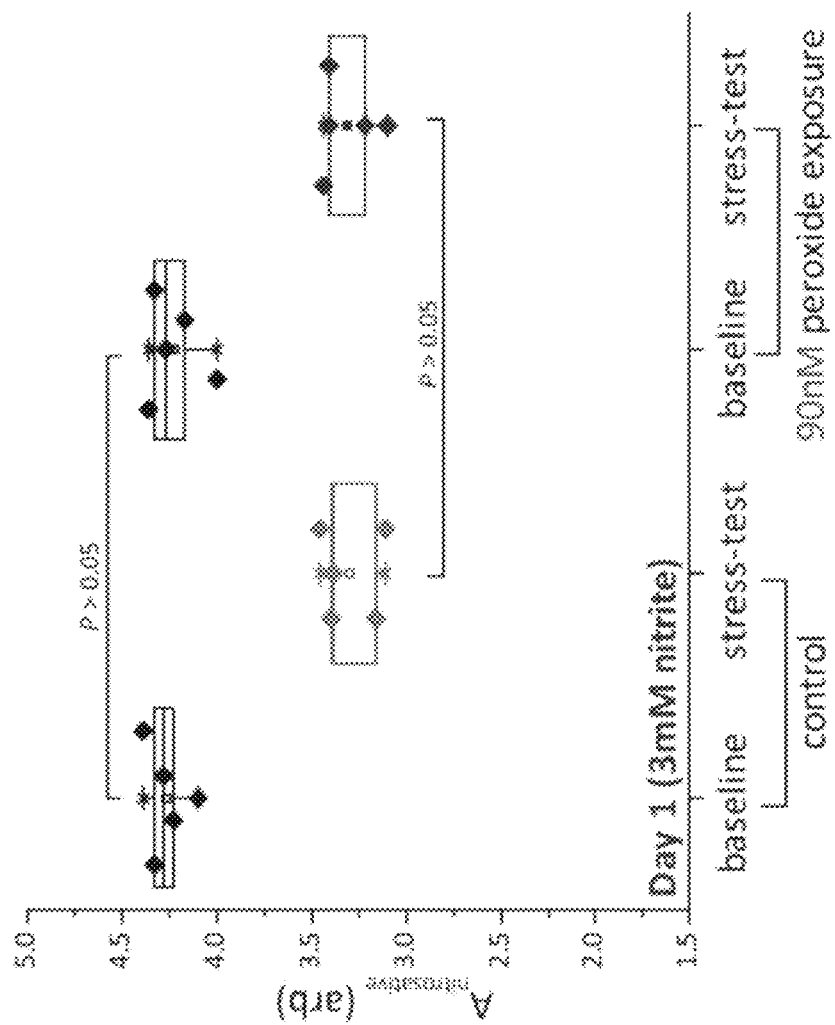
FIGS. 13A-13D show A-ratio responses of diabetic subjects to long term in vitro exposure to 'mild' concentration of $H_2O_2$ at various time points and concentrations.

Five subjects with $HbA_{1c}$ (6.1% to 13.8%) were randomly selected for the this experiment and the anti-oxidant capacity of the RBCs were measured by using nitrite-induced oxidation assay. Freshly drawn blood were washed and resuspended into 1×PBS (Day 0) and divided into two groups; pretreated with $H_2O_2$ and control (without treatment). In order to understand the total intracellular anti-oxidant properties of RBCs, rather than the whole blood, the serum were removed intentionally. The MRR measurements were performed at Days 1, 6, 13 of post exposure by using nitrite-induced oxidation assay to induce intracellular anti-oxidant capacity of the RBCs. On Day 1 of post-exposure, both the control and peroxide pretreated groups were similar (P-value >0.05) (FIG. 13A). However, on Day 6 (FIG. 13B), two of the five subjects in $H_2O_2$ pretreated group (blue) registered a drop in their anti-oxidant capacity as compared to control (red).

Figure 13B:
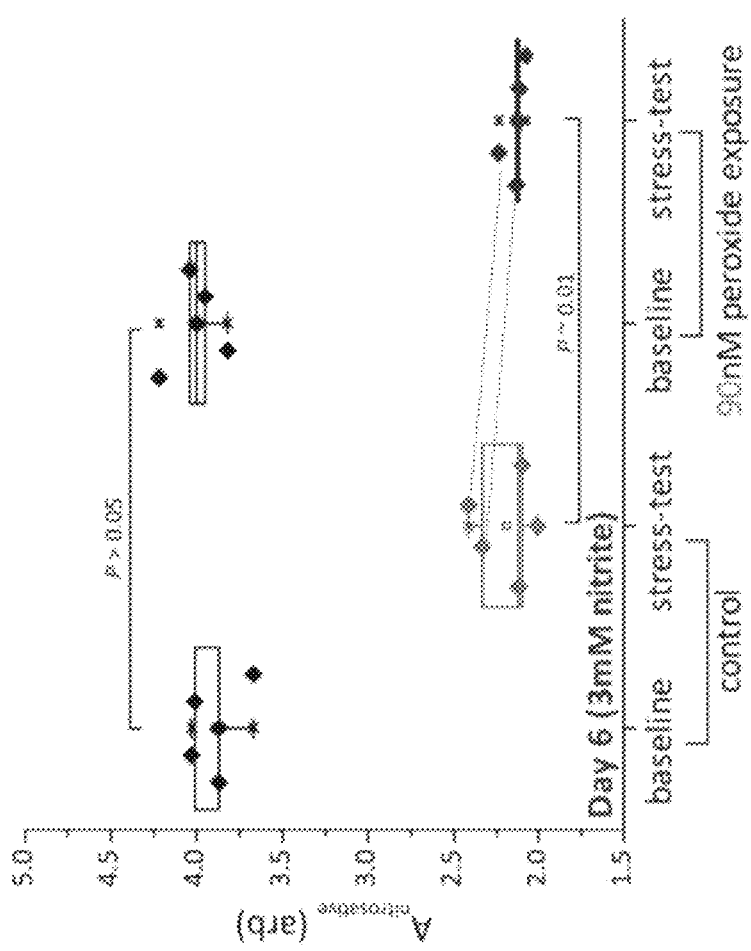
Figure 13C:
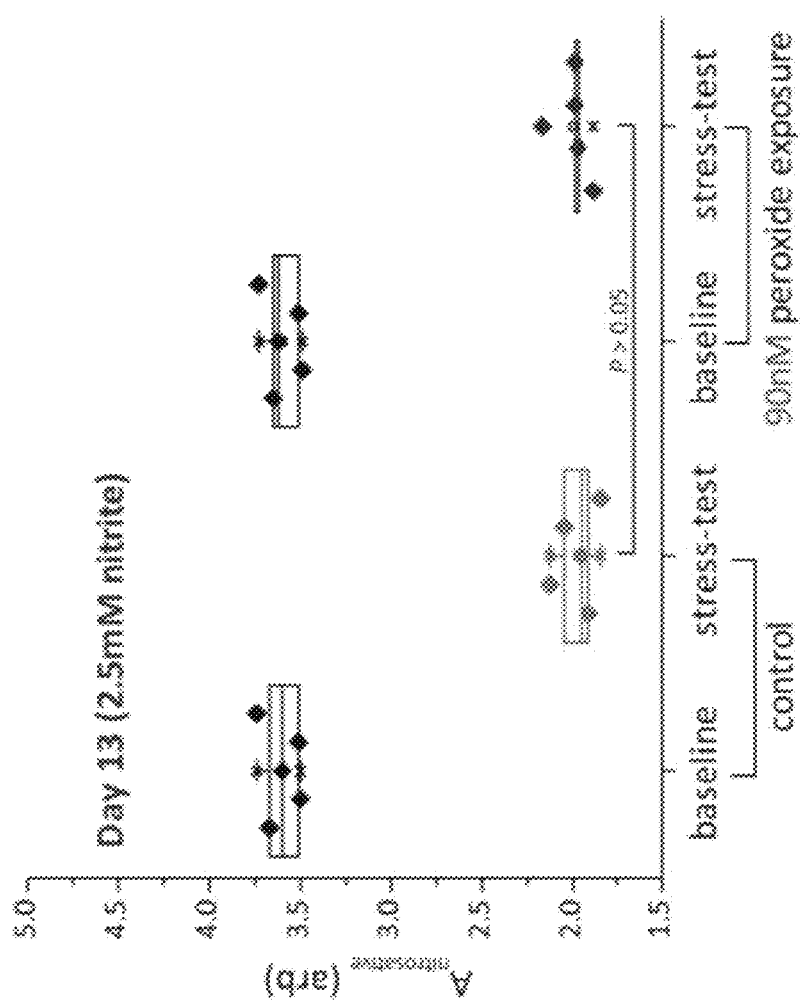
Figure 13D:
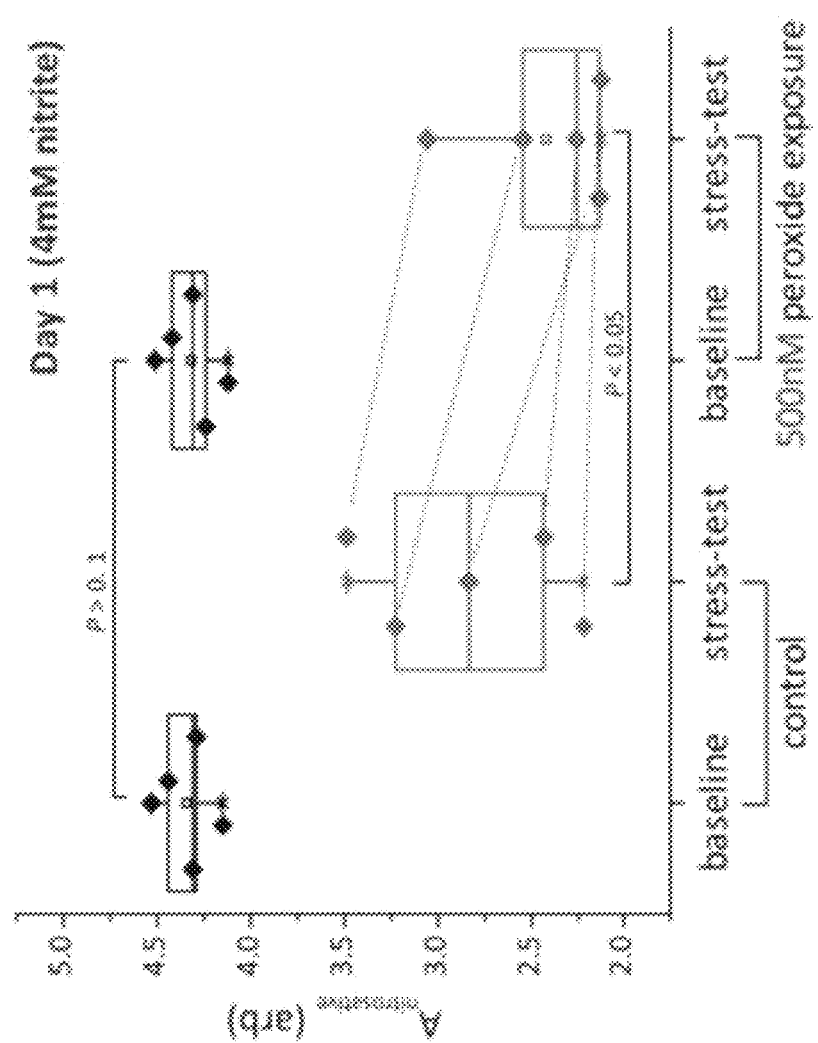
Figure 14A:
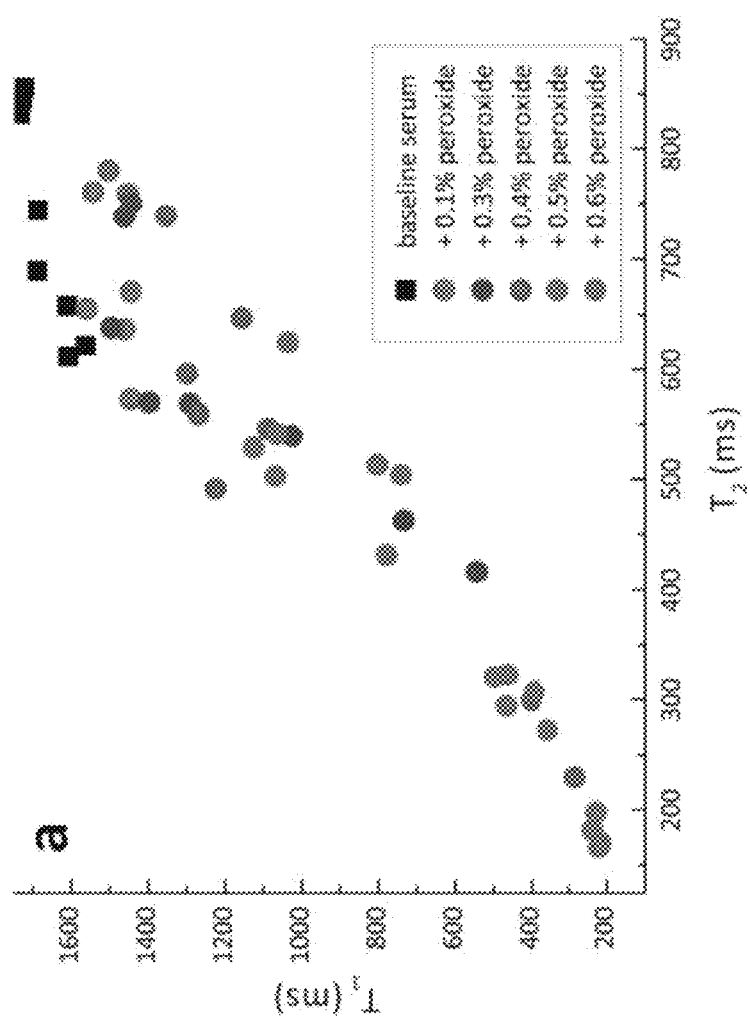
FIGS. 14A-14E show peroxide concentration selection criteria for peroxide-induced oxidation of human serum assays.
Figure 14B:
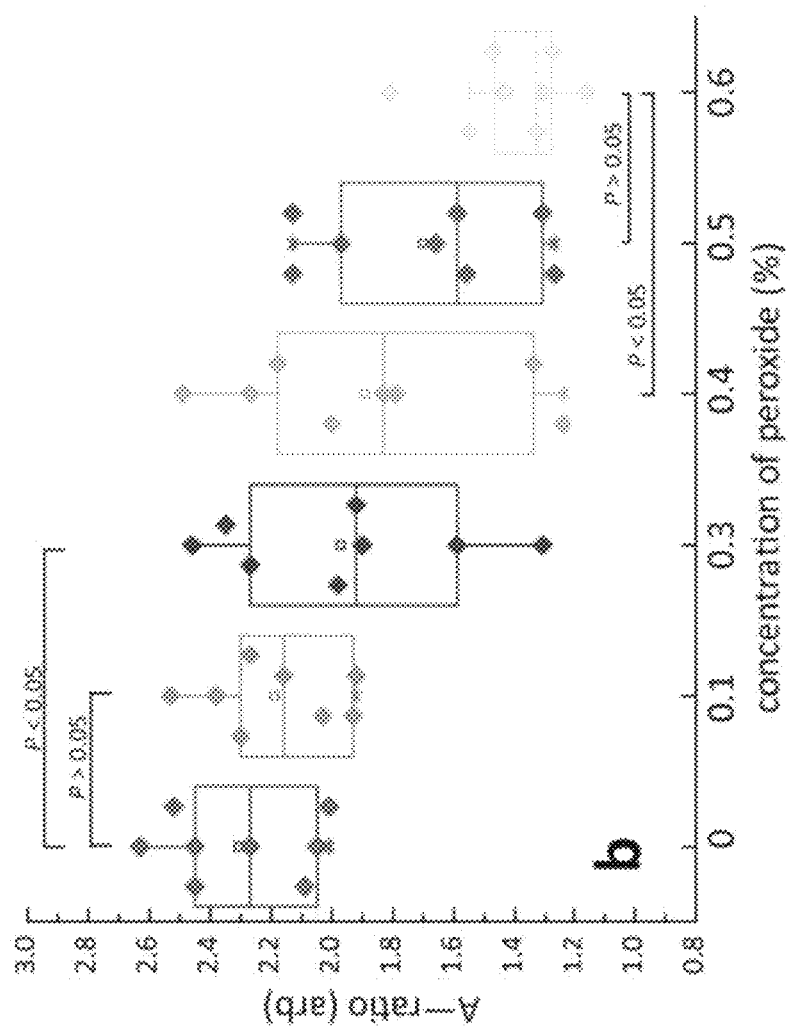
Figure 14C:
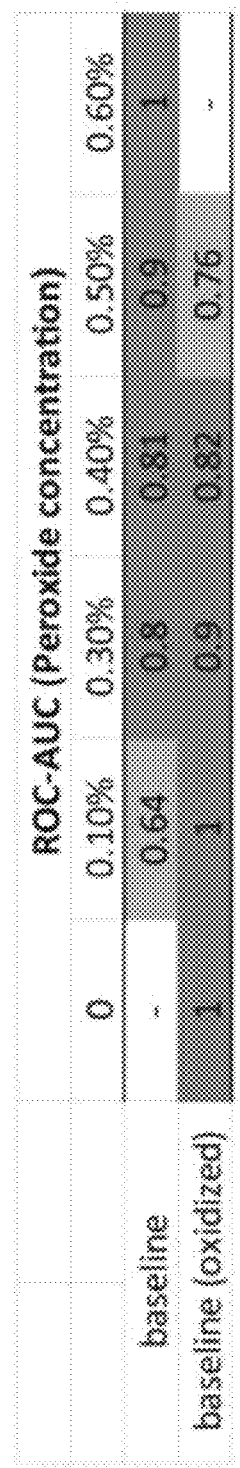
Figure 14D:
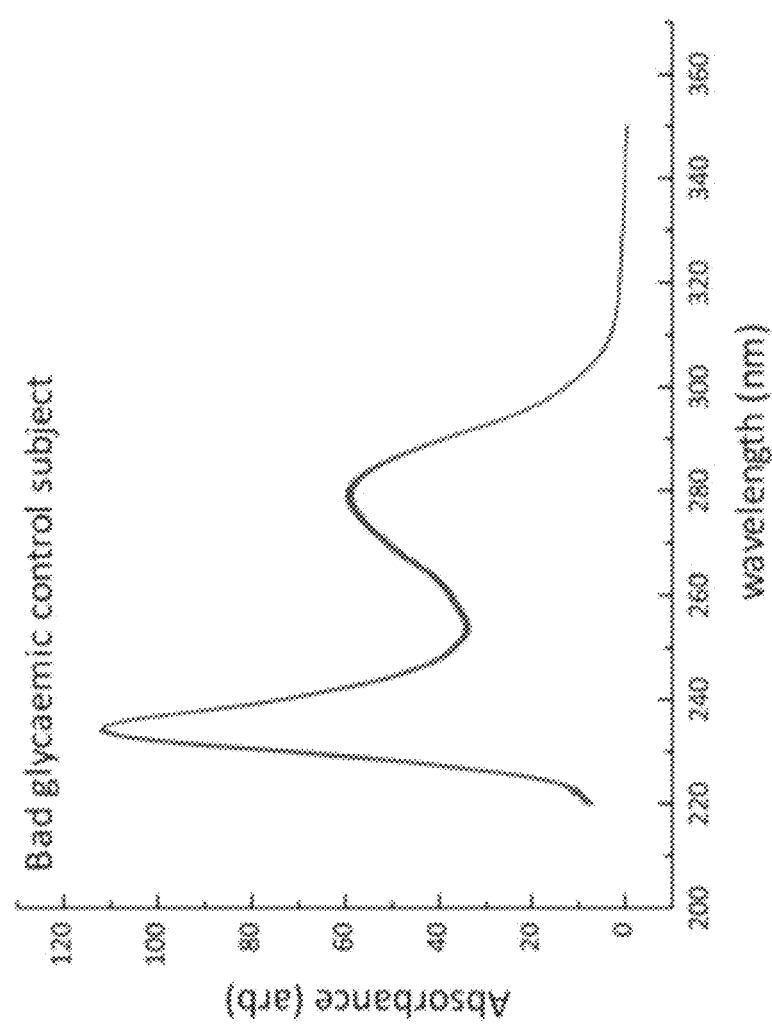
Figure 14E:
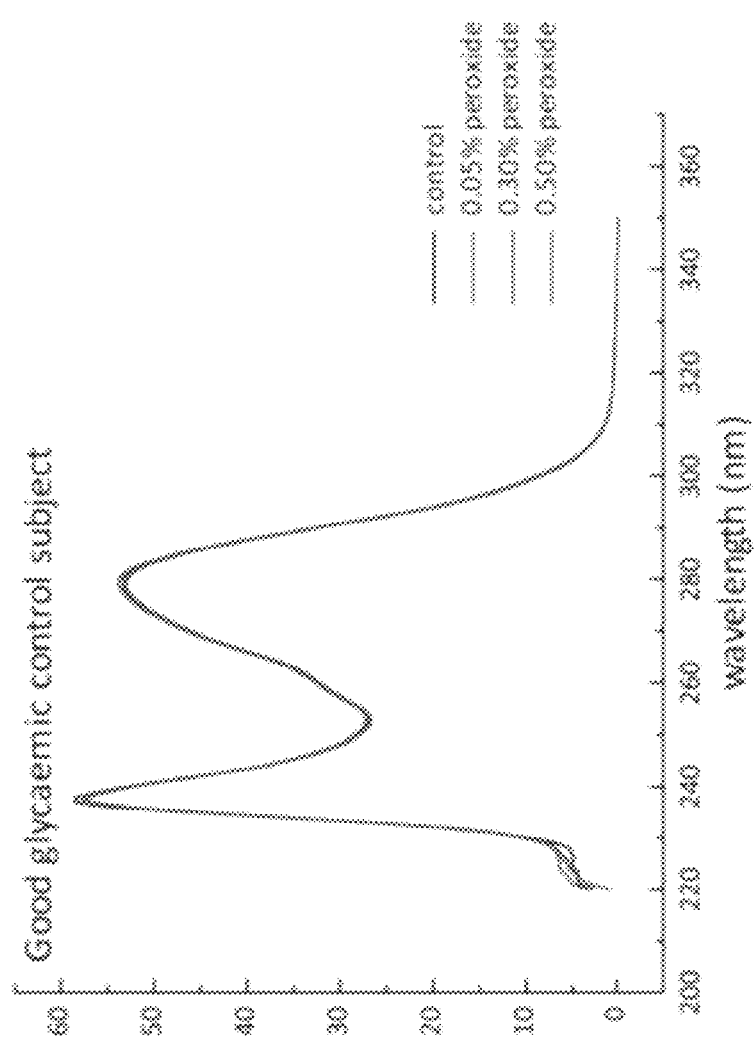

The same experiment was repeated but with increased hydrogen peroxide concentration of five folds to 500 nM. By Day 1 of post-exposure, the dropped in anti-oxidant capacity were registered in all the five subjects (FIG. 13D) and were much more significant as compared to previously observed (FIGS. 13B and 13C). One can translate this in vitro observation to understand the in vivo cellular damage. While acute infection and impaired ability to reproduce enzymes in congenital diseases are known to have averse effect, slight elevated stress above normal physiological condition over a prolonged period (e.g., chronic diseases, unhealthy diet) resulting in reduction anti-oxidant capacity. Under normal physiological condition however, cells would be able to constantly repair and renew themselves provided that proper nutrition and diet is within reach.

Low- and High Spin Ferric Hemoglobin in Diabetes Mellitus Subjects

Oxidative stress is constantly produced endogenously and exogenously. ROS is produced during oxygen metabolism and auto-oxidation, in which met-Hb is spontaneously produced. Most of met-Hb would normally be restored to its' reduced state under normal physiology condition. However, as cells age or under constant pathological stress, the distal histidine of the hemoglobin would bind to the iron and denatured to form hemichrome. See, Peisach, J., Blumberg, W. & Rachmilewitz, E. The demonstration of ferrihemochrome intermediates in Heinz body formation following the reduction of oxyhemoglobin A by acetylphenylhydrazine. *Biochimica et Biophysica Acta (BBA)-Protein Structure* 393, 404-418 (1975), and Bernhardt, I. & Ellory, J. Red cell membrane transport in health and disease. (2003), each of which is incorporated by reference in its entirety. Irreversible hemichrome would eventually aggregate and precipitates on cellular membrane. However, the actual physiological roles of hemichrome remains controversial. See, Rifkind, J. M., Abugo, O., Levy, A. & Heim, J. Detection, formation, and relevance of hemichromes and hemochromes. *Methods in enzymology* 231, 449-480 (1993), which is incorporated by reference in its entirety. While hemoglobin promotes most of the biological oxidant processes, oxidized Hb (e.g., HC, met-Hb and free heme) can be the source of stress themselves, and causes damage to RBCs membrane and cytoplasm, and functional impairments.

Figure 10A:
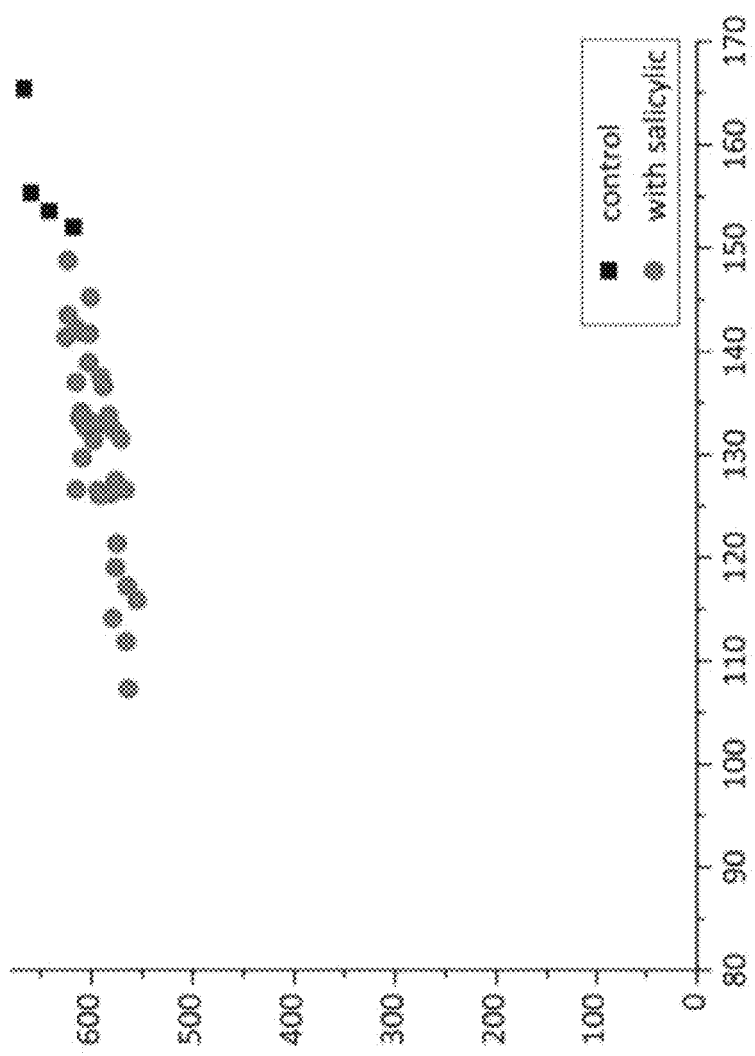
FIGS. 10A-10D show low- and high spin ferric hemoglobin in diabetes mellitus subjects.
Figure 10B:
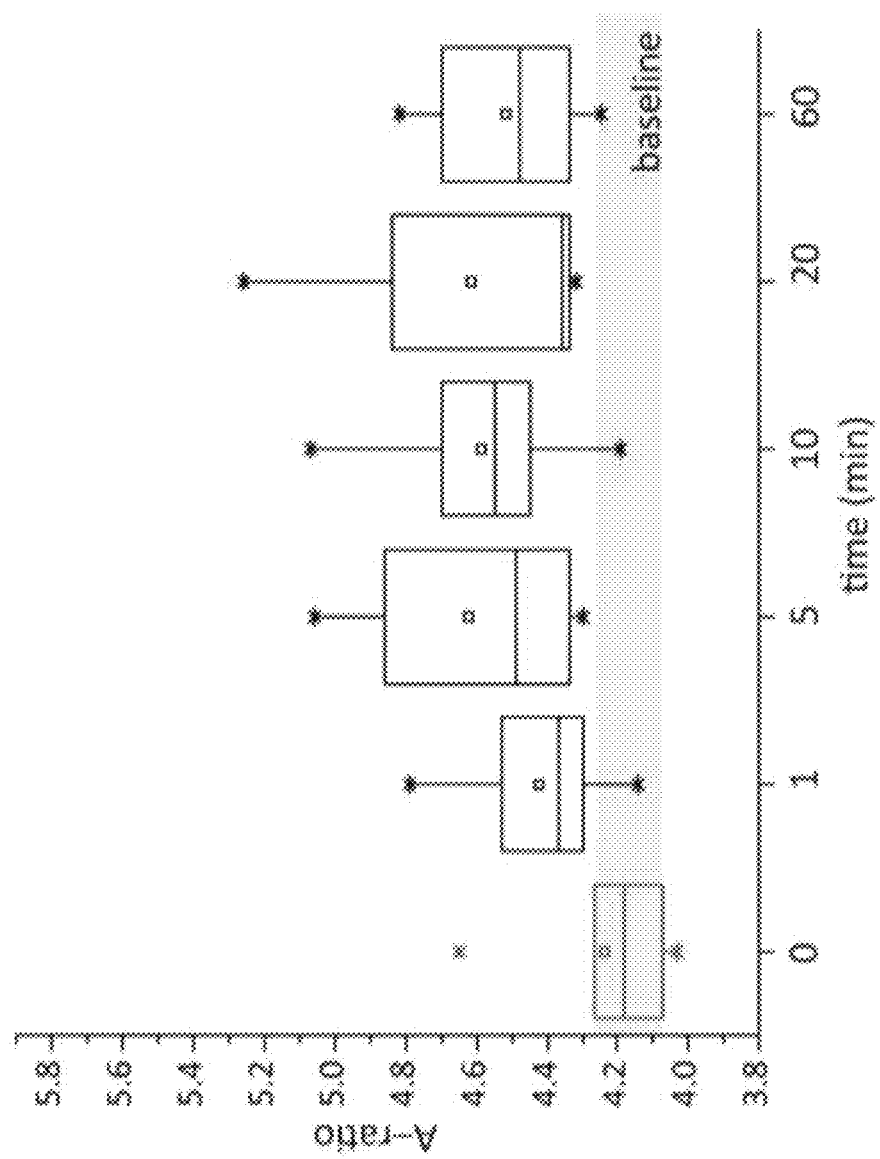
Figure 10C:
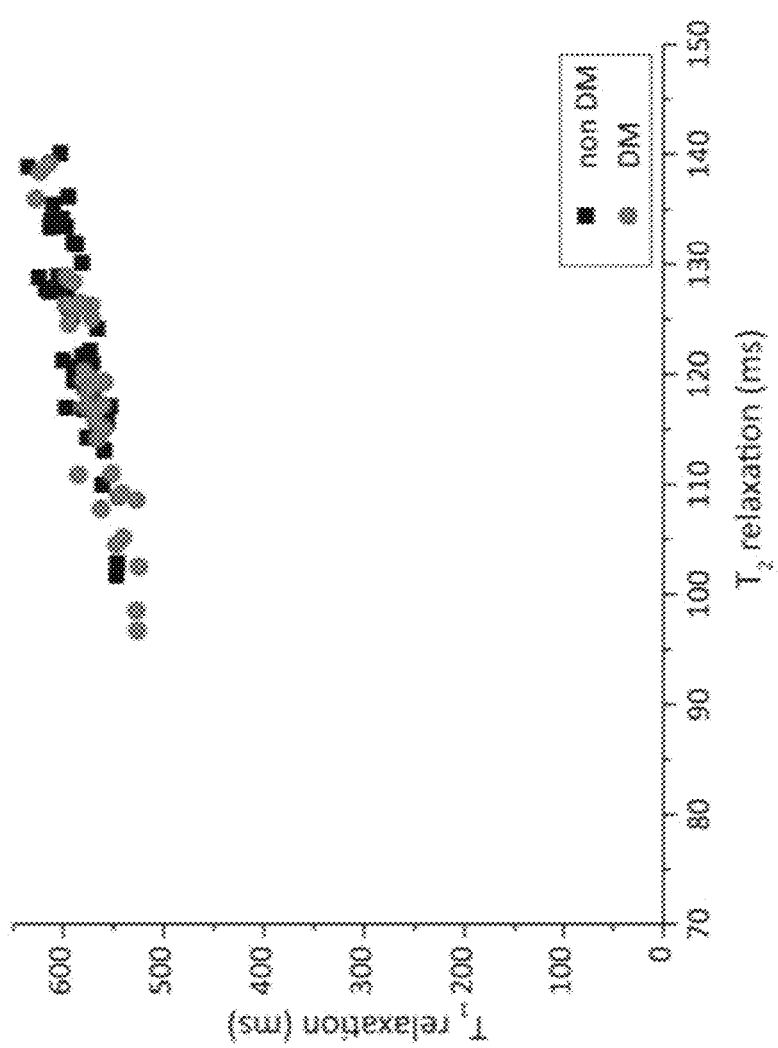
Figure 10D:
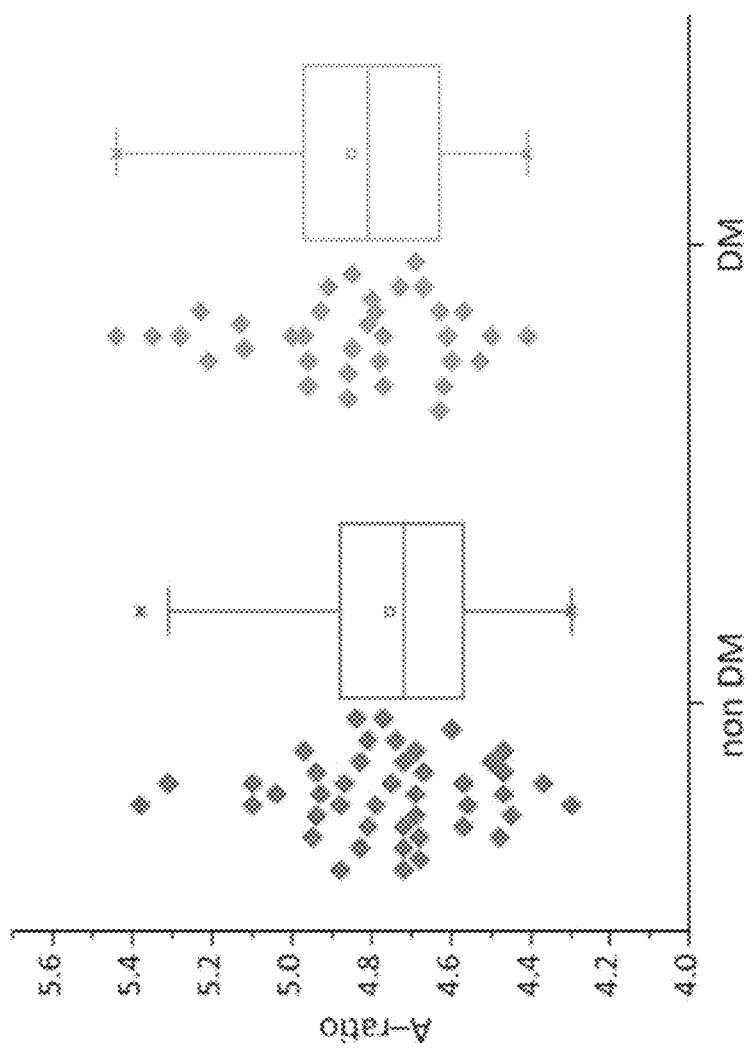

FIG. 10A shows the $T_1$-$T_2$ diagram of RBCs exposed to salicylic (round) and control (square) in in vitro environment at different time point (1, 5, 10, 20, 60) minutes. FIG. 10B shows the corresponding A-ratio in time evolution. FIG. 10C shows the $T_1$-$T_2$ diagram for RBCs of non DM (square) and DM subjects (round) exposed to 0.125M sodium salicylic (10 min). FIG. 10D shows the corresponding A-ratio.

Hemichrome (HC) can be induced in in-vitro environment by incubating sodium salicylic with freshly collected blood (FIG. 3A). HC is poorly resolved with a broad valley between 540-580 nm in spectrophotometer. See, Della Longa, S., et al. Iron site structure of two irreversible hemichromes from human hemoglobin, untreated and oxidized to sulfoxide at MetD6 (55) beta. *Biochimica et biophysica acta* 1294, 72-76 (1996), which is incorporated by reference in its entirety. In contrast, the MRR measurements indicate that high-spin met-Hb ($T_2$=98 ms, $T_1$=198 ms, A=2.02) and low-spin hemichrome ($T_2$=113 ms, $T_1$=587 ms, A=5.19) have unique relaxation times (and hence, the A-ratio). Although HC has similar ferric oxidation state as met-Hb, is in much lower spin-state with only 3 unpaired electrons (FIG. 1E). As distal histidine of the hemoglobin bound to the iron on the sixth coordinate, the $T_1$ for HC is therefore significantly longer than $T_1$ of met-Hb, which has water proton on the sixth coordinate, and therefore subject to different Brownian fluctuation. Thus, despite sharing the ferric-oxidation and in paramagnetic states, both HC and met-Hb is fully resolved as reflected in the state-diagram (FIG. 3B).

Peroxide Concentration Selection Criteria for Peroxide-Induced Oxidation of HSA Assays.

Two selection criteria can be used for an optimal range of peroxide concentration. Eight subjects were randomly selected from both the good and bad glycaemic control groups. Firstly, the induced stress requires to be statistically significant different (P-value <0.5 and AUC >0.8) from both the non-oxidized HSA and oxidized HSA baselines. Secondly, it is desirable to have large degree of inter-individual variability, as shown by the spread between 25% and 75% quantile box plots (FIGS. 14A-E). The 0.3% to 0.4% concentration range fit the selection. In these examples, 0.3% peroxide has been chosen unless mentioned otherwise.

In Vitro Glycation of Plasma Serum and Oxidative Status

In order to investigate the effect of glucose has on the plasma serum, in vitro glycation was performed by adding glucose (control, 10 mM and 100 mM) to freshly drawn plasma on three different subjects (Day 0) (Methods Online). MRR measurements, photospectrometry absorbance, and glucose in plasma were recorded simultaneously on day six after incubation. The initial plasma glucose readings were (5.6, 7.1, 7.3) mmol/L for subject A, B and C, respectively.

Figure 15A:
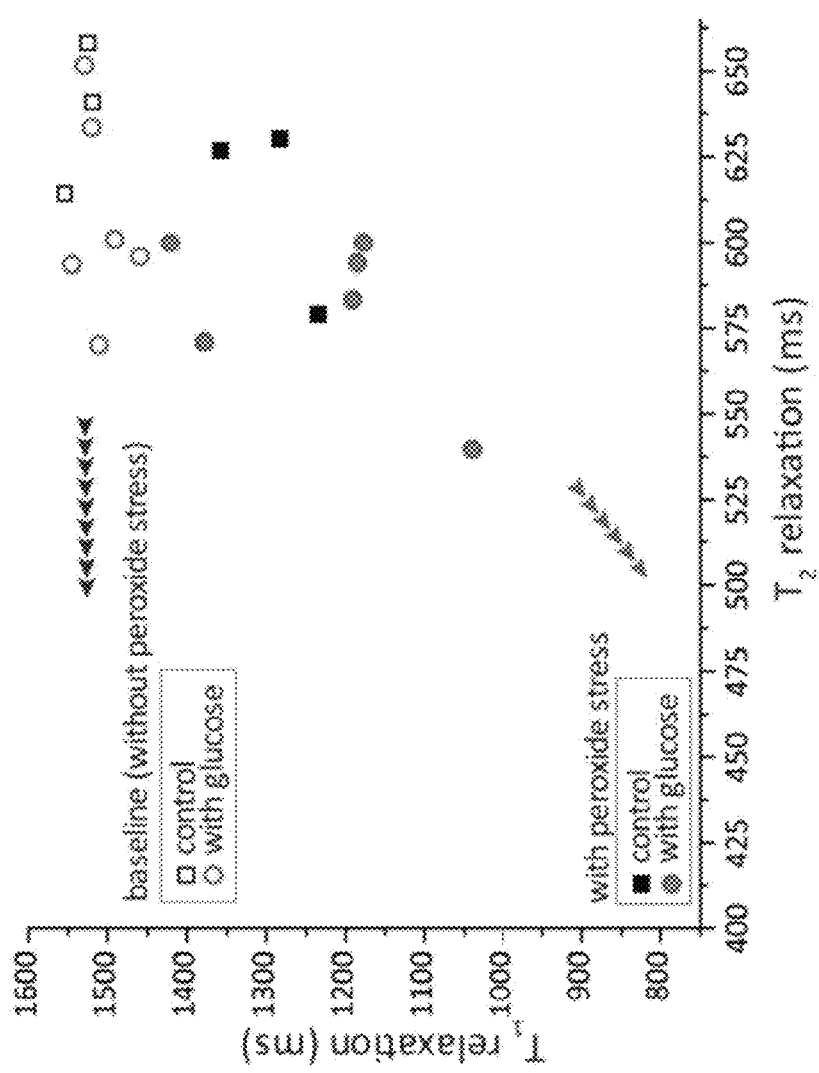
FIGS. 15A-15C show in vitro glycation of HSA and oxidative status.
Figure 15B:
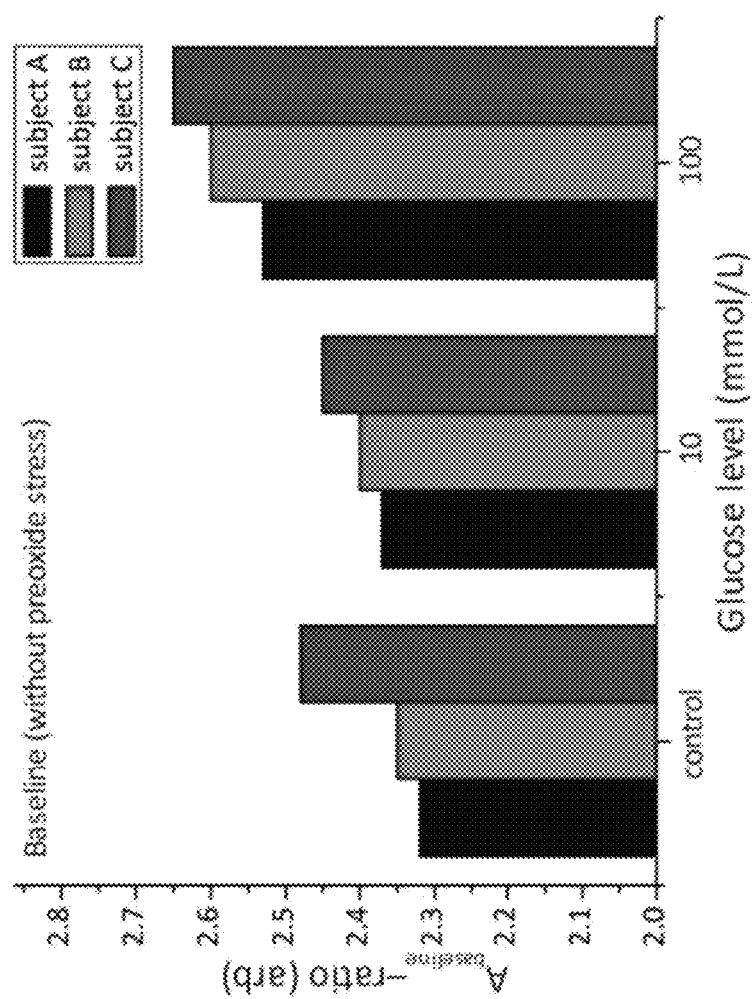
Figure 15C:
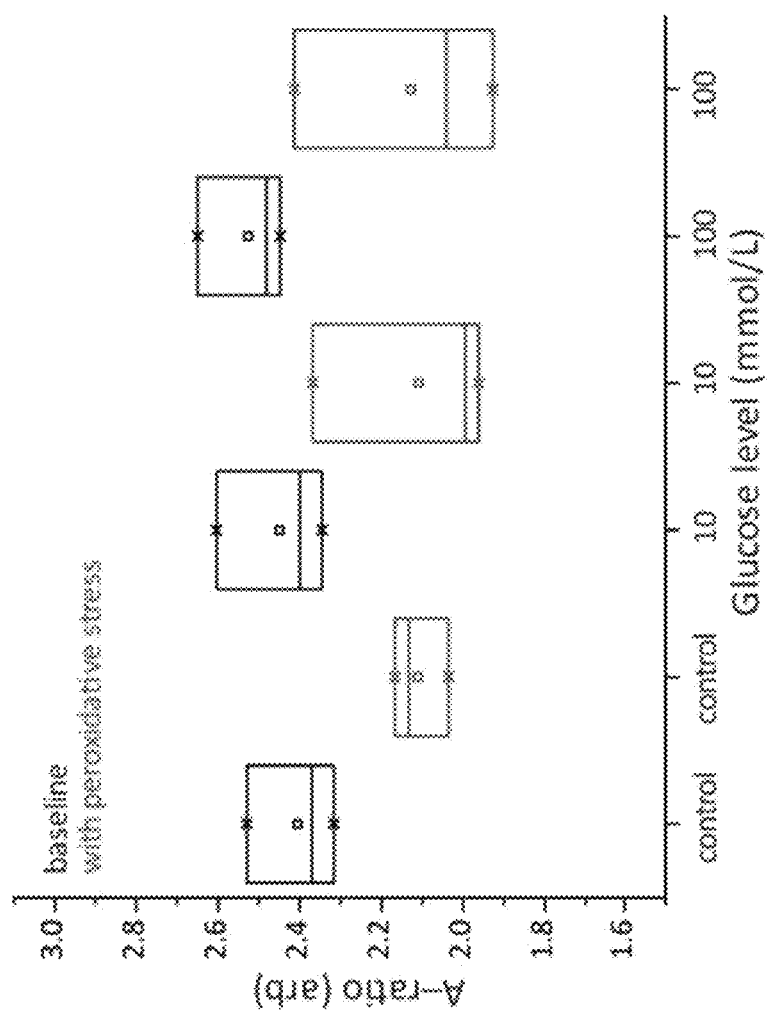

On Day 6, the $T_1$ and $T_2$ relaxations showed marked reduction as the amount of glucose increases on all the three subjects (FIGS. 15A and 15B). $T_2$ relaxation, however reduces much faster than $T_1$ relaxation (arrows in FIG. 15A), hence the increment of $A_{baseline}$-ratio (FIG. 15C) which were due to the effect of glycation. This corresponds well with the cross sectional study (in vivo measurements shown in FIG. 5A, and FIGS. 6A-6C). Peroxidative assay with 0.3% hydrogen peroxide reveals that the plasma serum has much lower antioxidant capacity as a function of glycaemic level (FIG. 15C; bottom three boxes). As more serum is oxidized, the $T_1$ relaxation time reduces much faster than $T_2$ relaxation time, and hence the reduction in $A_{peroxidative}$-ratio (FIG. 15C). Despite the fact that both glycation and glycoxidation shared the same effect of $T_1$ and $T_2$ relaxation times reduction, the $A_{peroxidative}$-ratio (bottom three boxes) and $A_{baseline}$-ratio (top three boxes) were orthogonal parameters (FIG. 15C), making it possible to differentiate between the two effects.

In vitro study here allows one to study the effect of glucose exposure quantitatively on the same subject to mimic the longitudinal study in actual in vivo subject. Furthermore, the effect of in vitro glycation and glycoxidation were similar as revealed in the cross sectional in vivo study (FIGS. 5 and 6). It is also worth noting that MRR measurements of 5.5 mM of glucose with and without 3% $H_2O_2$ mixture (10% v/v) were ($T_2$=2290, $T_1$=2441, A=1.07) and ($T_2$=2337, $T_1$=2461, A=1.05), respectively. This implied that either $H_2O_2$ does not interact directly with glucose (no physical and color changes or precipitate were observed) or did not alter the relaxation states substantially.

Figure 16B:
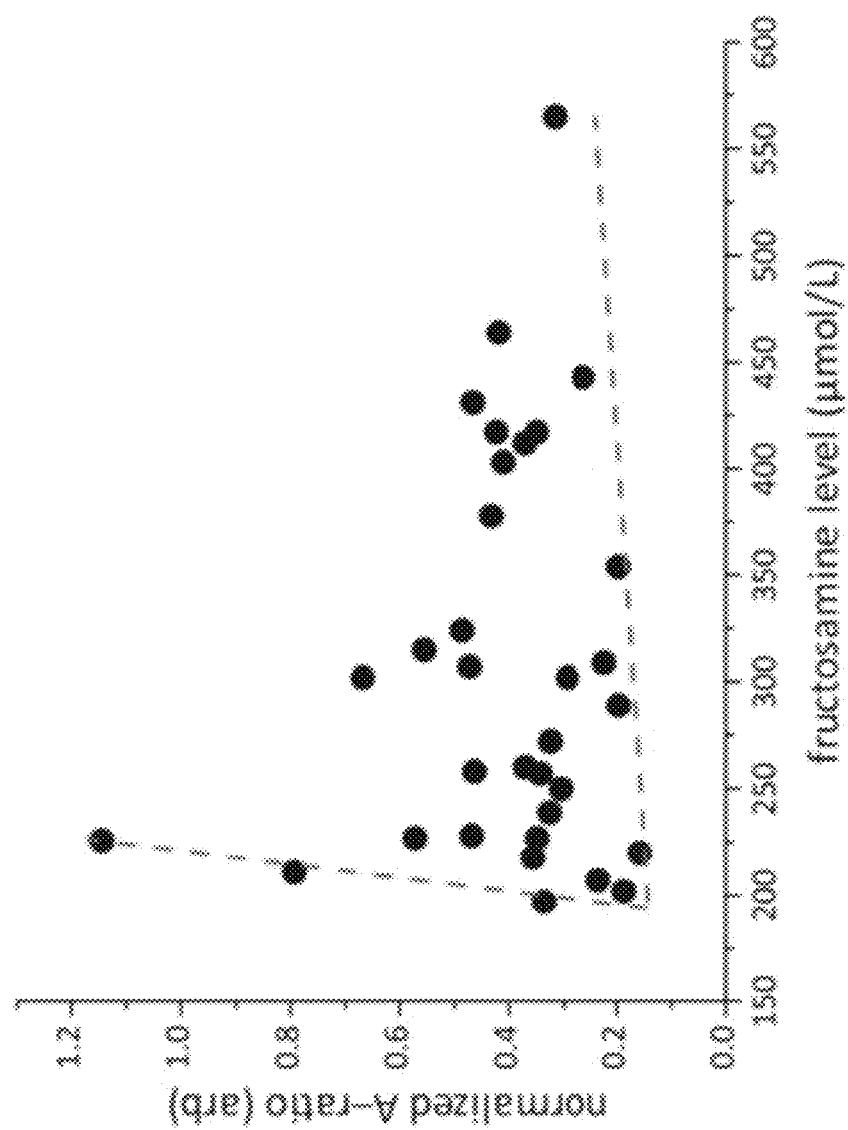
Figure 16C:
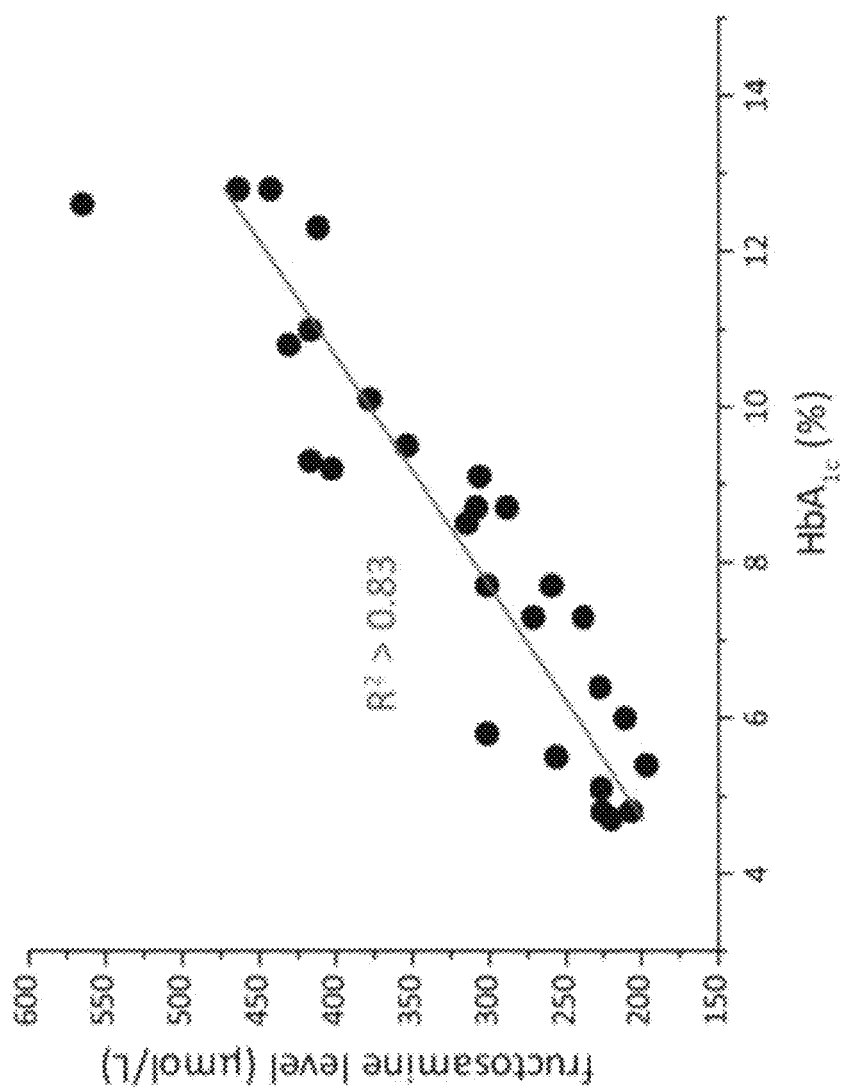

Clinical In Vivo Diabetes Subject: Correlation of Glycaemic Levels and MRR Oxidative Status The relationship between peroxidative susceptibility (normalized A-ratio) and glycaemic levels, for both the $HbA_{1c}$ and fructosamine, are investigated. MRR measurements were performed on the plasma serum using peroxidative assay. The peroxidative susceptibility was also found to be positively correlated to glycaemic levels, both the $HbA_{1c}$ (FIG. 16A) and fructosamine level (FIG. 16B). As expected the correlation between $HbA_{1c}$ and fructosamine were high ($R^2$>0.83), similar to the work reported by Hindle (FIG. 16C). See, Hindle, E., Rostron, G., Clark, S. & Gatt, J. Serum fructosamine and glycated haemoglobin measurements in diabetic control. *Archives of disease in childhood* 61, 113-117 (1986), which is incorporated by reference in its entirety. The degree of glycosylation of hemoglobin ($HbA_{1c}$) and serum proteins (fructosamine) has been correlated with indices of glycaemia. See, Johnson, R. N., Metcalf, P. A. & Baker, J. R. Fructosamine: a new approach to the estimation of serum glycosylprotein. An index of diabetic control. *Clinica Chimica Acta* 127, 87-95 (1983), and Johnson, R. N., Metcalf, P. A. & Baker, J. R. Relationship between albumin and fructosamine concentration in diabetic and non-diabetic sera. *Clinica chimica acta* 164, 151-162 (1987), each of which is incorporated by reference in its entirety.

Other embodiments are within the scope of the following claims.

What is claimed is:

1. A method of monitoring a disease status comprising:
   obtaining a sample from a subject,
   measuring a longitudinal relaxation time and a transverse relaxation time in the sample; and
   assessing a redox state of the sample from the longitudinal relaxation time and the transverse relaxation time of the sample,
   wherein the redox state is a level of nitrosative stress of hemoglobin.

2. The method of claim 1, wherein assessing the redox state includes:
   plotting a magnetic state diagram of a longitudinal relaxation time and a transverse relaxation time; and
   interpreting the state of the sample based on the location of the sample in the diagram.

3. The method of claim 1, wherein assessing the redox state includes:
   calculating a ratio of longitudinal relaxation time to transverse relaxation time of the sample; and
   comparing the ratio with a predetermined ratio of a reference sample.

4. The method of claim 1, wherein measuring the longitudinal relaxation time and the transverse relaxation time comprises:
   inserting the sample within a detection coil of a magnetic resonance relaxometry device.

5. The method of claim 4, wherein the device comprises:
   a radio-frequency spectrometer comprising at least one field-programmable gate array chip;
   a power amplifier electrically connected with the radio-frequency spectrometer and amplifying an electrical output of the radio-frequency spectrometer, thereby producing an amplified electrical signal comprising between about 0.1 Watts and about 10 Watts power;
   a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter; and
   at least one magnet supplying an external magnetic field to a detection region of the radio-frequency detection probe, the external magnetic field being less than about 3 Tesla.

6. The method of claim 4, wherein the device comprises an NMR spectroscopy using higher external magnetic field higher than about 3 Tesla.

7. The method of claim 1, wherein the sample is a blood sample.

8. The method of claim 6, wherein the blood sample is plasma or red blood cells.

9. The method of claim 1, wherein the disease is diabetes mellitus.

10. The method of claim 1, wherein the redox state is a level of oxidative stress.

11. The method of claim 1, wherein the redox state is a level of oxidative stress of hemoglobin.

12. The method of claim 1, wherein the redox state is a level of nitrosative stress.

13. A method of identifying a risk for diabetes mellitus in a patient comprising:
measuring a longitudinal relaxation time and a transverse relaxation time using a magnetic resonance relaxometry device in a blood sample of the patient;
calculating a ratio of longitudinal relaxation time to transverse relaxation time of the sample, wherein the longitudinal relaxation time and the transverse relaxation time are measured using a magnetic resonance relaxometry device, wherein the redox state is a level of nitrosative stress of hemoglobin; and
assigning a risk level to a subject based on a ratio of the longitudinal relaxation time and the transverse relaxation time.

14. The method of claim 13, wherein the device comprises:
a radio-frequency spectrometer comprising at least one field-programmable gate array chip;
a power amplifier electrically connected with the radio-frequency spectrometer and amplifying an electrical output of the radio-frequency spectrometer, thereby producing an amplified electrical signal comprising between about 0.1 Watts and about 10 Watts power;
a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter; and
at least one magnet supplying an external magnetic field to a detection region of the radio-frequency detection probe, the external magnetic field being less than about 3 Tesla.

15. The method of claim 13, wherein the magnetic resonance relaxometry device comprises an NMR spectroscopy using higher external magnetic field higher than about 3 Tesla.

16. A method of assessing a redox state of a sample comprising:
calculating a ratio of longitudinal relaxation time to transverse relaxation time of the sample, wherein the longitudinal relaxation time and the transverse relaxation time are measured using a magnetic resonance relaxometry device; and
comparing the ratio with a predetermined ratio of a reference sample,
wherein the redox state is a level of nitrosative stress of hemoglobin.

17. The method of claim 16, wherein the redox state is a level of oxidative stress.

18. The method of claim 16, wherein the redox state is a level of oxidative stress of hemoglobin.

19. The method of claim 16, wherein the redox state is a level of nitrosative stress.

20. The method of claim 16, wherein the sample is a blood sample.

21. The method of claim 20, wherein the blood sample is plasma or red blood cells.

22. The method of claim 16, wherein the magnetic resonance relaxometry device comprises:
a radio-frequency spectrometer comprising at least one field-programmable gate array chip;
a power amplifier electrically connected with the radio-frequency spectrometer and amplifying an electrical output of the radio-frequency spectrometer, thereby producing an amplified electrical signal comprising between about 0.1 Watts and about 10 Watts power;
a duplexer configured to isolate the radio-frequency spectrometer from the amplified electrical signal during a receiving mode of the device; a radio-frequency detection probe configured to transmit radio-frequency electromagnetic radiation to excite nuclei under resonance during a transmission mode of the device, the radio-frequency detection probe comprising a detection coil comprising an inner diameter of less than about 1 millimeter; and
at least one magnet supplying an external magnetic field to a detection region of the radio-frequency detection probe, the external magnetic field being less than about 3 Tesla.

23. The method of claim 16, wherein the magnetic resonance relaxometry device comprises an NMR spectroscopy using higher external magnetic field higher than about 3 Tesla.

* * * * *